United States Patent

Ohuchida et al.

[11] Patent Number: 5,169,957
[45] Date of Patent: Dec. 8, 1992

[54] BENZOPYRAN DERIVATIVES

[75] Inventors: Shuichi Ohuchida; Masaaki Toda; Tsumoru Miyamoto, all of Osaka, Japan

[73] Assignee: Ono Pharmaceutical Co., Ltd., Osaka, Japan

[21] Appl. No.: 736,321

[22] Filed: Jul. 26, 1991

Related U.S. Application Data

[62] Division of Ser. No. 491,876, Mar. 12, 1990, Pat. No. 5,055,598.

[30] Foreign Application Priority Data

Mar. 13, 1989 [JP] Japan .................................. 1-60317
Oct. 30, 1989 [JP] Japan .................................. 1-282805

[51] Int. Cl.$^5$ .................. C07D 311/04; C07D 311/92
[52] U.S. Cl. ...................................... 549/407; 549/389
[58] Field of Search ............................ 549/407, 389

[56] References Cited

U.S. PATENT DOCUMENTS 4,728,650 3/1988 Eziri et al. ........................ 549/407

FOREIGN PATENT DOCUMENTS 0202580 11/1986 European Pat. Off. .
87-246978/35 1/1986 Japan .

Primary Examiner—Nicky Chan
Attorney, Agent, or Firm—Sughrue, Mion, Zinn, Macpeak & Seas

[57] ABSTRACT

Benzopyran derivatives of the formula:

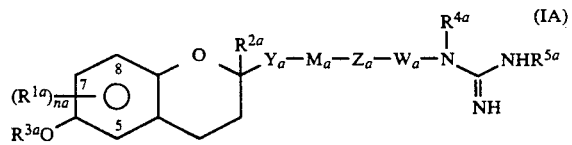

and the pharmaceutically acceptable acid addition salts thereof possess the inhibitory activity on Maillard reaction and an antioxidizing effect, and therefore, are useful for the prevention and treatment of several diabetic complications, diseases induced by aging and several diseases caused by formation of peroxidized fat.

6 Claims, No Drawings

BENZOPYRAN DERIVATIVES

This is a divisional of application Ser. No. 07/491,876 filed Mar. 12, 1990 now U.S. Pat. No. 5,055,598.

SUMMARY

This invention is related to benzopyran derivatives which are useful for medicines.

More particularly, this invention is related to
1) benzopyran derivatives of the formula:

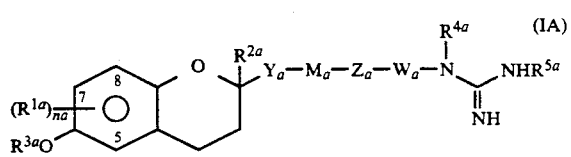

(wherein all of the symbols are the same meanings as hereinafter defined) and pharmaceutically acceptable acid addition salts thereof, 2) processes for the preparation of them, and 3) inhibitory agents on Maillard reaction and antioxidants containing the compound of the formula:

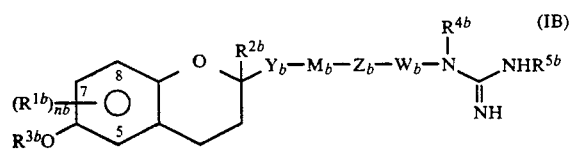

(wherein all of the symbols are the same meaning as hereinafter defined), which includes the compounds of the formula (1A), as active ingredient.

BACKGROUND

In 1912, Maillard reported that, when a mixture of amino acid and reducing sugar is heated, it shows brown color (called browning phenomenon). (Maillard, L. C., Compt. Rend. Soc. Biol., 72, 599 (1912)), and suggested that this reaction might occur in a body. In 1968, Rahbar reported that HbAlc, the glycosylated part of haemoglobin (Hg), was increased in diabetics (Rahbar, S., Clin. Chim. Acta., 22, 296 (1968)). Afterwards, it became clean that HbAlc had the chemical structure in which glucose binds to valine in N-terminal side of β-chain in the form of Amadori rearrangement (Koenig, R. J., Blobstein, S. H., & Cerami, A., J. Biol. Chem., 252, 2992 (1977)), and that Maillard reaction proceeds nonenzymatically (Stevens, V. J., Vlassara, H., Abati, A., & Cerami, A., J. Biol. Chem., 252, 2998 (1977)). These results showed that Maillard reaction occurs in a body.

As an initial step, Maillard reaction consists of forming the Amadori rearrangement products by glycosylation of reducing sugar with amino-group of protein. In the advanced stage of this reaction (1) cross-linked compounds (called advanced glycosylation and products (abbreviated as "AGE")) are produced, (2) solubility of them becomes low, (3) the products can not be easily degraded by the action of proteases, (4) a fluorescent is formed, and then (5) the products are colored brown.

The mechanism of AGE production has been proposed by some groups. For example, the theory of Brownlee et al is shown below (Brownlee, M. et al., Science, 232, 1629 (1986)).

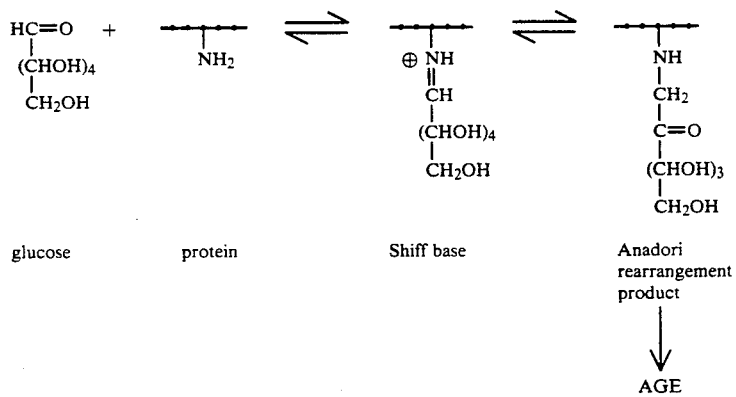

Maillard reaction is observed in healthy person, and particulary this is caused notably in diabetics that a level of blood sugar is high and in protein of which metabolic turnover is slow.

For example, in the case of haemoglobin, the level of glycosylation in diabetic mouse are 2.7 times as high as that of normal mouse (Monnier, V. M. et al., The Maillard Reaction in Foods and Nutrition, ACS Symposium Series, 215, 432, Am. Chem. Soc., Washington, D.C. (1983)), and glycosylation of serum albumin in diabetics was advanced (Guthrow, C. E. et al., Proc. Natl. Acad. Sci. U.S., 76, 4258 (1979)).

Further, it was turned out that, when a glycosylated serum protein was administrated intravenously during 12 weeks, the typical diabetic renal lesion was observed (Monnier, V. M. et al., Clin. Endocrinol. Metab., 11, 431 (1982)).

Crystallin in lens is the special protein which is not metabolized at all after its biosynthesis. When crystallin was glycosylated, its steric structure was transformed and the SH groups were enzymatically oxidized to form S-S bond. A sequence of processes induced to polymerize the protein in crystallin.

In the case of diabetic cataract in rats, the ratio of binding of protein and glucose was ten times as high as that of normal rat, and also intramolecular S-S bond formation increased (Monnier, V. M. & Cerami, A., Clin. Endocrinol. Metab. 11, 431 (1982)).

Glycosylation of crystallin caused its polymerization, decrease in its solubility, formation of fluorescent substance, and further yellow and brown coloring. This phenomenon is very similar to that of lens by aging (Chiou, S. H., Chylack, L. T., Jr., Tung, W. H., & Bunn, F., J. Biol. Chem., 256, 5176 (1981)).

Collagen and elastin in connective tissue contain lysine and hydroxylysine abundantly, the speed of their metabolic turnover is slow, and the existance of reactants with glucose at the basement membrane of renal adrenal glands, skin and tendon has been found (Monnier, V. M., Stevens, V. J., & Cerami, A., Maillard Reactions in Food, Prog. Food Nutr. Sci., 5, 315, Pergamon Press, London), further these glycosylation products might be related to sclerosis in a blood vessel wall (Rosenburg, H., Modrak, J. B., Hassing, J. M., Al-Turk, W. A., & Stohs, S. J., Biochem. Biophys. Res. Commun, 91, 498 (1979)).

The cause of diabetic neurosis may be nonenzymatic glycosylation of neuro-myelin protein (Monnier, V. M. et al., Clin. Endocrinol. Metab., 11, 431 (1982)).

In this way, Maillard reaction in a body is related to not only various diabetic complication but also a lot of diseases accompanied with aging.

Moreover, in recent research, it is reported that free radical relates to glycosylation of protein. (Diabete & Metabolism (Paris), 14, 25-30 (1988)).

RELATED ARTS

On the above background, recently, researches of Maillard reaction inhibitors have been carried out. For example, Brownlee, M. et al. showed that aminoguanidine inhibits Maillard reaction in vitro, and that aminoguanidine, administered to diabetic rats, inhibits diabetes-induced accumulation of advanced glycosylation end products in arterial wall connective tissue protein (Brownlee, M. et al., Science, 232, 1629 (1986)).

They have considered that the amino group of a nucleophilic hydrazine compound (i.e. the amino group which is bonded to guanidino group in aminoguanidine) blocks reactive carbonyls on early glycosylation products, and inhibits further cross-link formation of chemically reversible Amadori product.

Further, in the specification of Japanese Patent Kokai No. 62-142114, i.e. European Patent Publication No. 222313, it was suggested that the pharmaceutical composition comprising compound having the group containing reactive nitrogen atoms, which enable to react with reactive carbonyls in chemically reversible Amadori product, inhibits the production of advanced glycosylation end products. Concretely, the compositions comprising aminoguanidine, α-hydrazinohistidine and lysine are disclosed.

And further, as the compounds which have an equal or similar structure with those of this invention, the compounds of the formula as follows are suggested.

(1) In the specification of Japanese Patent Kokai No. 61-260077, i.e. European Patent Publication No. 202580, it is disclosed that the compounds of the formula:

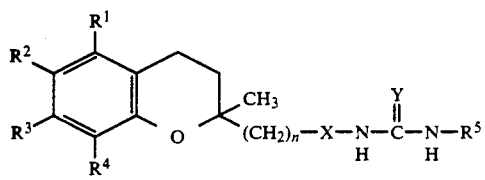

(wherein $R^1$, $R^4$ and $R^5$ severally represent a hydrogen atom or lower alkyl group, $R^2$ represents a hydrogen atom, halogen atom, hydroxy group, lower alkoxy group or lower alkenyloxy group, $R^3$ represents a hydrogen atom, lower alkyl group or lower alkoxy group, X represents a methylene group or carbonyl group, Y represents a sulfur atom or imino group, n represents an integer of 0, 1 or 2) are useful as anti-peptic ulcer agent.

(2) In the specification of Japanese Patent Kokai No. 62-169726, i.e. Derwent accession No. 87-246978/35, it is disclosed that the compounds of the formula

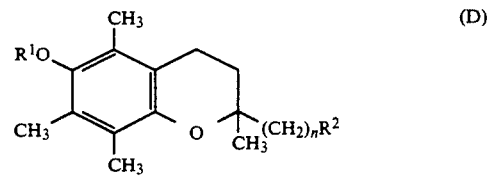

(wherein $R^1$ represents a hydrogen atom, $R^2$ represents a hydroxy group or guanidinocarbonyl group, n represents an integer of 1 to 3.) are useful as 5-lipoxygenase inhibitor.

DISCLOSURE OF THE INVENTION

The present inventors have searched for the compounds, which possess a superior inhibitory effect on Maillard reaction and high safety, and have already filed patent applications for aminoguanidine derivatives (see European Patent Publication Nos. 325936 and 339496). And, according to recent research, the present inventors have found that the compounds of the present invention which chroman skeletons are introduced into aminoguanidine derivatives also accomplish the purpose. Moreover, according to next research, we have found that the compounds possess an antioxidation effect besides an inhibitory effect on Maillard reaction.

Accordingly, the present invention is related to:

1) benzopyran derivatives of the formula:

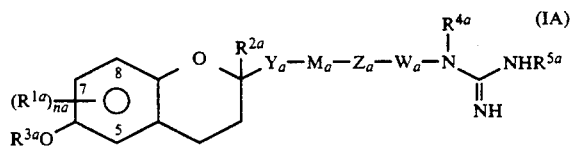

wherein $R^{1a}$ is hydrogen, C1–4 alkyl or C1–4 alkoxy; or two $R^{1a}$ taken together with 7th- and 8th-carbon to which they are attached form C6 carbocyclic ring;
$R^{2a}$ is hydrogen, C1–4 alkyl or C1–4 alkoxy;
$R^{3a}$ is hydrogen, C2–4 acyl or benzoyl;
na is 1–3;
Ya is C1–7 alkylene, C2–7 alkenylene or C2–7 alkynylene;
Ma is
 i) bond or
 ii) a group of the formula: —Da—Ba—;
Da is
 i) —O— or
 ii) —S—;
Ba is
 i) C1–4 alkylene or
 ii) a group of the formula:

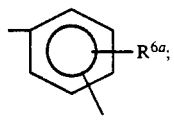

Za is
i) bond,
ii) —OCO—,
iii) —CONR$^{9a}$—,
iv) —COO—,
v) —NR$^{9a}$CO—,
vi) —O— or
vii) —NH—CO—NH—;
Wa is a group of the formula: —W1a—Aa—W2a—;
Aa is
i) bond or
ii) a group of the formula:

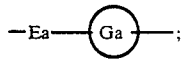

Ea is
i) bond,
ii) —O— or
iii) —S—;
(Ga) is C4–10 carbocyclic or heterocyclic ring substituted by one to three C1–4 alkyl, C1–4 alkoxy, halogen, a group of the formula: —COOR$^{7a}$, trihalomethyl or acetamido;
W1a and W2a each, independently, is
i) bond
ii) C1–4 alkylene,
iii) C2–4 alkenylene or
iv) C2–4 alkynylene;
R$^{4a}$ is hydrogen or C1–4 alkyl;
R$^{5a}$ is hydrogen, C1–4 alkyl or amino;
R$^{6a}$ is hydrogen, C1–4 alkyl, C1–4 alkoxy, halogen, a group of the formula: —COOR$^{8a}$, trihalomethyl or acetoamido;
R$^{7a}$ is hydrogen or C1–4 alkyl;
R$^{8a}$ is hydrogen or C1–4 alkyl;
R$^{9a}$ is hydrogen, C1–4 alkyl or benzyl;
with the proviso that:
i) Da is bonded to Ya and Ba is bonded to Za;
ii) Ea is bonded to W1a and (Ga) is bonded to W2a;
iii) a double or triple bond in alkenylene or alkynylene is not directly bonded to oxygen;
iv) when Aa represents

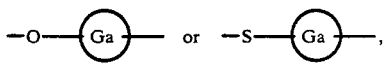

W1a does not represent a bond;
v) the following compound is excluded:
wherein R1a attached to the 5th-carbon is hydrogen or C1–4 alkyl;
R$^{1a}$ attached to the 7th-carbon is hydrogen, C1–4 alkyl or C1–4 alkoxy;
R$^{1a}$ attached to the 8th-carbon is hydrogen or C1–4 alkyl;
R$^{2a}$ is methyl;
R$^{3a}$ is hydrogen;
R$^{4a}$ is hydrogen;
R$^{5a}$ is hydrogen;

—Ya—Ma—Za—Wa— is C1-3 straight-chain alkylene;
and the pharmaceutically acceptable acid addition salts thereof,
2) processes for the preparation of them,
3) inhibitory agents on Maillard reaction and antioxidants containing, as active ingredient, the compound of the formula:

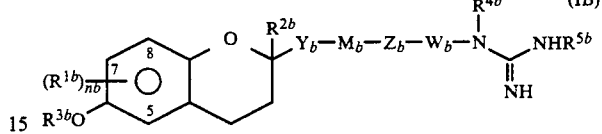

wherein R$^{1b}$ is hydrogen, C1–4 alkyl or C1–4 alkoxy; or two R$^{1b}$ taken together with 7th- and 8th-carbon to which they are attached form C6 carbocyclic ring;
R$^{2b}$ is hydrogen, C1–4 alkyl or C1–4 alkoxy;
R$^{3b}$ is hydrogen, C2–4 acyl or benzoyl;
nb is 1–3;
Yb is C1–7 alkylene, C2–7 alkenylene or C2–7 alkynylene;
Mb is
i) bond or
ii) a group of the formula: —Db—Bb—;
Db is
i) —O—or
ii) —S—;
Bb is
i) C1–4 alkylene or
ii) a group of the formula:

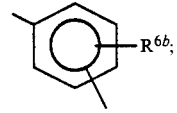

Zb is
i) bond,
ii) —OCO—,
iii) —CONR$^{9b}$—,
iv) —COO—,
v) —NR$^{9b}$CO—,
vi) —O—or
vii) —NH—CO—NH—;
Wb is a group of the formula: -W1b-Ab-W2b-;
Ab is
i) bond or
ii) a group of the formula:

Eb is
i) bond,
ii) —O—or
iii) —S—;
(Gb) is C4–10 carbocyclic or heterocyclic ring; or C4–10 carbocyclic or heterocyclic ring substituted by one to three C1–4 alkyl, C1–4 alkoxy, halogen, a group of the formula: —COOR$^{7b}$, trihalomethyl or acetamido;
W1b and W2b each, independently, is
i) bond
ii) C1–4 alkylene,
iii) C2–4 alkenylene or iv) C2-4 alkynylene;
$R^{4b}$ is hydrogen or C1-4 alkyl;
$R^{5b}$ is hydrogen, C1-4 alkyl or amino;
$R^{6b}$ is hydrogen, C1-4 alkyl, C1-4 alkoxy, halogen, a group of the formula: —COOR$^{8b}$, trihalomethyl or acetoamido;
$R^{7b}$ is hydrogen or C1-4 alkyl;
$R^{8b}$ is hydrogen or C1-4 alkyl;
$R^{9b}$ is hydrogen, C1-4 alkyl or benzyl;
with the proviso that:
  i) Db is bonded to Yb and Bb is bonded to Zb;
  ii) Eb is bonded to W1b and (Gb) is bonded to W2b;
  iii) a double or triple bond in alkenylene or alkynylene is not directly bonded to oxygen;
  iv) when Ab represents

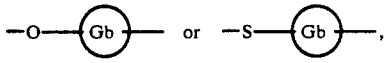

W1b does not represent a bond; or the pharmaceutically acceptable acid addition salts thereof.

COMPARISON WITH RELATED ARTS

The compounds of the formula (IA), of the present invention are not disclosed in the formulae (C) and (D), and therefore, are quite novel. A part of the compounds of the formula (IB) has been already disclosed in the formula (C). However, it is only described that the compounds of the formula (C) are useful as anti-peptic ulcer agents and the compounds of the formula (D) are useful as 5-lipoxygenase inhibitor. These description does not teach and suggest that the compounds of the formulae (IA) and (IB), of the present invention possess an inhibitory effect on Maillard reaction and antioxidation effect. Accordingly, the compounds of the present invention are unobvious over the related arts.

The present invention includes all isomers unless otherwise specified. For example, alkyl group, alkoxy group, alkylene group and alkenylene group mean straight chain or branched-chain alkyl group, alkoxy group, alkylene group, and the double-bond in alkenylene group includes E, Z and mixture of E and Z. And, in case of existing branched-chain alkyl group, the present invention includes the isomers caused by existing asymmetrical carbon atoms.

In the formulae (IA) and (IB), alkyl groups of from 1 to 4 carbon atom(s) shown by $R^{1a}$, $R^{1b}$, $R^{2a}$, $R^{2b}$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$ and substituents in (Ga) and (Gb) are methyl, ethyl, propyl, butyl group and isomeric groups thereof. Alkoxy groups of from 1 to 4 carbon atom(s) shown by $R^{1a}$, $R^{1b}$, $R^{2a}$, $R^{2b}$, $R^{6a}$, $R^{6b}$ and substituents in (Ga) and (Gb) are methoxy, ethoxy, propoxy, butoxy group and isomeric groups thereof. Every groups are preferable. C6 carbocyclic ring shown by the group which two $R^{1a}$ and two $R^{1b}$ represent together with 7th- and 8th- carbon atoms are benzene ring and the rings which may be partially or fully saturated thereof. Every rings are preferable. $R^{1a}$, $R^{1b}$, $R^{2a}$, $R^{2b}$, $R^{4a}$, $R^{4b}$, $R^{7a}$, $R^{7b}$, $R^{8a}$ and $R^{8b}$ also preferably represent a hydrogen atom. $R^{9a}$ and $R^{9b}$ also preferably represent a hydrogen atom or benzyl.

In the formulae (IA) and (IB), acyl groups of from 2 to 4 carbon atoms shown by R3a and R3b are acetyl, propionyl, butyryl group and isomeric groups thereof. Every group are preferable. $R^{3a}$ and $R^{3b}$ are also preferable to represent a hydrogen atom and benzoyl group. $R^{5a}$ and $R^{5b}$ are also preferable to a hydrogen atom or amino group.

In the formulae (IA) and (IB), alkylene groups of from 1 to 7 carbon atoms shown by Ya and Yb are methylene, ethylene, trimethylene, tetramethylene, pentamethylene, hexamethylene, heptamethylene group and isomeric groups thereof. Every groups are preferable. Alkylene group of from 1 to 4 carbon atom(s) shown by Ba, Bb, W1a, W1b, W2a and W2b are methylene, ethylene, trimethylene, tetramethylene group and isomeric groups thereof.

In the general formulae (IA) and (IB), alkenylene groups of from 2 to 7 carbon atoms shown by Ya and Yb are the groups which contain one or two double bond(s) in ethylene, trimethylene, tetramethylene, pentamethylene, hexamethylene, heptamethylene group and isomeric group thereof. Alkenylene groups of from 2 to 4 carbon atoms shown by W1a, W1b, W2a and W2b are the groups which contain one or two double bond(s) in ethylene, trimethylene, tetramethylene group and isomeric group thereof, preferably, vinylene, propenylene, 1-butenylene.

In the formulae (IA) and (IB), alkynylene group of from 2 to 7 carbon atoms shown by Ya and Yb, are the groups which contain one or two triple bond(s) in ethylene, trimethylene, tetramethylene, pentamethylene, hexamethylene, heptamethylene and isomeric group thereof. Alkynylene group of from 2 to 4 carbon atoms shown by W1a, W1b, W2a and W2b are the groups which contain one or two triple bond(s) in ethylene, trimethylene, tetramethylene group and isomeric group thereof, preferably ethynylene, propynylene, 1-butynylene group and isomeric group thereof.

In the formulae (IA) and (IB), trihalomethyl group shown by $R^{6a}$, $R^{6b}$, substituents in (Ga) and (Gb) are trifluoromethyl, trichloromethyl, tribromomethyl, triiodomethyl group. Halogen atom shown by $R^{6a}$, $R^{6b}$, substituents in (Ga) and (Gb) are fluorine, chlorine, bromine and iodine atom. Every group are preferable. $R^{6a}$ and $R^{6b}$ also preferably represent a hydrogen atom and acetamido group. Substituents in (Ga) and (Gb) also preferably represent acetamido group. (Ga) and (Gb) also preferably represent unsubstituted carbocyclic or heterocyclic ring.

In the formulae (IA) and (IB), carbocyclic ring of from 4 to 10 carbon atoms shown by (Ga) and (Gb) are mono- or bi- aromatic ring. This rings are, for example, benzene, pentalene, indene, naphthalene, azulene ring which may be partially or fully saturated.

Preferable rings are benzene, naphthalene ring and cycloalkane ring of from 4 to 7 carbon atoms. More preferable rings are benzene ring and cyclohexane ring.

In the formulae (IA) and (IB), heterocyclic ring of from 4 to 10 carbon atoms shown by (Ga) and (Gb) are mono- or bi- heterocyclic rings which may be partially or fully saturated. For example, they are furan, thiophene, pyrrole, oxazole, isoxazole, thiazole, isothiazole, imidazole, pyrazole, furazan, pyridine, pyridazine, pyrimidine, pyrazine, indole, isoindole, benzofuran, benzothiophene, indolizine, chromene, quinoline, isoquinoline, quinolizine, purine, indazole, quinazoline, cinnoline, quinoxaline, phthalazine, pteridine rings and partially or fully saturated rings thereof.

Aa, Ab, W1a, W1b, W2a and W2b also preferably represent a bond.

The compounds of the formulae (IA) and (IB), if desired, may be converted into acid addition salts by the known methods. Preferably, acid addition salts are non-toxic salts and water-soluble. The suitable acid addition salts are, for example, hydrochloric acid, hydrobromic acid, hydroiodic acid, sulfuric acid, phosphoric acid, an inorganic acid such as nitric acid, or an organic acid such as acetic acid, lactic acid, tartric acid, benzoic acid, citric acid, methanesulphonic acid, ethanesulphonic acid, benzenesulphonic acid, toluenesulphonic acid, isethionic acid, glucuronic acid and gluconic acid. Acid addition salts may be obtained by the known methods, for example, by reacting stoichiometric quantities of a compound of formula (IA) or (IB) and the appropriate acid in a suitable solvent.

Process for the preparation of the compounds of the present invention

The compounds of the formula (IA), of the present invention may be prepared by the methods described hereinafter. Moreover the compounds of the formula (IB), of the present invention may be prepared by the methods as described for those of the formula (IA).

Step 1:

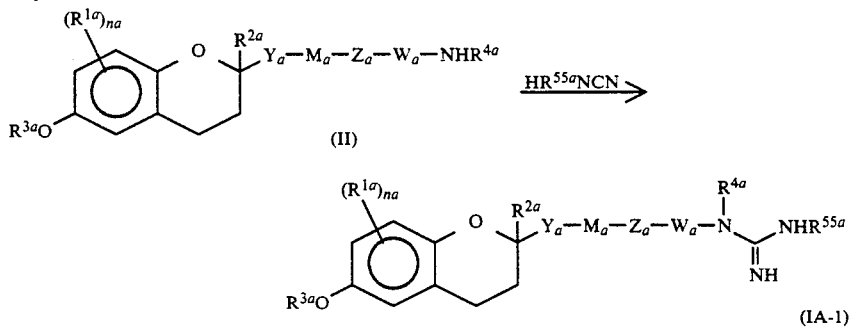

Step 2:

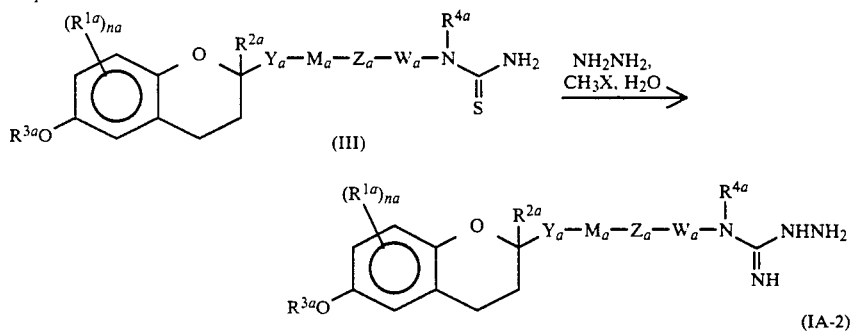

Step 3:

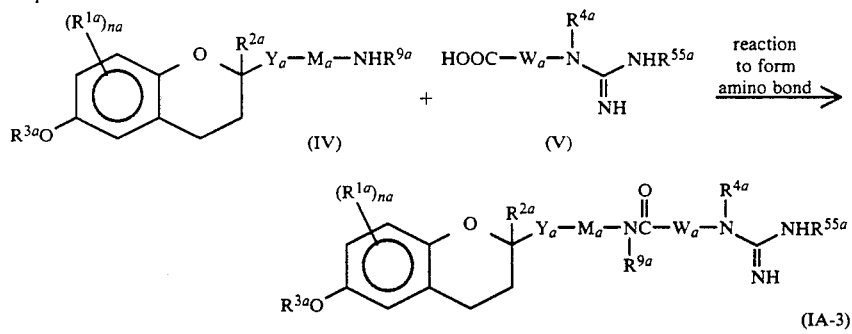

Step 4:

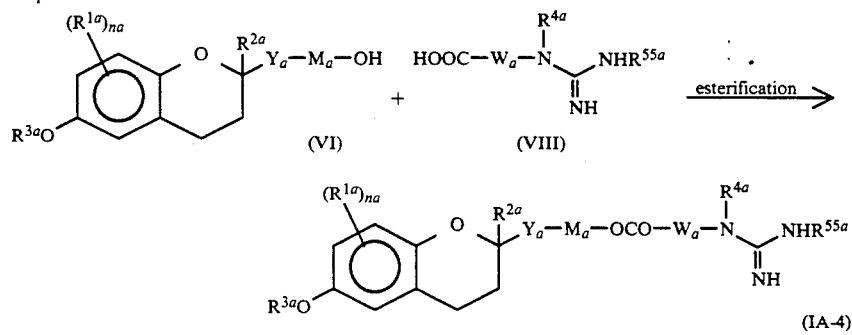

(wherein $R^{55a}$ is hydrogen or C1-4 alkyl; X is chlorine, bromine and iodine; and the other symbols are the same meanings described hereinbefore.)

Step 1 may be carried out, for example, in an inert organic solvent (ethanol, methanol etc.).

Step 2 may be carried out, for example, by reacting with methyl halide (methyl iodide etc.) followed by hydrazine in an inert organic solvent (ethanol, methanol etc.).

Step 3 is the reaction to form amido bond. For example, it may be carried out by reacting:

(i) in an inert organic solvent (methylene chloride, toluene etc.), using dicyclohexylcarbodiimide (DCC) or 2-chloro-1-methylpyridinium iodide or a tertiary amine (triethylamine etc.) at a temperature of from 0° C. to 50° C., (ii) acid chloride corresponding to acid of the formula (V) with desired amine of the formula (IV) at a temperature of from −10° C. to 40° C. or (iii) acid of the formula (V) with oxalyl chloride followed by desired amine of the formula (IV) at a temperature of from −20° C. to 0° C. in an inert organic solvent (dimethylformamide (DMF)).

Step 4 are esterification. For example, it may be carried out by reacting:

(i) in an inert organic solvent (DMF etc.) in the presence of DCC or a tertiary amine (pyridine, triethylamine etc.), at a temperature of from 0° C. to 50° C., (ii) acid chloride corresponding to acid of the formula (VII) with desired alcohol of the formula (VI) in an inert organic solvent (DMF etc.), at a temperature of from −10° C. to 40° C., (iii) acid of the formula (VII) with oxalyl chloride followed by desired alcohol of the formula (VI) at a temperature of from −20° C. to 0° C. in an inert organic solvent (DMF etc.).

Starting material

The starting materials and each reagents of the formulae (II), (III), (IV), (V), (VI) and (VII) are known or may be prepared by the steps shown in scheme 1 to 12 described hereinafter.

Namely, among the compounds of the formula (II), (II)-1: the compounds (II)-1, wherein Ma and Za are bond and Wa is bond, C1-8 alkylene, C2-8 alkenylene or alkynylene, are known or may be prepared with using known compounds by known methods and (II)-2: the compounds (II)-2, wherein Za is —OCO—, may be prepared by the steps shown in scheme 1.

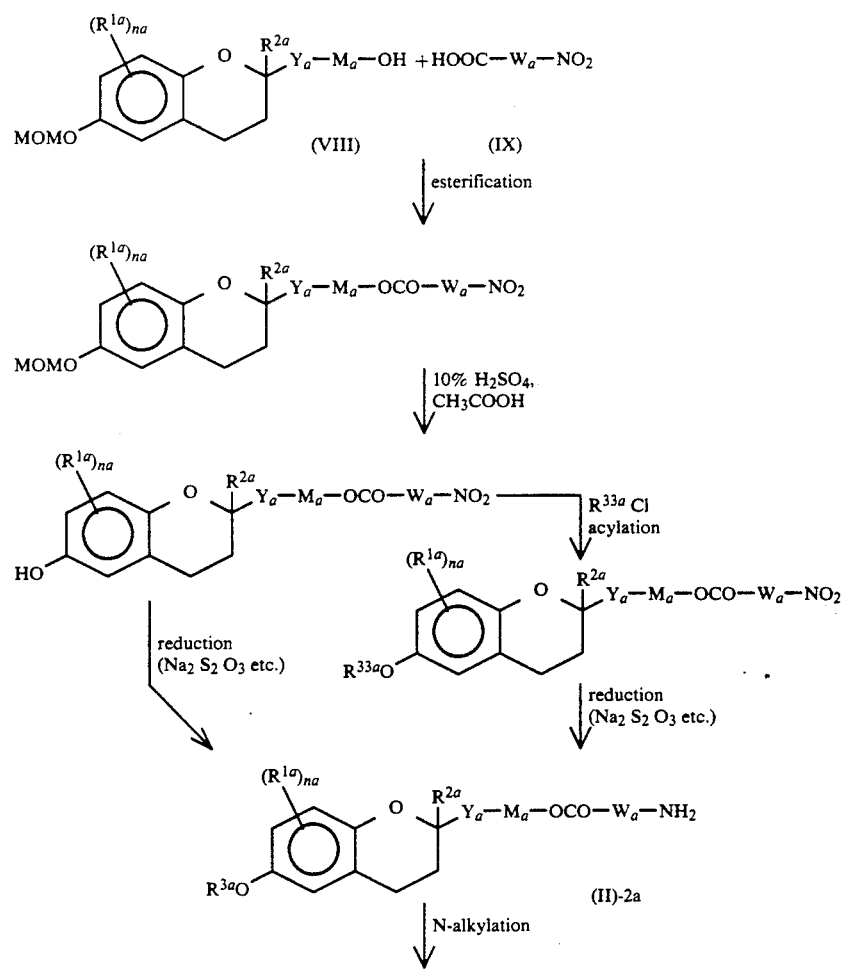

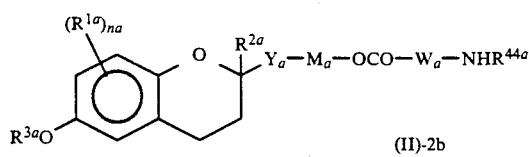
(II)-3: The compounds (II)-3, wherein Za is —NR$^{9a}$CO—, may be prepared by the steps shown in scheme 2.
(II)-4: The compounds (II)-4, wherein Za is —COO—, may be prepared by the steps shwon in scheme 3.
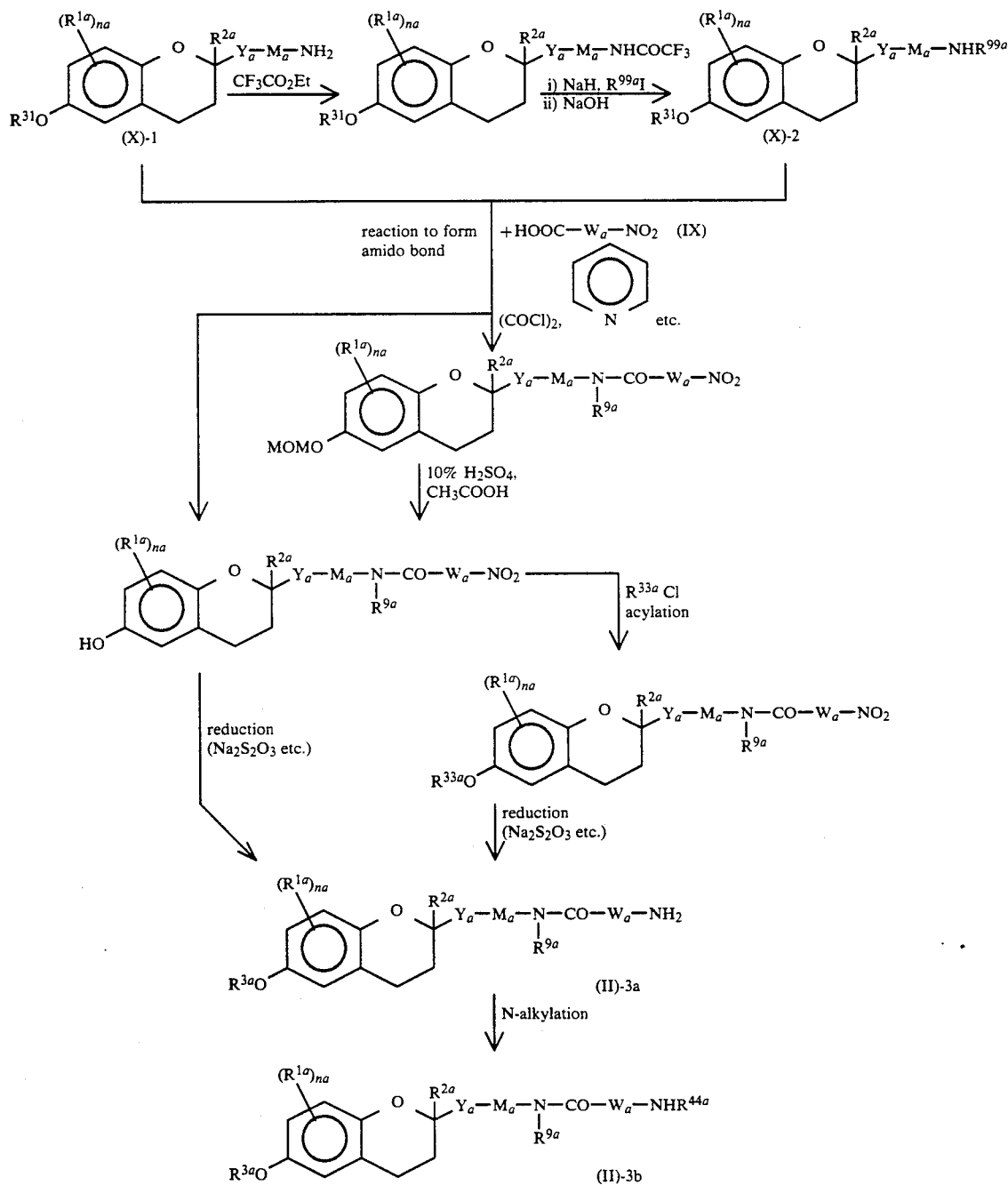

Scheme 3
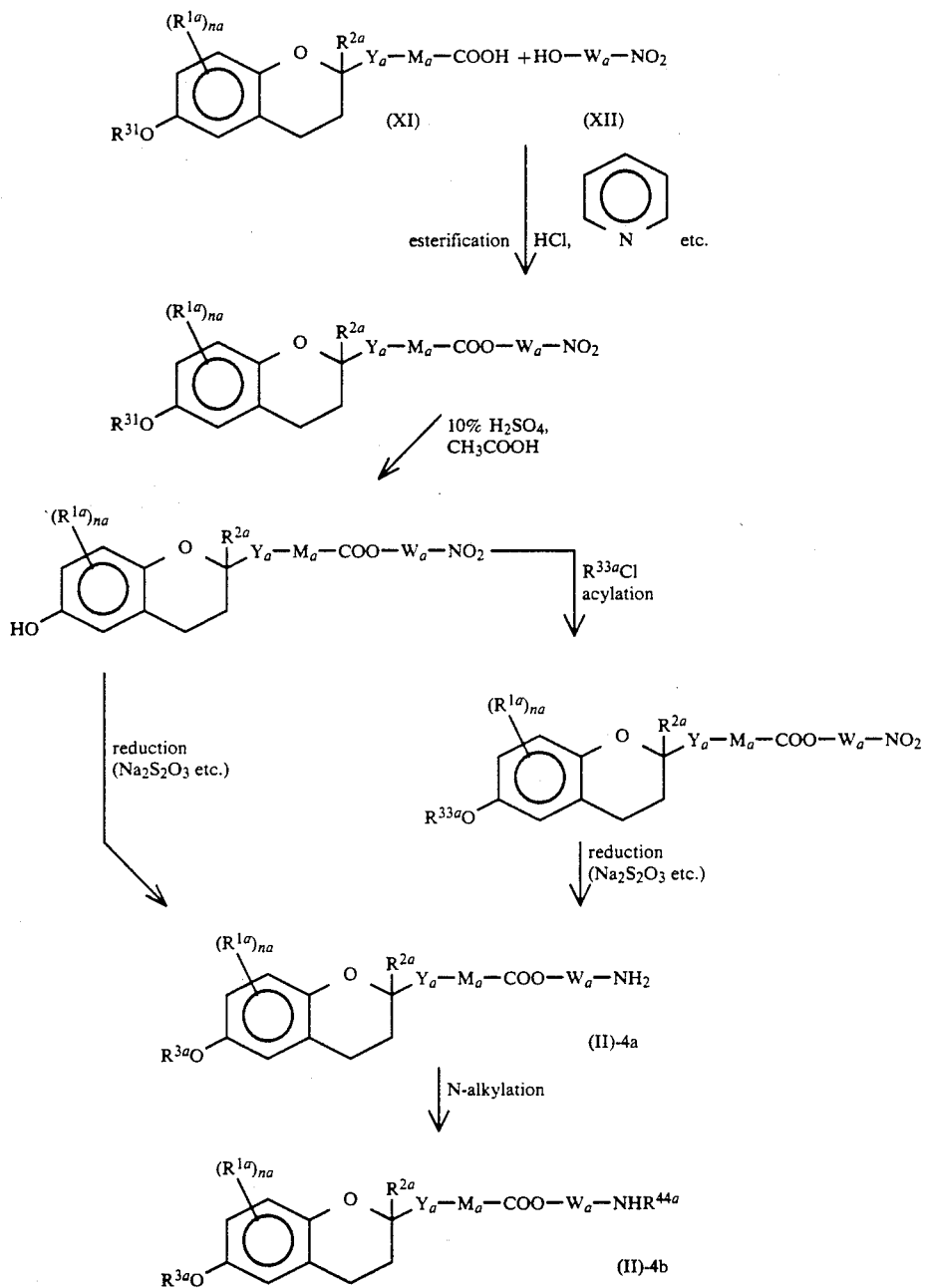
(II)-5: The compounds (II)-5, wherein Za is —CONR$^{55}$ $^{9a}$—, may be prepared by the steps shown in scheme 4.
Scheme 4
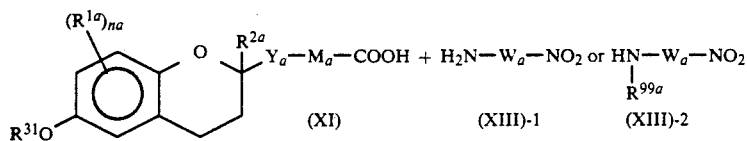

-continued
Scheme 4
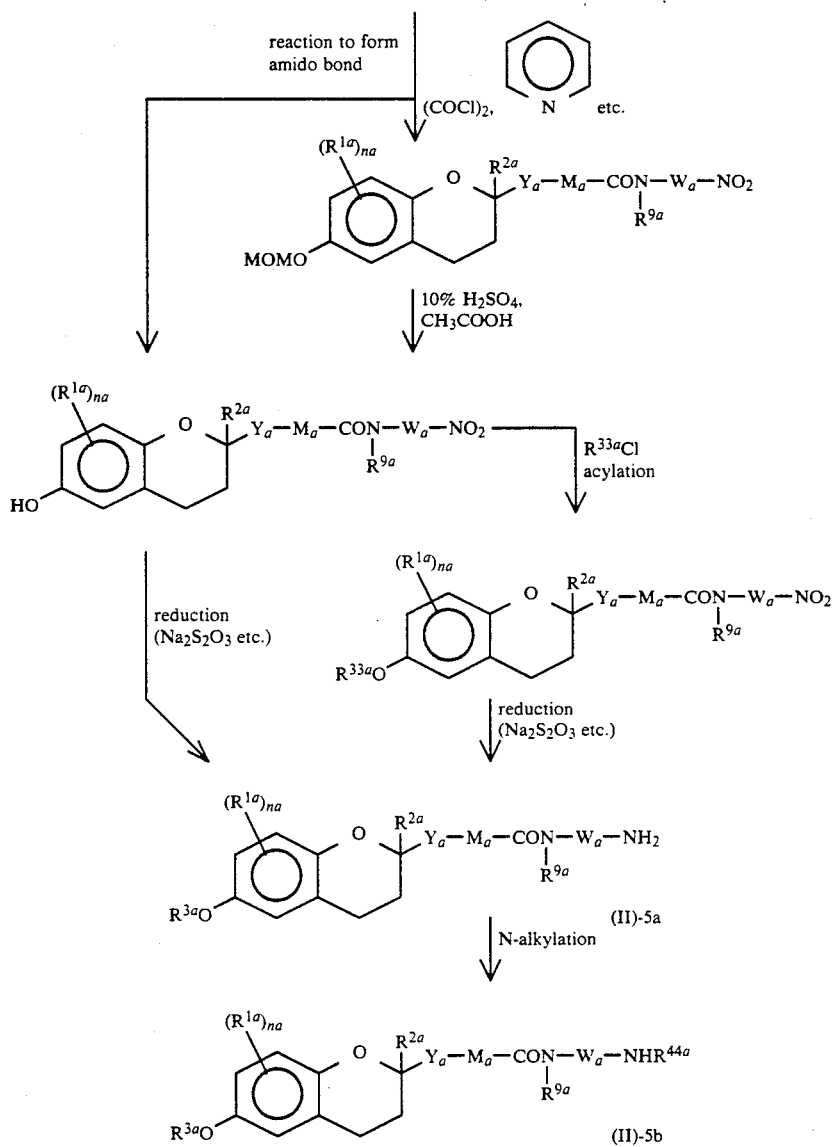
(II)-6: The compounds (II)-6, wherein Za is —O—, may be prepared by the steps shown in scheme 5 and 6.
Scheme 5
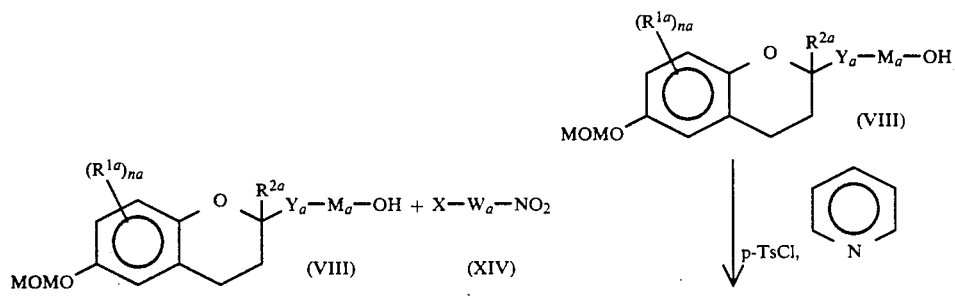

-continued
Scheme 5
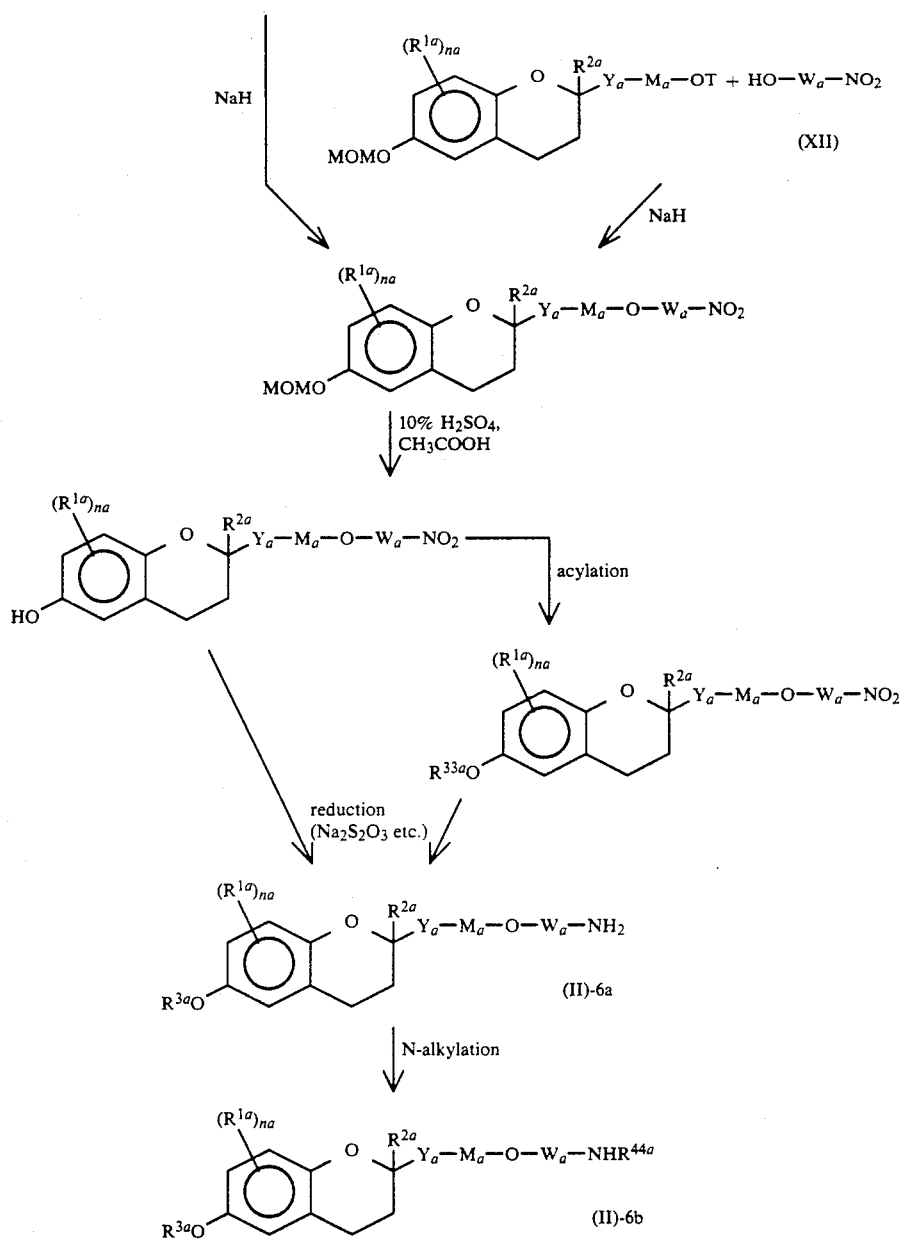
Scheme 6
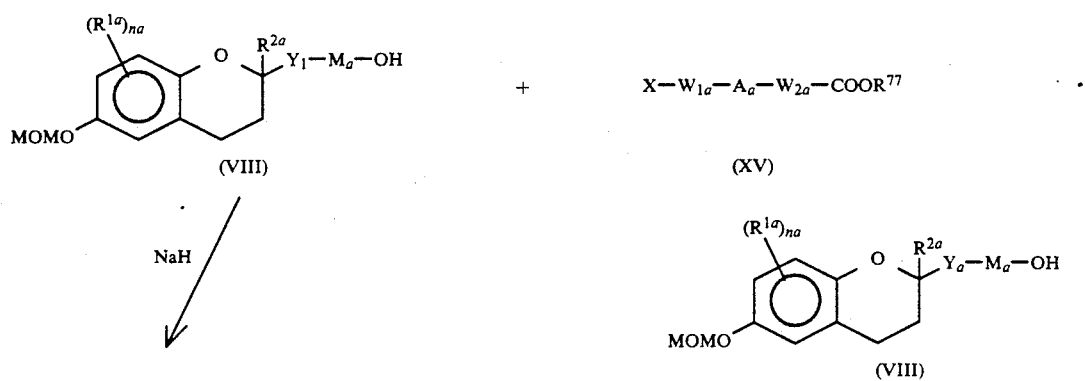

-continued
Scheme 6
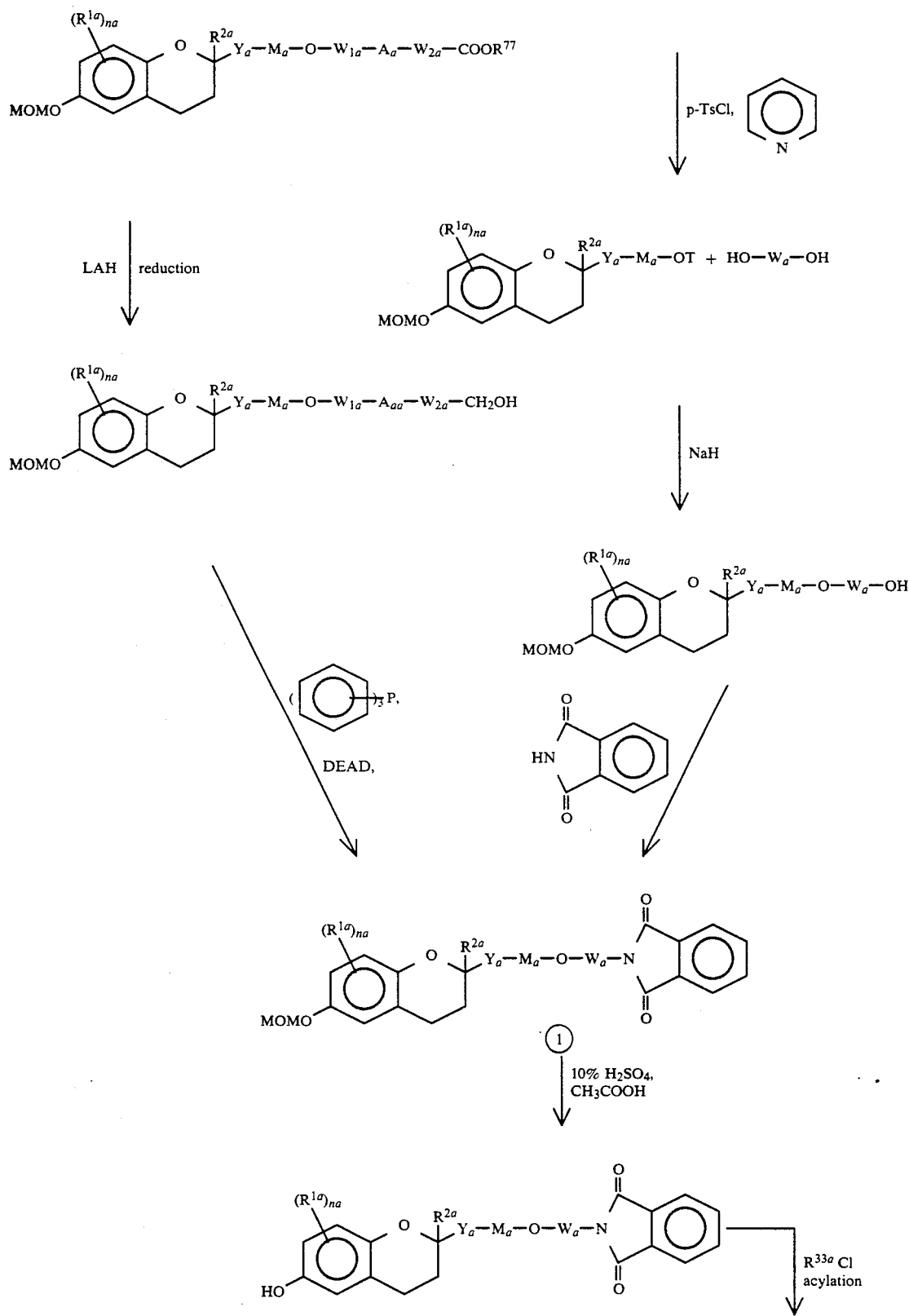

-continued
Scheme 6
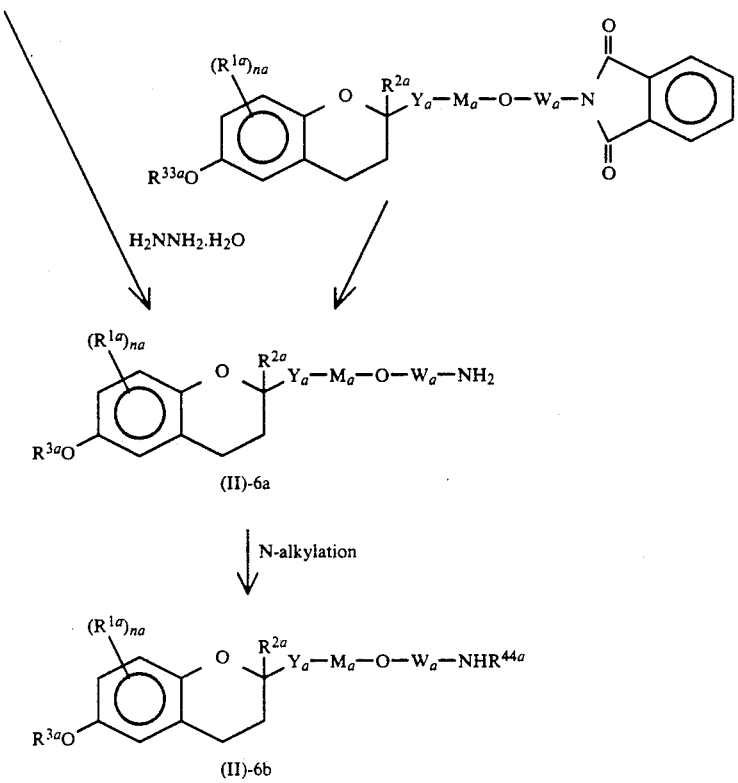
(II)-7: The compounds (II)-7, wherein Za is —NH-CONH—, may be prepared by the steps shown in scheme 7-1.
Scheme 7-1
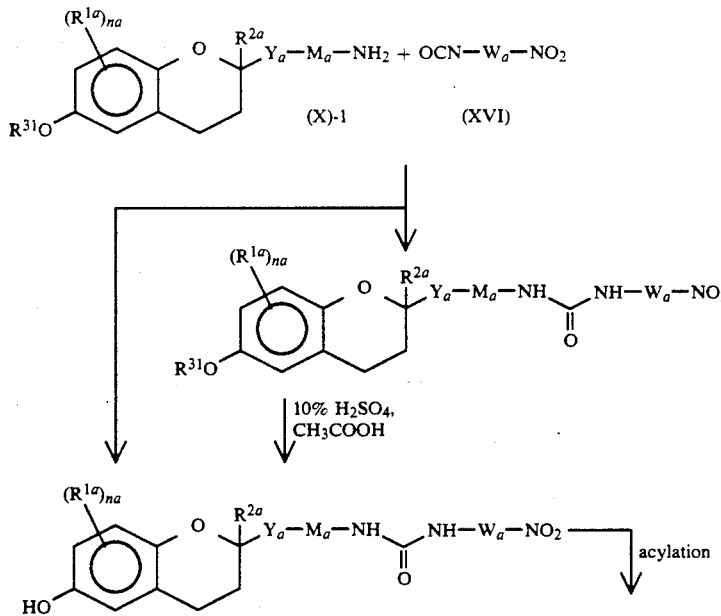

-continued
Scheme 7-1
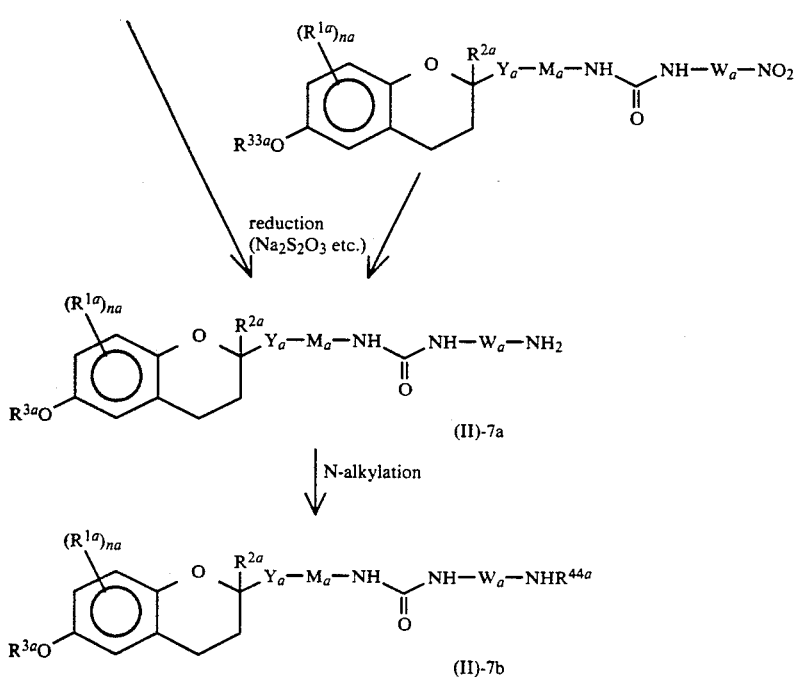
(II)-8: The compounds (II)-8, wherein Za is bond; Ma is a group of the formula: —Da—Ba—; and Aa is a group of the formula:
may be prepared by the steps shown in scheme 7-2.
Scheme 7-2
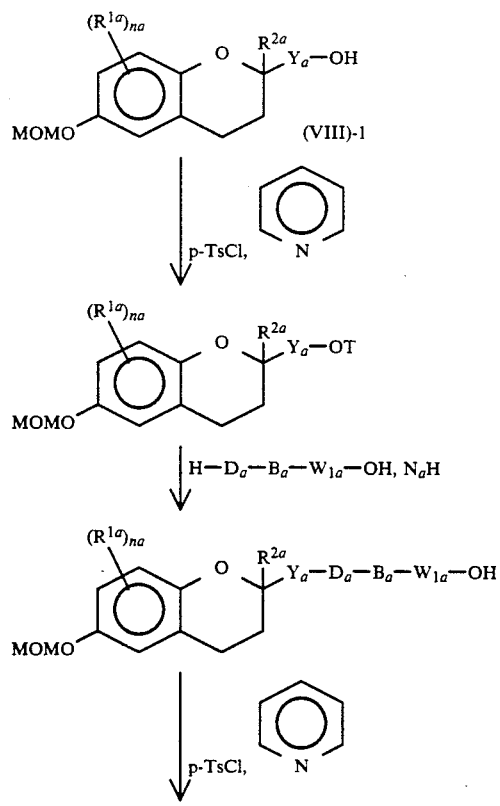

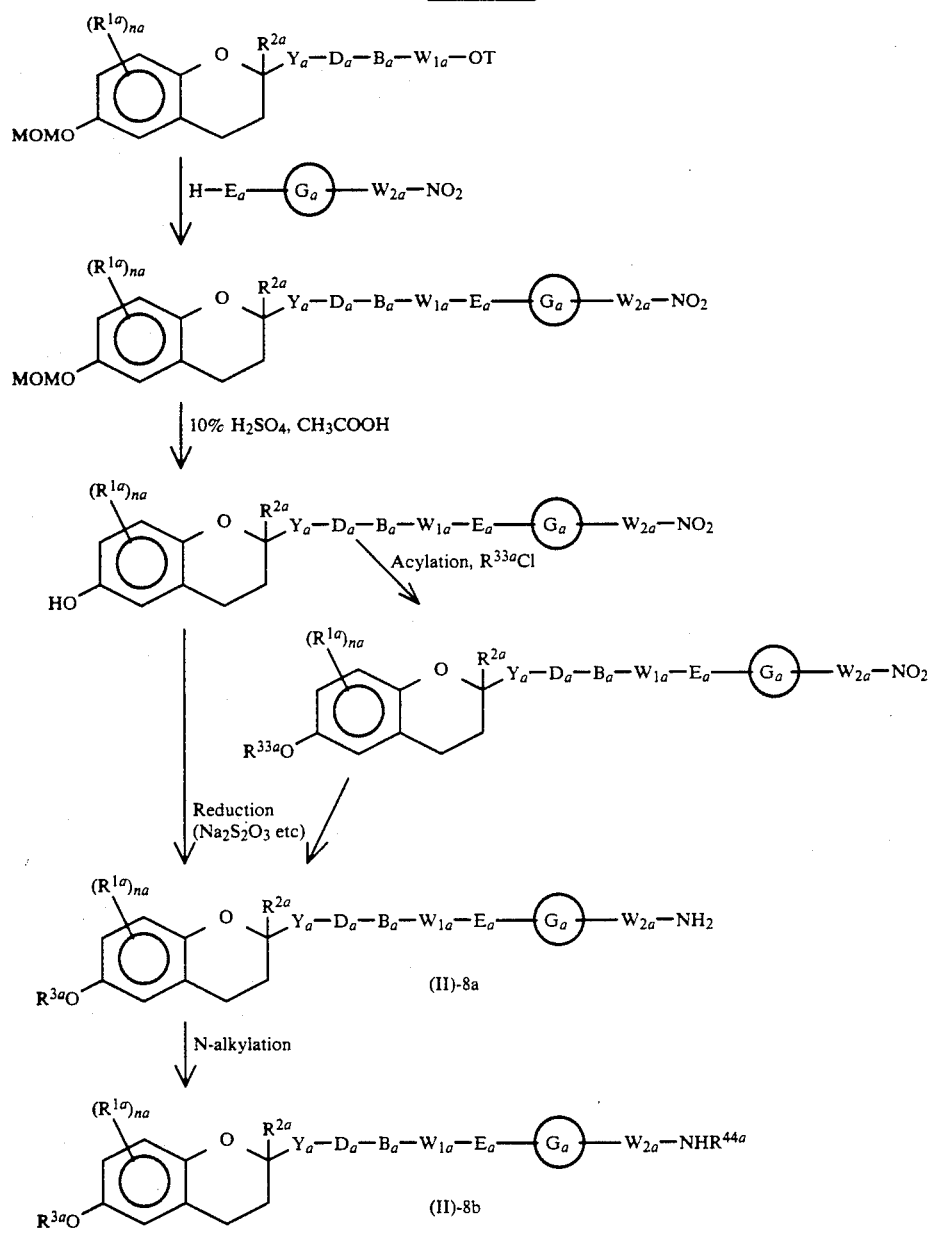
The compounds of the formula (III) may be prepared from the compounds of the formula (II) by the steps shown in scheme 8.
Scheme 8
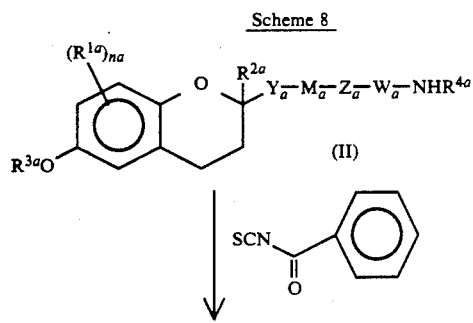
-continued
Scheme 8
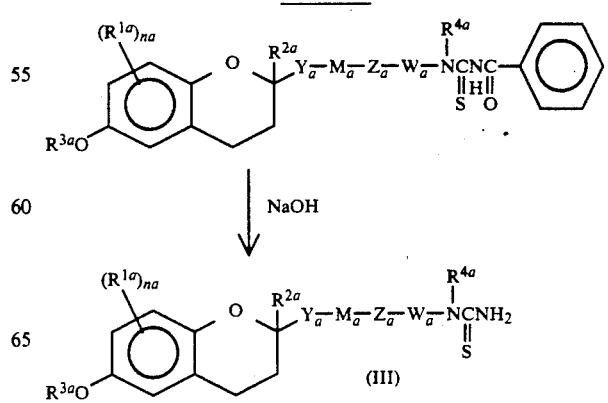

Among the compounds of the formula (IV), (IV)-1: the compounds (IV)-1a, wherein Ma is bond and $R^{9a}$ is hydrogen, are known or may be prepared with using known compounds by known methods and the compounds (IV)-1b, wherein Ma is bond and $R^{9a}$ is C1-4 alkyl or benzyl, may be prepared by the steps shown in scheme 9-1.

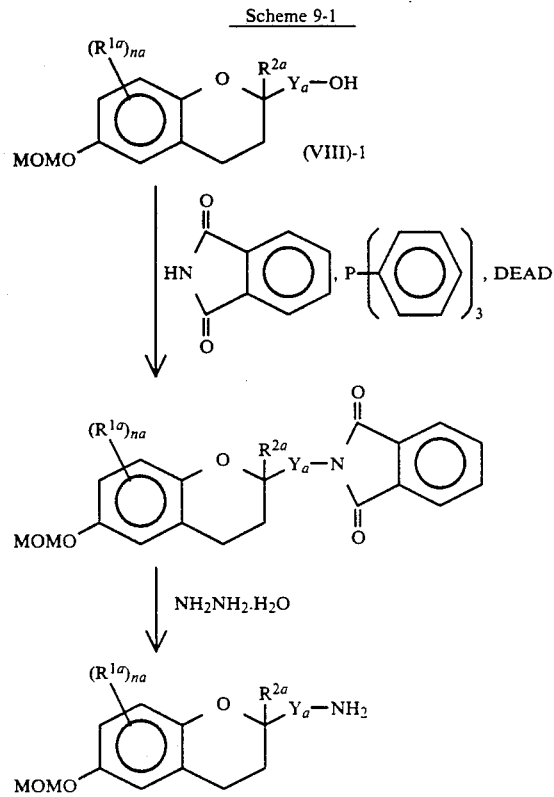

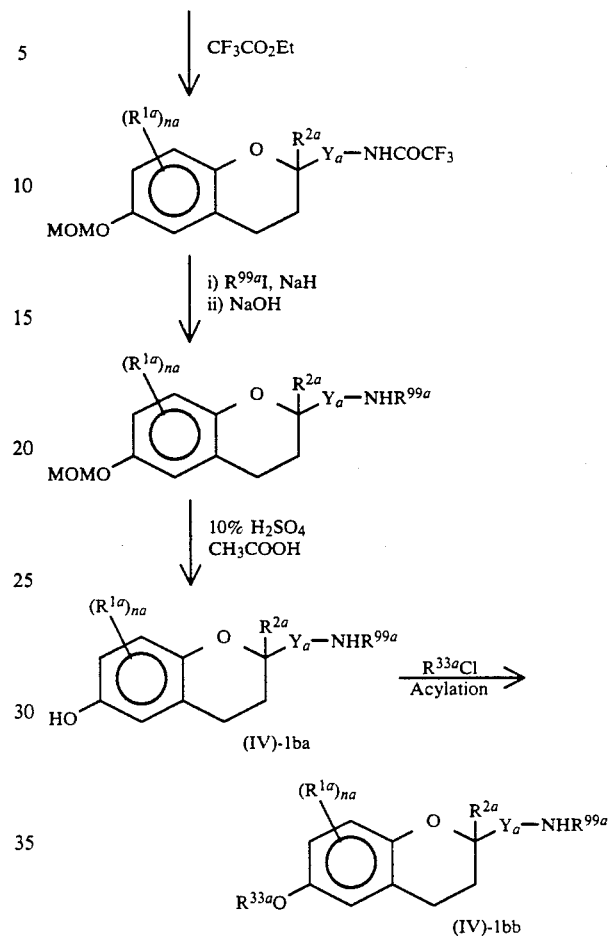

(IV)-2: The compounds (IV)-2, Ma is a group of the formula: —Da—Ba—, may be prepared by the steps shown in scheme 9-2.

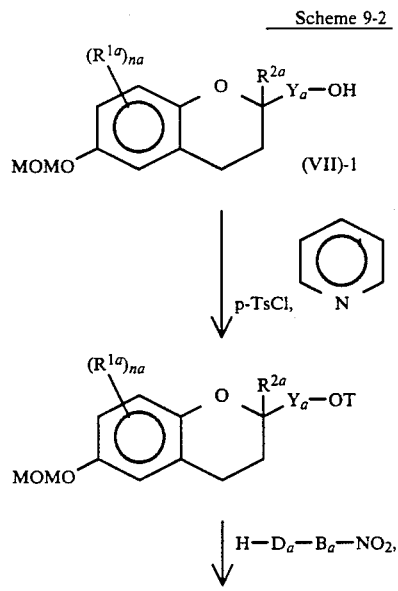

-continued
Scheme 9-2

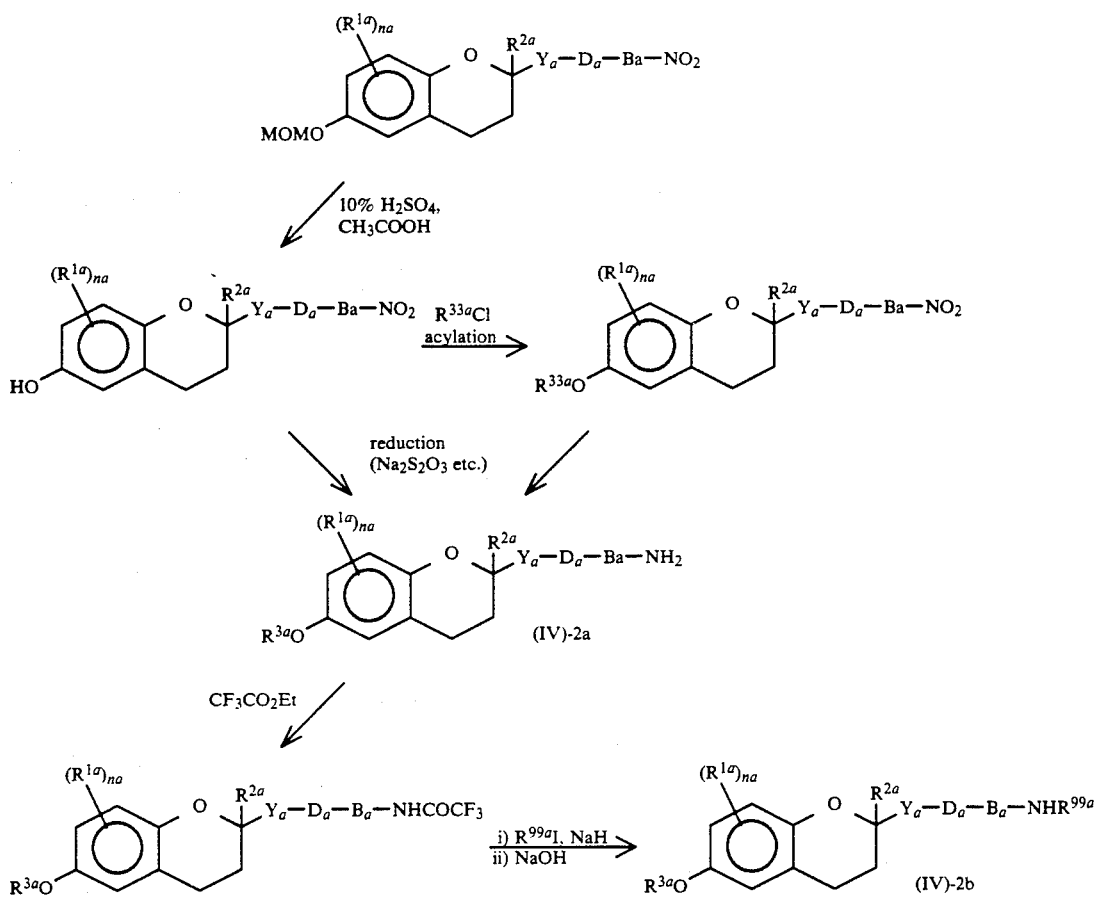

The compounds of the formula (V) are known or may be prepared with using known compounds by known methods.

Among the compounds of the formula (VI), (VI)-1: the compounds (VI)-1, wherein Ma is bond, are known or may be prepared with using known compounds by known methods.

(VI)-2: the compounds (VI)-2, wherein Ma is a group of the formula: —Da—Ba—, are prepared by the steps shown in scheme 10.

Scheme 10

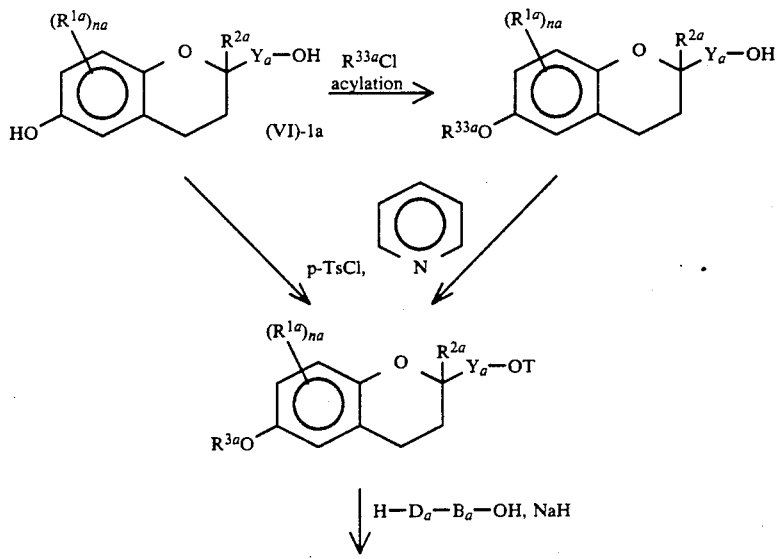

Scheme 10

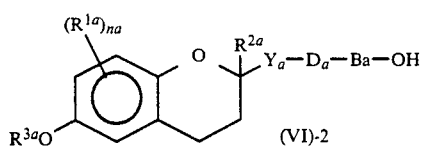

The compounds of the formula (VII) are known or may be prepared with using known compounds by known methods.

Among the compounds of the formula (VIII),
(VIII)-1: the compounds (VIII)-1, wherein Ma is bond, are known or may be prepared with using known compounds by known methods and
(VIII)-2: the compounds (VIII)-2, wherein Ma is a group of the formula: —Da—Ba—, may be prepared with using CH$_3$OCH$_2$Cl instead of R$^{33a}$Cl used as acylation reagent.

The compounds of the formula (IX) are known or may be prepared with using known compounds by known methods.

Among the compounds of the formula (X),
(X)-1: the compounds (X)-1, wherein Ma is bond, are known or may be prepared with using known compounds by known methods and
(X)-2 the compounds (X)-2, wherein Ma is a group of the formula: —Da—Ba—, may be prepared by the steps shown in scheme 11.

Scheme 11

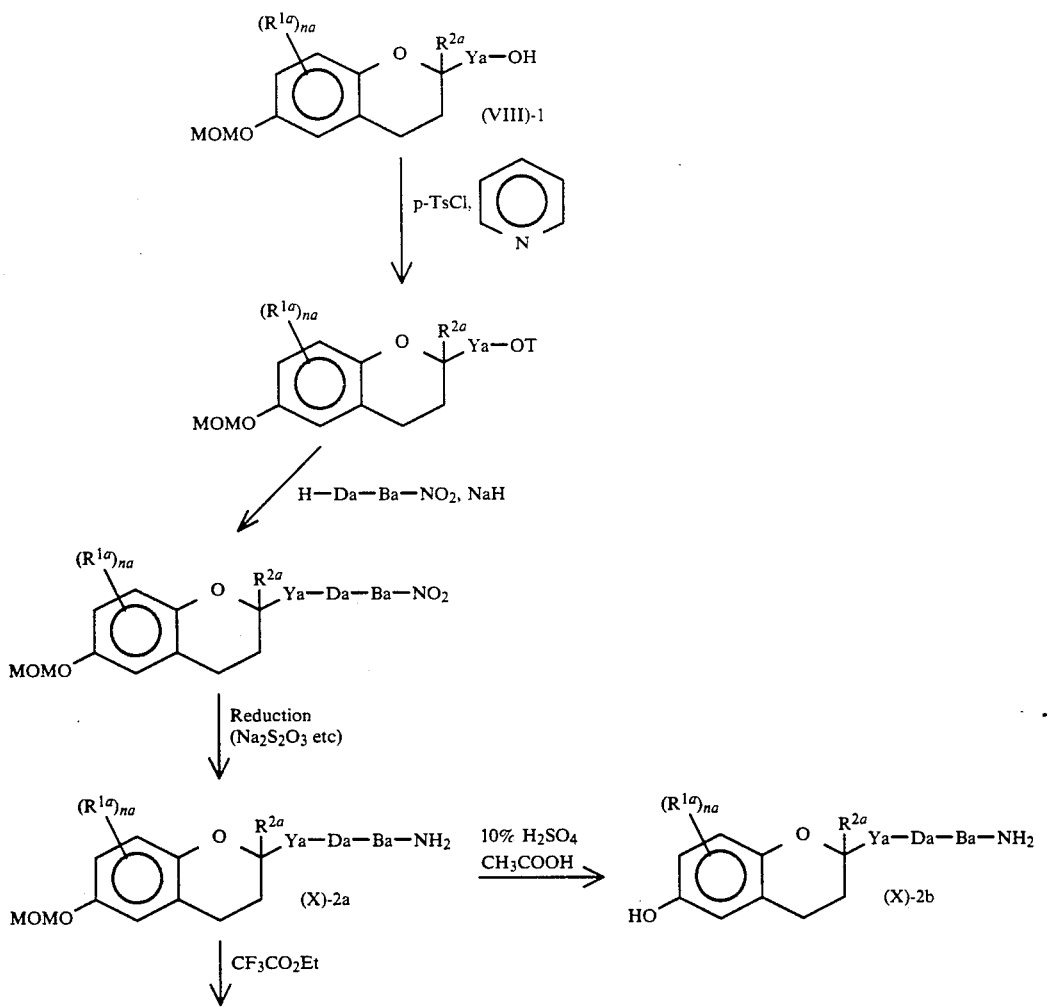

-continued
Scheme 11

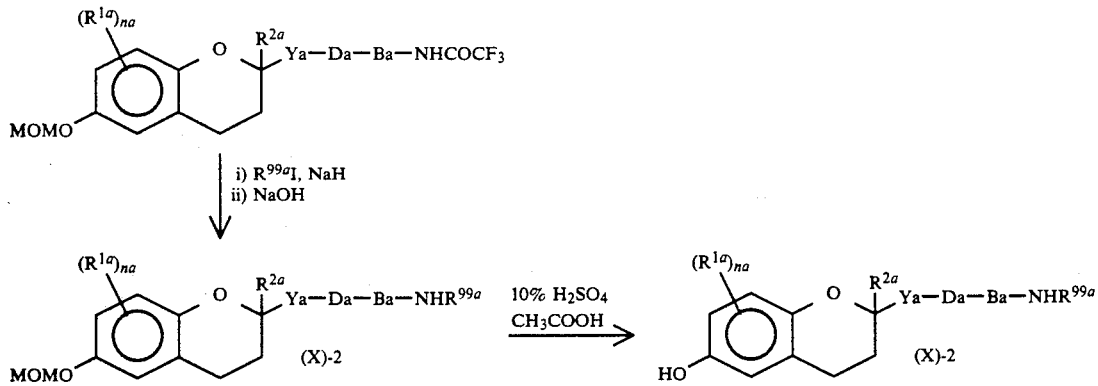

Among the compounds of the formula (XI),
(XI)-1: the compounds (XI)-1, wherein Ma is bond, are known or may be prepared with using known compounds by known methods and
(XI)-2: the compounds (XI)-2, wherein Ma is a group of the formula: —Da—Ba—, may be prepared by the steps shown in scheme 12.

Scheme 12

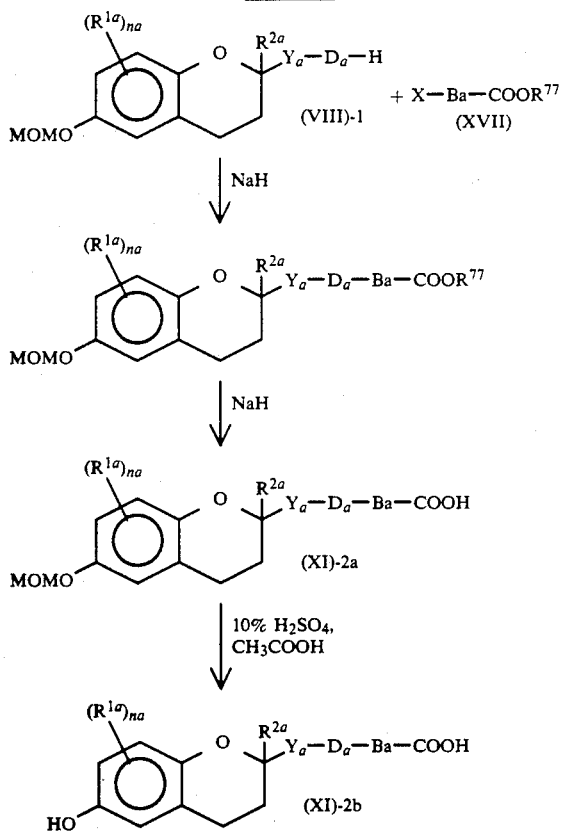

The compounds of the formulae (XII), (XIII), (XIV), (XV), (XVI) and (XVII) are known or may be prepared with using known compounds by known methods.

In the scheme 1 to 12 described hereinbefore.
$R^{33a}$ is C2–4 acyl or benzoyl;
$R^{44a}$ is C1–4 alkyl;
$R^{31}O$ is hydroxy or methoxymethoxy;
MOMO is methoxymethoxy;
p-TsCl is p-toluenesulfonyl chloride;
T is tosyl;
$R^{77}$ is methyl or ethyl;
Aaa is
  i) bond or
  ii) a group of the formula:

$$-Eaa-\boxed{Gaa}-;$$

Eaa is
  i) bond,
  ii) —O— or
  iii) —S—;

C4–10 carbocyclic or heterocyclic ring; or C4–10 carbocyclic or heterocyclic ring substituted by one to three C1–4 alkyl, C1–4 alkoxy, halogen, trihalomethyl or acetamido;
DEAD is diethyl azodicarboxylate; and
the other symbols are the same meanings described hereinbefore.

The reaction products may be purified by conventional methods, for example, distillation at atmospheric or reduced pressure, high performance liquid chromatography, thin layer chromatography or column chromatography using silica gel or magnesium silicate or washing or recrystallization. Purification may be carried out after each reactions or a series of reactions.

Effect

The inhibitory activity on Maillard reaction of the compounds of the present invention has confirmed by the screening system mentioned below.

(1) Method of experiment

Lysozyme (10 mg/ml) and fructose (100 mM) were dissolved in 0.2M sodium phosphatic buffer solution (PH 7.4). The solution was incubated at a temperature of 37° C. for 3 days. A given volume of the reaction solution was separated using SDS-PAGE by the electrophoresis. After the electrophoresis, the SDS-PAGE was dyed by 0.2% Coomassie Brilliant Blue R-250 and then the dimer was determined by densitometer.

The compounds of the present invention were added before incubation and the inhibitory activity of them against the formation of the dimer was examined in various concentrations and $IC_{50}$ values were calculated.

(2) The results are shown in the following table 1.

| Ex. No. | IC$_{50}$ value (mM) |
| --- | --- |
| 1 (a) | 0.20 |
| 1 (d) | 0.34 |
| 1 (e) | 0.050 |
| 1 (h) | 0.053 |
| 1 (i) | 0.10 |
| 1 (j) | 0.060 |
| 1 (m) | 0.44 |
| 2 | 0.45 |
| 2 (e) | 0.19 |
| 2 (f) | 0.15 |
| 3 | 0.36 |
| 4 | 0.15 |
| 5 | 0.32 |
| 5 (b) | 0.074 |
| 5 (c) | 0.50 |
| 5 (f) | 0.022 |
| 7 (a) | 0.20 |
| 7 (b) | 0.012 |
| 7 (c) | 0.0048 |
| 7 (d) | 0.048 |
| 7 (e) | 0.030 |
| 7 (f) | 0.018 |
| 7 (h) | 0.019 |
| 7 (k) | 0.012 |
| 7 (l) | 0.054 |
| 7 (m) | 0.012 |
| 7 (n) | 0.010 |
| 7 (t) | 0.017 |
| 8 | 0.30 |
| 9 | 0.0062 |
| 9 (a) | 0.010 |
| 9 (d) | 0.0054 |
| 9 (j) | 0.0048 |
| 9 (l) | 0.0066 |
| 9 (m) | 0.009 |
| 10 | 0.075 |
| 10 (a) | 0.021 |
| 10 (e) | 0.036 |
| 12 | 0.20 |
| 14 | 0.22 |
| 15 | 0.22 |
| 17 | 0.013 |
| 19 | 0.056 |
| 21 | 0.22 |
| 22 | 0.048 |
| 22 (a) | 0.50 |
| 23 | 0.13 |
| 24 | 0.18 |
| 24 (a) | 0.068 |
| 26 | 0.27 |
| 27 | 0.0058 |
| 27 (b) | 0.19 |
| 27 (f) | 0.0056 |
| 28 (c) | 0.0042 |
| 29 | 0.0075 |
| 29 (a) | 0.020 |

The antioxiding effect of the compounds of the present invention has confirmed by the screening system which examines inhibitory activity against formation of peroxidized fat mentioned below.

(1) Method of experiment

Male Sprague Dawley rat was fasted for 12 hrs (overnight) before experiments, and was anesthetized with ether. Rat liver was perfused with ice-cold 0.9% NaCl via the portal vein, and promptly excised. 10% Liver homogenates were prepared in ice-cold 1.15% KCl. The reaction was started by adding 200 µM FeCl$_2$ to the liver homogenate (0.2 µl), and incubated at 37° C. for 1 hr. Lipid peroxide was measured by the TBA method according to the method of Ohkawa (See Analytical Biochemistry, 95, 351 (1979)).

The compounds of the present invention were added before incubation. And the efficacy thereof was examined and calculated IC$_{50}$ values thereof.

(2) The results are shown in the following Table 2.

| Ex. No. | IC$_{50}$ (µM) |
| --- | --- |
| 1 | 0.60 |
| 1 (a) | 0.54 |
| 1 (b) | 0.78 |
| 1 (c) | 0.80 |
| 1 (e) | 0.16 |
| 1 (f) | 0.82 |
| 1 (g) | 0.90 |
| 1 (h) | 0.90 |
| 1 (j) | 0.46 |
| 1 (k) | 0.44 |
| 1 (l) | 0.38 |
| 1 (m) | 0.60 |
| 2 | 0.66 |
| 2 (a) | 0.78 |
| 2 (b) | 0.47 |
| 2 (c) | 0.50 |
| 3 | 0.54 |

The results in the Table 1 and Table 2 show that the compounds of the present invention and acid addition salts thereof possess an inhibitory effect on Maillard reaction and an antioxiding effect.

The compounds of the formulae (IA) and (IB), of the present invention, and pharmaceutically acceptable acid addition salts thereof possess the inhibitory activity on Maillard reaction. Accordingly, the compounds of the present invention are useful for treatment and/or prevention of several diabetic complication, i.e. coronary heart disease, peripheral circulatory insufficiency or failure, cerebrovascular hindrance, neurogenous diabetes, nephropathy, arteriosclerosis, arthrosclerosis, cataracta and retinopathy, and the diseases induced by aging, i.e. atherosclerosis, senile cataract and cancer.

Moreover, the compounds of the formulae (IA) and (IB), of the present invention and pharmaceutically acceptable acid addition salts thereof possess an antioxidizing effect, that is, an inhibitory effect on reaction by free radical. Accordingly, the compounds are useful for treatment and/or prevention of several diseases caused by formation of peroxidized fat, i.e. arteriosclerosis, glycosuria, myocardial infarction, peripheral circulatory disorders, cerebrovascular disease, cancer, inflammation, digestive diseases and aging.

Toxicity

It was confirmed that the toxicity of the compounds of the present invention were very low. Accordingly, it was confirmed that the compounds of the present invention were useful for prevention and/or treatment for deseases attributed to Maillard reaction, in animals including human beings, especially human beings.

Administration

For the purpose above described, the compounds of the present invention of the formulae (IA) and (IB) and pharmaceutically acceptable acid addition salts thereof may be normally administered systemically or partically, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration up to several times per day, and are generally between 0.1 mg and 100 mg, by parenteral administration (preferably, intravenous administration) up to several times per day.

As mentioned above, the doses to be used depend upon various conditions. Therefore, there are cases in which doses lower than or greater than the ranges specified above may be used.

In administration of the compounds of the present invention, solid composition, liquid composition and other composition are used for oral administration, and injections, medicines for external use and suppositories are used for parenteral administration.

Solid compositions for oral administration include compressed tablets, pills, capsules, dispersible powders, and granules. Capsules contain hard capsules and soft capsules.

In such compositions, one or more of the active compound(s) is or are, admixed with at least one inert diluent (lactose, mannitol, glucose, hydroxypropyl cellulose, microcrystalline cellulose, starch, polyvinylpyrrolidone, magnesium metasilicate aluminate etc.). The compositions may also comprise, as is normal practice, additional substances other than inert diluents: e.g. lubricating agents (magnesium stearate etc.), disintegrating agents (cellulose calcium glycolate etc.), stabilizing agent (lactose etc.), and assisting agent for dissolving (glutamic acid, asparaginic acid etc.).

The tablets or pills may, if desired, be coated with film of gastric or enteric material (sugar, gelatin, hydroxypropyl cellulose or hydroxypropylmethyl cellulose phthalate etc.), or be coated with more than two films. And further, it may be include capsules of absorbable materials such as gelatin.

Liquid compositions for oral administration include pharmaceutically-acceptable solutions, emulsions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (wetting agents, suspending agent etc.), sweetening agents, flavouring agents, perfuming agents and preserving agent.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.)

For preparation of such spray compositions, for example, the method described in the U.S. Pat. No. 2,868,691 or 3,095,355 may be used.

Injections for parenteral administration include sterile aqueous or non-aqueous solutions, suspensions and emulsions. In such compositions, one more of active compound(s) is or are admixed at least one of inert aqueous diluent(s) (distilled water for injection, physiological salt solution etc.) or inert non-aqueous diluent(s) (propylene glycol, polyethylene glycol, olive oil, ethanol, POLYSOLBATE 80 (registered trade mark) etc.).

Injections may comprise additional other than inert diluents: e.g. preserving agents, wetting agents, emulsifying agents, dispersing agents, stabilizing agent (lactose etc.), assisting agents such as assisting agents for dissolving (glutamic acid, asparaginic acid etc.).

They may be sterilized for example, by filtration through a bacteria-retaining filter, by incorporation of sterilizing agents in the compositions or by irradiation. They also be manufactures in the form of sterile solid compositions, for example, by freeze-drying, and which can be dissolved in sterile water or some other sterile diluents for injection immediately before used.

Other compositions for parenteral administration include liquids for external use, and endermic liniments (ointment etc.), suppositories and pessaries which comprise one or more of the active compound(s) and may be prepared by known methods.

REFERENCE EXAMPLE AND EXAMPLE

The following reference examples and examples illustrate the compounds of the present invention and the process for the preparation of them, but not limit the present invention.

The solvents in the parentheses show the developing or eluting solvents and the rations of the solvents used are by volume in chromatographic separations. "IR" were measured by KBr tablet method.

REFERENCE EXAMPLE 1

2-(6-hydroxy-2,5,7,8-tetramethyl-3,4-dihydro-2H-benzo[1,2-b]pyran-2-yl)ethanol

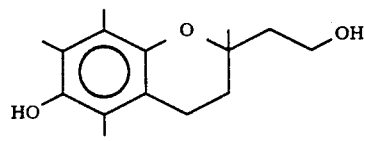

Lithium aluminum hydride (LAH) (8.0 g) was suspended in ether (500 ml). A solution of methyl 2-(6-acetoxy-2,5,7,8-tetramethyl-3,4-dihydro-2H-benzo[1,2-b]pyran-2-yl)acetate (12.16 g) in ether (200 ml) was added dropwise to the suspension. The mixture was stirred for 1 hour. A saturated aqueous solution of sodium sulfate was added dropwise to the reaction solution at room temperature to decompose excess LAH. The solution was filtered. The filtrate was evaporated to give the title compound (9.31 g) having the following physical data.

TLC (ethyl acetate:hexane=2:1): Rf 0.43.

REFERENCE EXAMPLE 2

N-[2-(6-hydroxy-2,5,7,8-tetramethyl-3,4-dihydro-2H-benzo[1,2-b]pyran-2-yl)ethyl]phthalimide

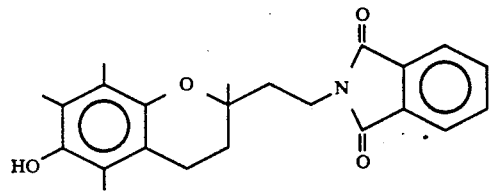

Diethyl azodicarboxylate (3.36 ml) was added dropwise to a solution of the alcohol (prepared in reference example 1, 4.69 g) and phthalimide (3.14 g) in anhydrous tetrahydrofuran (80 ml) at a temperature of 0° C. The temperature of the solution was raised to room temperature. The solution was stirred at 2 hours. Water was added to the solution. the solution was extracted with ethyl acetate. The extract was washed with a saturated brine, dried over magnesium sulfate and then evaporated. The residue was purified by column chromatography on silica gel (hexane:ethyl acetate=3:1) to give the title compound (6.8 g) having the following physical data.

TLC (ethyl acetate:hexane=2:1): Rf 0.54.

REFERENCE EXAMPLE 3

2-(2-aminoethyl)-2,5,7,8-tetramethyl-6-hydroxy-3,4-dihydro-2H-benzo[1,2-b]pyran

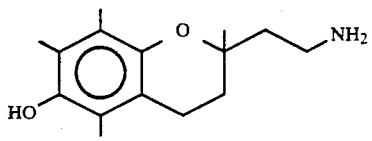

Imide (prepared in reference example 2, 450 mg) was suspended in ethanol (7 ml). 80% hydrazine hydride (1 ml) was added dropwise to the suspension at room temperature. The mixture was stirred for 1 hour.

The reaction solution was evaporated. Ethyl acetate was added to the residue. The solution was filtered to remove white crystal precipitated. The filtrate was evaporated. The residue was purified by column chromatography on silica gel (methylene chloride:ethanol=15:1→10:1) to give the title compound (220 mg) having the following physical data.

TLC (ethyl acetate:acetic acid:water=3:1:1): Rf 0.51.

REFERENCE EXAMPLE 4

1-[2-(6-hydroxy-2,5,7,8-tetramethyl-3,4-dihydro-2H-benzo[1,2-b]pyran-2-yl)ethyl]-3-benzoylthiourea

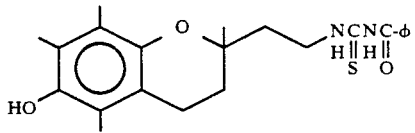

A solution of benzoylisothiocyanate (28.0 g) in acetone (200 ml) was added dropwise to a solution of amine (prepared in reference example 3, 34.3 g) in acetone (800 ml). The solution was stirred for 15 hours at room temperature. The reaction solution was evaporated. The residue was purified by column chromatography on silica gel (hexane:ethyl acetate=10:1→4:1→2:1) to give the title compound (32.0 g) having the following physical data.

TLC (n-hexane:ethyl acetate=4:1): Rf 0.23.

REFERENCE EXAMPLE 5

1-[2-(6-hydroxy-2,5,7,8-tetramethyl-3,4-dihydro-2H-benzo[1,2-b]pyran-2-yl)ethyl]thiourea

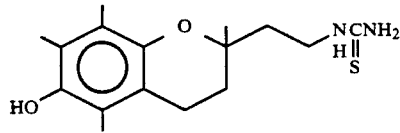

The thiourea compound (prepared in reference example 4, 32.0 g) was dissolved in ethanol (310 ml). A 2N aqueous solution of sodium hydroxide (155 ml) was added to the solution. The mixture was stirred for 1 hour at room temperature and then for 1 hour at a temperature of 50° C. on water bath. After confirmation of conclusion of the reaction, the reaction solution was diluted with water. The solution was extracted with ethyl acetate (1 liter) followed by ethyl acetate (200 ml×5). The extract was washed with water two times followed by a saturated brine, dried over magnesium sulfate and then evaporated. The residue was purified by column chromatography on silica gel (chloroform:methanol=98:2→95:5) to give the title compound (17.4 g) having the following physical data.

TLC (chloroform:methanol=9:1): Rf 0.29.

REFERENCE EXAMPLE 6

2-(6-hydroxy-2,5,7,8-tetramethyl-3,4-dihydro-2H-benzo[1,2-b]pyran-2yl)ethyl 4-hydroxymethylbenzyl ether

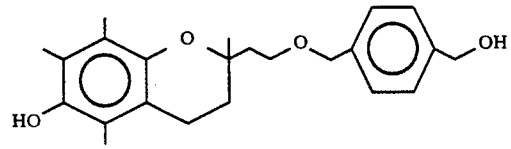

Alcohol (prepared in reference example 1, 1.25 g) was dissolved in dimethylformamide (20 ml). 62% Sodium hydride (0.24 g) was added to the solution. The solution was stirred for 1 hour at room temperature. A solution of methyl 4-bromomethylbenzoate (1.14 g) in dimethylformamide (10 ml) was added to the solution. The solution was stirred for 15 hours at room temperature. The reaction solution was stirred for 1.5 hours at a temperature of 60° C. Water was added to the reaction solution. The solution was extracted with ethyl acetate. The extract was washed with a saturated brine, dried over magnesium sulfate and evaporated. The residue was dissolved in ether (10 ml). The solution was reacted by the same procedure as reference example 1. The residue was purified by column chromatography on silica gel (n-hexane:ethyl acetate=2:1) to give the title compound (147 mg) having the following physical data.

TLC (n-hexane:ethyl acetate=1:1): Rf 0.63.

REFERENCE EXAMPLE 7

2-(6-methoxymethoxy-2,5,7,8-tetramethyl-3,4-dihydro-2H-benzo[1,2-b]pyran-2-yl)ethanol

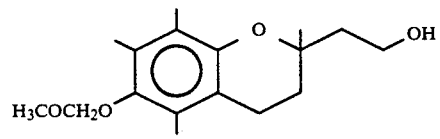

A solution of alcohol (prepared in reference example 1, 130 g) in dimethylformamide (1.2 liters) was added to sodium hydride (21.2 g) with cooling in an ice-bath. The solution was stirred for 40 mins at room temperature. The solution was cooled in an ice-bath once more. Chloromethyl methyl ether (40 ml) was added to the cooled solution. The solution was stirred for 25 mins at room temperature. Moreover, chloromethyl methyl ether (3.0 ml) was added to the solution. The solution was stirred for 5 mins and then poured into water (1.5 liters). The mixture was extracted with a mixed solution (1 liter) of n-hexane and ether (1:1). The extract was washed with water, followed by a brine and dried over magnesium sulfate and then evaporated to give the residue (158.9 g) contained the title compound having the following physical data. The residue was used in next reaction without purification.

TLC (ethyl acetate:n-hexane=2:3): Rf 0.29.

REFERENCE EXAMPLE 8

4-nitrophenyl 2-(6-methoxymethoxy-2,5,7,8-tetramethyl-3,4-dihydro-2H-benzo[1,2-b]pyran-2-yl)ethyl ether

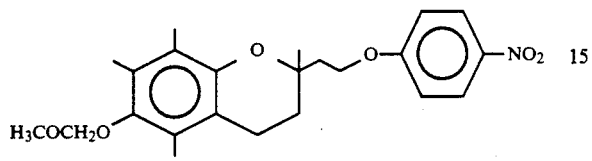

A solution of the residue (158.9 g) contained the methoxymethoxy compound, prepared in reference example 7 in dimethyl sulfoxide (1.1 liter) was added to sodium hydride (20.8 g). The mixture was vigorously stirred at 60° C. for one hour and then cooled. p-Chloronitrobenzene (81.8 g) was added to the mixture. The mixture was stirred at room temperature for 2 hours. The reaction mixture was poured into a mixture of ice (500 g) and water (1.5 liters). The mixture was extracted with a mixture solution (1 liter) of n-hexane-ether (1:1). The extract was washed with water, followed by brine, dried over mangesium sulfate and then evaporated. The residue was purified by column chromatography on silica gel (ethyl acetate: n-hexane=1:9→1:4→2:3) to give the title compound (157.3 g) having the following physical data.

TLC (ethyl acetate: n-HEXANE=2:3): Rf 0.56;
MS: m/e 415, 385, 370, 354, 231.

REFERENCE EXAMPLE 9

4-nitrophenyl 2-(6-hydroxy-2,5,7,8-tetramethyl-3,4-dihydro-2H-benzo[1,2-b]pyran-2-yl)ethyl ether

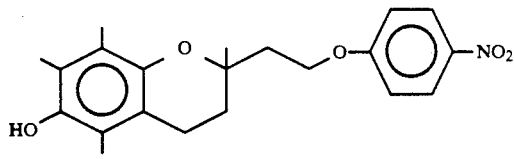

10% Sulfuric acid (38 g) was added to a solution of the ether (157.3 g) prepared in reference example 8 in acetic acid (600 ml). The solution was stirred at 60° C. for 20 minutes. The reaction mixture was cooled, poured into a mixture of sodium bicarbonate (1 kg) and ice (1 kg) and then left until foaming finished. The mixture was extracted with ethyl acetate (1 liter×2). The extract was washed with water, followed by brine, dried over magnesium sulfate and then evaporated to give the residue (142.7 g) contained the title compound having the following physical data. The residue was used in next reaction without purification.

TLC (ethyl acetate:n-hexane=2:3): Rf 0.45;
MS: m/e 371,232, 165.

REFERENCE EXAMPLE 10

4-aminophenyl 2-(6-hydroxy-2,5,7,8-tetramethyl-3,4-dihydro-2H-benzo[1,2-b]pyran-2-yl)ethyl ether

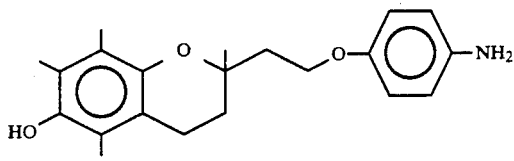

A solution of the residue (142.7 g) contained the ether compound, prepared in reference example 9 in a mixture solution of ethanol (900 ml) and ethyl acetate (150 ml) was added to 10% palladium-carbon (15 g). Addition of hydrogen gas to the solution was carried out all night. Catalyst was removed from the reaction mixture by filtration. The filtrate was evaporated. The residue was purified by column chromatography on silica gel (ethyl acetate:n-hexane=2:3) to give the title compound (120.6 g) having the following physical data.

TLC (ethyl acetate:n-hexane=2:3): Rf 0.17;
MS: m/e 341, 233, 205, 165.

REFERENCE EXAMPLE 11

2-(6-methoxymethoxy-2,5,7,8-tetramethyl-3,4-dihydro-2H-benzo[1,2-b]pyran-2-yl)acetoaldehyde

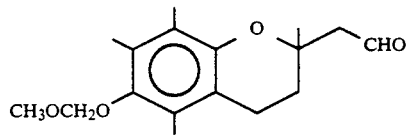

Oxalic chloride (2.27 ml) was dissolved in methylene chloride (30 ml). The solution was cooled to −60° C. A mixture of dimethylsulfoxide (3.69 ml) and methylene chloride (5 ml) was slowly added dropwise to the solution. The mixture was stirred for 20 mins. A solution of alcohol (5.1 g) prepared in reference example 7 in methylene chloride (5 ml) was added to the mixture. The reaction mixture was stirred at −60° C. for 50 mins. Triethylamine (12 ml) was added to the reaction mixture. The reaction mixture was taken out from a cooling bath. After 5 mins, water was added to the reaction mixture. The mixture was diluted with ethyhl acetate. The diluted mixture was washed in order with water, 1N hydrochloric acid, a saturated aqueous solution of sodium bicarbonate and brine and then dried over magnesium sulfate. The solution was evaporated. The residue was purified by column chromatography on silica gel (n-hexane:ethyl acetate=4:1) to give the title compound (5.0 g) having the following physical data. TLC (n-hexane:ethyl acetate=4:1) Rf 0.46.

REFERENCE EXAMPLE 12 methyl
4-(6-methoxymethoxy-2,5,7,8-tetramethyl-3,4-dihydro-
2H-benzo[1,2-b]pyran-2-yl)-2-butenoate

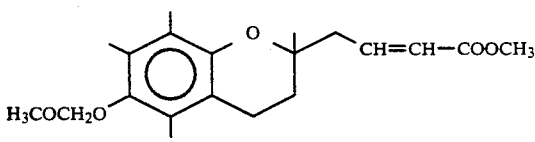

The aldehyde (5 g) prepared in reference example 11 was dissolved in benzene (40 ml). Methyl (triphenylphosphoranylidene)acetate (8.57 g) was added to this solution. The mixture was stirred at 80° C. for one hour. The reaction solution was evaporated. The residue was purified by column chromatography on silica gel (benzene:ethyl acetate=9:1) to give the title compound (5.6 g) having the following physical data.

TLC (n-hexane:ethyl acetate=4:1): Rf 0.43;
MS: m/e 348, 317, 303, 271, 249.

REFERENCE EXAMPLE 13 methyl
4-(6-methoxymethoxy-2,5,7,8-tetramethyl-3,4-dihydrio-
2H-benzo[1,2-b]pyran-2-yl)butylate

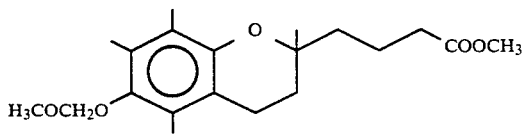

The ester (5.6 g) prepared in reference example 12 was dissolved in ethanol (40 ml). 5% Palladium carbon (1.5 g) was added to this solution. The mixture was stirred under an atmosphere of hydrogen for one hour. The catalyst was removed from the reaction solution with using a celite. The reaction solution was evaporated to give the residue (5.6 g) contained the title compound having the following physical data. The residue was used in next reaction without purification.

TLC (n-hexane:ethyl acetate=4:1): Rf 0.55;
MS: m/e 350, 319, 305, 273.

REFERENCE EXAMPLE 14

1-[2-(6-hydroxy-2,5,7,8-tetramethyl-3,4-dihydro-2H-
benzo[1,2-b]pyran-2-yl)ethyl]-3-(3-nitrophenyl)urea

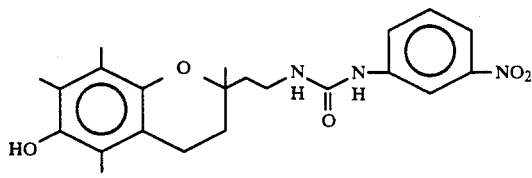

The amine (400 mg) prepared in reference example 3 was dissolved in anhydrous tetrahydrofuran (5 ml). A solution of 3-nitrophenylisocyanate (263 mg) in anhydrous tetrahydrofuran (1 ml) was added to the solution. The solution was stirred for 30 mins and then evaporated. The residue was diluted with ethyl acetate. The solution was washed with a saturated aqueous solution of sodium bicarbonate, 1N hydrochloric acid, followed by water, dried over magnesium sulfate and evaporated. The residue was purified by column chromatography on silica gel (n-hexane:ethyl acetate=1:1) to give the title compound (650 mg) having the following physical data.

TLC (benzene:ethyl acetate=2:1): Rf 0.45;
MS: m/e 413, 275, 249, 232, 220, 165.

REFERENCE EXAMPLE 15

4-(6-methoxymethoxy-2,5,7,8-tetramethyl-3,4-dihydro-
2H-benzo[1,2-b]pyran-2-yl)butyric acid

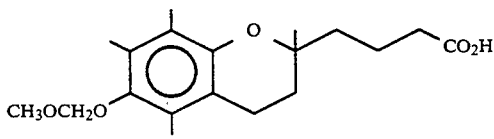

A 2N aqueous solution of sodium hydroxide (2.3 ml) was added to a solution of the methyl ester (800 mg), which was obtained with using the alcohol prepared in reference example 7 by the same procedure in order as reference example 11→reference example 12→reference example 13, in dimethoxy ethylene (20 ml). The solution was stirred at 50° C. all night. The reaction solution was left alone for a moment and cooled in an ice-bath. 2N hydrochloric acid (2.5 ml) was added to the cooled solution. The solution was extracted with ethyl acetate (60 ml). The extract was washed with water, next brine, dried over anhydrous magnesium sulfate and evaporated to give the title compound (763 mg) having the following physical data.

TLC (methanol:methylene chloride=1:19): Rf 0.26;
MS: m/e 336, 305, 292, 291, 273.

REFERENCE EXAMPLE 16

N-(3-nitrophenyl)-4-(6-methoxymethoxy-2,5,7,8-tet-
ramethyl-3,4-dihydro-2H-benzo[1,2-b]pyran-2-
yl)butylamide

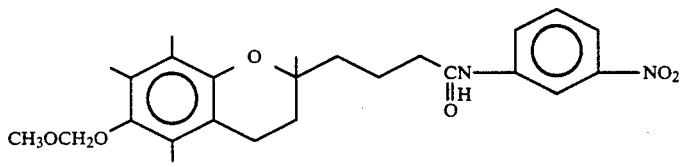

Triethylamine (0.17 ml) was added to a solution of the carboxylic acid (342 mg) prepared in reference example 15 in tetrahydrofuran (4 ml). The solution was cooled in an ice-bath. Ethyl chloroformate (0.11 ml) was added dropwise to the cooled solution. The solution was stirred for 2 mins. A solution of m-nitroaniline hydrochloride (177 mg) in a mixed solution of dimethylformamide (4 ml)-tetrahydrofuran (3 ml), which triethylamine (0.17 ml) was added to, was added dropwise to the stirred solution of the carboxylic acid. The mixture was stirred for 30 mins and moreover stirred at room temperature all night. The mixture was diluted with ether (60 ml). The diluted solution was washed in order with water, 1N hydrochloric acid, a saturated aqueous solution of sodium bicarbonate, water and brine, dried over anhydrous magnesium sulfate and evaporated. The residue was purified by column chromatography on silica gel (ethyl acetate:n-hexane=1:4→2:3) to give the title compound (188 mg) having the following physical data.

TLC (ethyl acetate:n-hexane=2:3): Rf 0.34;
MS: m/e 456, 426, 411, 395, 273, 255, 245, 231.

REFERENCE EXAMPLE 17

N-[2-(6-hydroxy-2,5,7,8-tetramethyl-3,4-dihydro-2H-benzo[1,2-b]pyran-2-yl)ethyl]-3-ethoxycarbonyl-5-nitrobenzamine

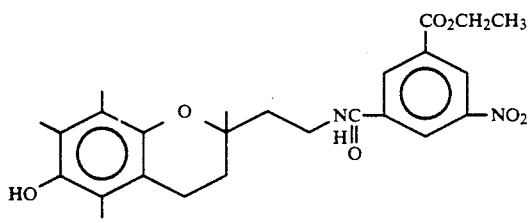

Oxalyl chloride (6.65 ml) was added dropwise to a mixture of dimethylformamide (70 ml) and methylene chloride (70 ml) cooled by a mixture of dry ice and methanol. The mixture was stirred for 25 mins with cooling. A solution of 3-ethoxycarbonyl-5-nitrobenzoic acid (18.2 g) in dimethylformamide (70 ml) was added dropwise to the mixture with cooling. The mixture was stirred at room temperature for one hour. A solution of the amine (20 g) prepared in reference example 3 in a mixed solution of dimethylformamide (150 ml) and methylene chloride (20 ml) was cooled by a mixture of dry ice and methanol. N,N-diisopropylethylamine (76 ml) was added to the cooled solution. The mixture prepared beforehand was added dropwise to the solution. The mixture was stirred at room temperature for 25 mins and then evaporated. The residue was diluted with ethyl acetate (600 ml). The diluted solution was washed with water and then brine, dried over anhydrous magnesium sulfate and evaporated. The residue was purified by column chromatography on silica gel (ethyl acetate:n-hexane=2:3) to give the title compound (28.4 g) having the following physical data.

TLC (ethyl acetate:benzene=1; 4): Rf 0.30;
MS: m/e 470, 222.

REFERENCE EXAMPLE 18

2-(6-methoxymethoxy-2,5,7,8-tetramethyl-3,4-dihydro-2H-benzo[1,2-b]pyran-2-yl)ethyl p-toluenesulfonate

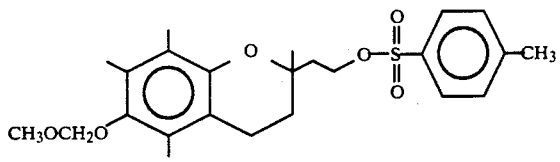

The alcohol (500 mg) prepared in reference example 7 was dissolved in pyridine (1.37 ml). The solution was cooled in an ice-bath. p-Toluenesulfonyl chloride (389 mg) was added to the cooled solution. The solution was taken out from an ice-bath and stirred at room temperature for 3 hours and then diluted with ethyl acetate. The diluted solution was washed with a saturated aqueous solution of cupric sulfate and then water, dried over anhydrous magnesium sulfate and then evaporated. The residue was purified by column chromatography on silica gel (n-hexane:ethyl acetate=4:1) to give the title compound (740 mg) having the following physical data.

TLC (n-hexane:ethyl acetate=2:1): Rf 0.57.

REFERENCE EXAMPLE 19

2-ethoxycarbonyl-4-nitrophenyl 2-(6-methoxtymethoxy-2,5,7,8-tetramethyl-3,4-dihydro-2H-benzo[1,2-b]pyran-2-yl)ethyl ether

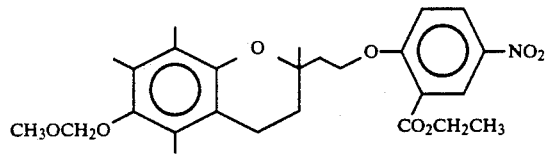

Anhydrous tetrahydrofuran (1 ml) and anhydrous hexamethylphosphoramide (1 ml) were added to ethyl 5-nitrosalicylate (100 mg). Sodium hydride (content 62.4%, 20 mg) was added to the mixture. The mixture was stirred for 20 mins. A solution of the tosylate (213 mg) prepared in reference example 18 in anhydrous tetrahydrofuran (1 ml) was added to the solution. The reaction mixture was stirred at 60° C. for 72 hours. The reaction solution was diluted with water. The diluted solution was extracted with a mixed solution of ethyl acetate and ether (1:1). The extract was washed with water and then a saturated brine, dried over anhydrous magnesium sulfate and then evaporated. The residue was purified by column chromatography on silica gel (n-hexane:ethyl acetate=4:1) to give the title compound (220 mg) having the following physical data.

TLC (n-hexane:ethyl acetate=4:1): Rf 0.23;
MS: m/e 487, 442, 426, 396, 231.

REFERENCE EXAMPLE 20

4-(3-hydroxypropyl)phenyl 2-(6-methoxymethoxy-2,5,7,8-tetramethyl-3,4-dihydro-2H-benzo[1,2-b]pyran-2-yl)ethyl ether

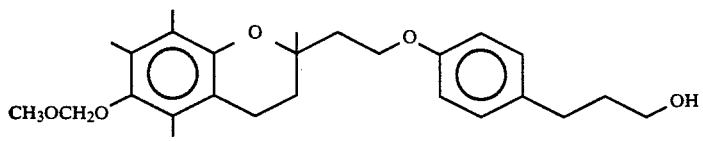

Sodium hydride (185 mg) was added to a solution of 3-(4-hydroxyphenyl)propanol (560 mg) in tetrahydrofuran (6 ml). The mixture was stirred at room temperature under an atmosphere of argon. After the evolution of hydrogen finished, hexamethylphosphoramide (3 ml) was added to the solution. A solution of the tosyl compound (1.5 g), which was prepared with using the alcohol prepared in reference example 7 by the same procedure as reference example 18, in hexamethylphosphoramide (6 ml) was added dropwise to this solution. The solution was stirred at 80° C. all night. The reaction solution was permitted to stand for a moment. Water was added to the solution. The solution was slightly acidified with 2N hydrochloric acid and extracted with ethyl acetate (150 ml). The organic layer was washed with, in order, a saturated aqueous solution of sodium bicarbonate, an aqueous solution of sodium thiosulfate, water and then saturated brine, dried over anhydrous sodium sulfate and then evaporated.

The residue was purified by column chromatography on silica gen (n-hexane:ethyl acetate=2:1) to give the title compound (1.22 g) having the following physical data.

NMR: δ7.09 (2H, d), 6.80 (2H, d), 4.86 (2H, s), 4.17 (2H, m), 3.66 (2H, q), 3.62 (3H, s), 3.63 (4H, m), 2.20 (3H, s), 2.15 (3H, s), 2.10 (3H, s), 1.95–1.80 (4H, m), 1.35 (3H, s).

REFERENCE EXAMPLE 21 t-butyl 2-(6-methoxymethoxy-2,5,7,8-tetramethyl-3,4-dihydro-2H-benzo[1,2-b]pyran-2-yl)ethoxyacetate

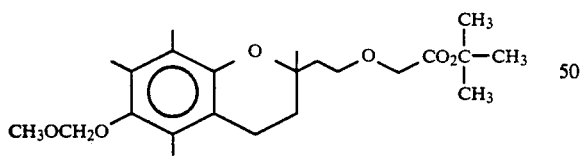

The alcohol (200 mg) prepared in reference example 7 was dissolved in methylene chloride (3 ml). A 20% aqueous solution of sodium hydroxide (3 ml) was added to this solution. Tetrabutylammonium hydrogen sulfate (46 mg) and tert-butyl α-bromoacetate (0.55 ml) were added to the solution. The mixture was stirred with violence at room temperature for 48 hours. The reaction mixture was extracted with chloroform. The extract was washed with water and then saturated brine, dried over anhydrous magnesium sulfate and then evaporated. The residue was purified by column chromatography on silica gel (n-hexane:ethyl acetate=9:1) to give the title compound (220 mg) having the following physical data.

TLC (n-hexane:ethyl acetate=4:1): Rf 0.54; MS: m/e 408, 363, 352, 335, 307, 277, 231, 203.

REFERENCE EXAMPLE 22

2-(2-trifluoroacetoaminoethyl)-3,4-dihydro-2,5,7,8-tetramethyl-6-methoxymethoxybenzo[1,2-b]pyran

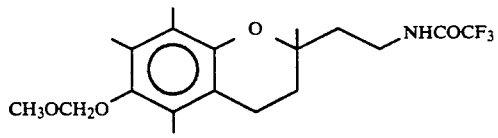

2-(2-aminoethyl)-3,4-dihydro-2,5,7,8-tetramethyl-6-methoxymethoxybenzo[1,2-b]pyran (84.1 g), which was prepared with using the alcohol prepared in reference example 7 by the same procedure as in order, reference example 2→reference example 3, was dissolved in a mixed solution of dimethylformamide (500 ml) and disopropylethylamine (60 ml). Ethyl trifluoroacetate (41.0 ml) was added dropwise to the solution at 5° C. The mixture was stirred at room temperature all night. The reaction mixture was evaporated. The residue was extracted with a mixed solution of ethyl acetate and n-hexane (1:3). The extract was washed with water and then brine, dried over anhydrous magnesium sulfate, and evaporated to give the title compound (109.9 g) having the following physical data.

TLC (n-hexane:ethyl acetate=5:1): Rf 0.28.

REFERENCE EXAMPLE 23

2-methylaminoethyl-2,5,7,8-tetramethyl-3,4-dihydro-6-methoxymethoxybenzo[1,2-b]pyran

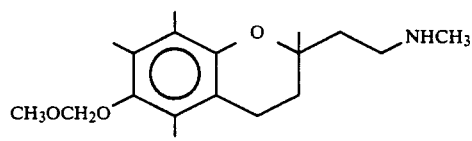

The benzopyran derivative (109.9 g) prepared in reference example 22 was dissolved in dimethylformamide (500 ml). Sodium hydride (12.43 g) was added to the solution with cooling in an icebath. After the temperature of the mixture was raised to room temperature, the mixture was stirred for one hour. The mixture was cooled in an ice-bath and methyl iodide was added thereto. The temperature of the mixture was rised to room temperature and the mixture stirred for one hour. A little water was added to the reaction solution. The solution was evaporated. A little water was added to the residue. The mixture was extracted with a mixed solution of ethyl acetate and n-hexane (1:3). The extract was washed with water and then brine, dried over anhydrous magnesium sulfate and then evaporated. A 2N aqueous solution of sodium hydroxide (148.6 ml), methanol (300 ml) and tetrahydrofuran (30 ml) were added to the residue. The mixture was stirred at 5° C. for 38 hours. The reaction mixture was evaporated. Water was added to the residue. The mixture was extracted with ethyl acetate. The extract was evaporated. The residue was purified by column chromatography on silica gel (chloroform:methanol = 10:1→3:1→5:2) to give the title compound (72.1 g) having the following phgysical data.

TLC (ethyl acetate:acetic acid:water=12:2:1): Rf 0.31;

MS: m/e 307, 262, 219.

EXAMPLE 1

2-(6-hydroxy-2,5,7,8-tetramethyl-3,4-dihydro-2H-benzo[1,2-b]pyran-2-yl)ethyl 4-guanidinomethylbenzoate hydrochloride

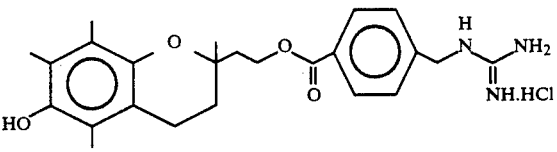

4-guanidinomethylbenzoic acid hydrochloride (229 mg) was added to a solution of dicyclohexylcarbodiimide (206 mg) in dimethylformamide (2.5 ml). After 10 minutes, a solution of the alcohol (prepared in reference example 1, 250 mg) in pyridine (2.5 ml) was added to the solution. The solution was stirred for 2 hours. The reaction solution was filtered. The filtrate was evaporated. The residue was purified by column chromatography on silica gel (chloroform:methanol=6:1) to give the title compound (176 mg) having the following physical data.

TLC (chloroform:methanol=6:1): Rf 0.19;
MS: m/e 425, 408, 383.

EXAMPLE 1(a)–1(m)

The compounds of the present invention shown in the following table 3 were obtained with using the corresponding carboxylic acid and alcohol by the same procedure as example 1.

TABLE 3

| Example No. | Structure | Name | TLC | MS m/e |
|---|---|---|---|---|
| 1(a) | 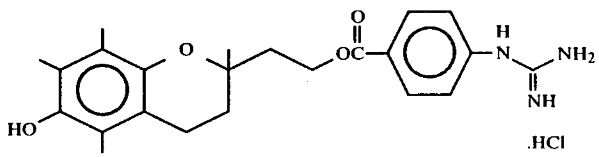 | 2-(6-hydroxy-2,5,7,8-tetramethyl-3,4-dihydro-2H-benzo[1,2-b]pyran-2-yl)ethyl 4-guanidinobenzoate hydrochloride | Rf 0.23 (chloroform: methanol = 3:1) | 411, 394, 369, 248, 232, 162, 120 |
| 1(b) | 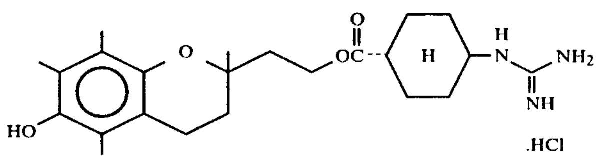 | 2-(6-hydroxy-2,5,7,8-tetramethyl-3,4-dihydro-2H-benzo[1,2-b]pyran-2-yl)ethyl 4-guanidinomethylcyclohexane carboxylate hydrochloride | Rf 0.20 (chloroform: methanol = 4:1) | 431, 414, 389, 302, 288, 250, 164 |
| 1(c) | 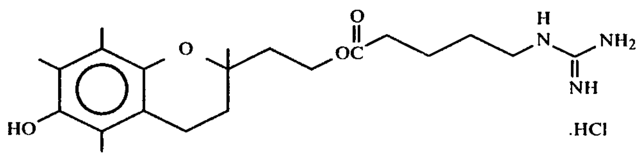 | 2-(6-hydroxy-2,5,7,8-tetramethyl-3,4-dihydro-2H-benzo[1,2-b]pyran-2-yl)ethyl 5-guanidinopentanoate hydrochloride | Rf 0.58 (ethyl acetate: acetic acid: water = 3:1:1) | 391 ($M^+$), 368, 349, 250, 228, 164 |
| 1(d) | 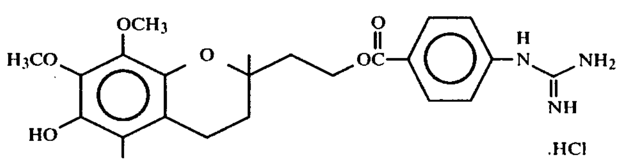 | 2-(2,5-dimethyl-6-hydroxy-7,8-dimethoxy-3,4-dihydro-2H-benzo[1,2-b]pyran-2-yl)ethyl 4-guanidinobenzoate hydrochloride | Rf 0.55 (ethyl acetate: acetic acid: water = 4:1:1) | 443, 426, 401, 282, 264, 196, 162, 120 |
| 1(e) | 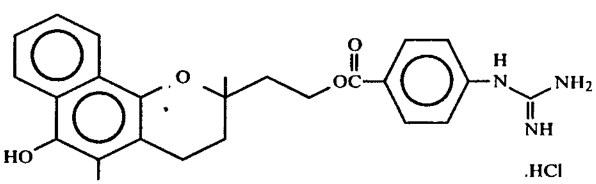 | 2-(2,5-dimethyl-6-hydroxy-3,4-dihydro-2H-naphtho[1,2-b]pyran-2-yl)ethyl 4-guanidinobenzoate hydrochloride | Rf 0.60 (ethyl acetate: acetic acid: water = 4:1:1) | 433, 391, 272, 254, 186, 120 |

TABLE 3-continued

| Example No. | Structure | Name | TLC | MS m/e |
|---|---|---|---|---|
| 1(f) | 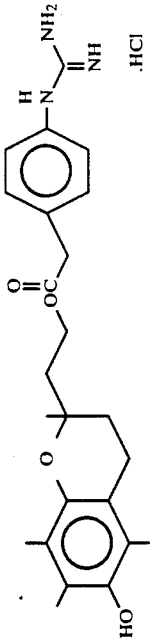 | 2-(6-hydroxy-2,5,7,8-tetramethyl-3,4-dihydro-2H-benzo[1,2-b]pyran-2-yl)ethyl (4-guanidinophenyl)acetate hydrochloride | Rf 0.61 (ethyl acetate: acetic acid: water = 3:1:1) | 425 (M+), 383, 262, 250, 232, 164, 106 |
| 1(g) | 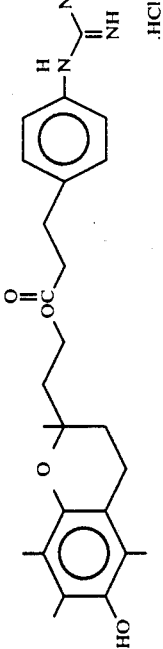 | 2-(6-hydroxy-2,5,7,8-tetramethyl-3,4-dihydro-2H-benzo[1,2-b]pyran-2-yl)ethyl 3-(4-guanidinophenyl)-propionate hydrochloride | Rf 0.58 (ethyl acetate: acetic acid: water = 3:1:1) | 439 (M+), 397, 276 |
| 1(h) | 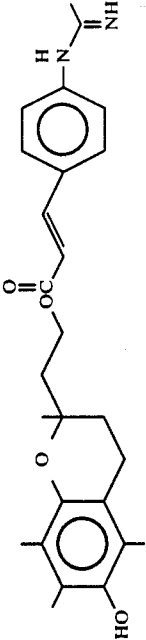 | 2-(6-hydroxy-2,5,7,8-tetramethyl-3,4-dihydro-2H-benzo[1,2-b]pyran-2-yl)ethyl 4-guanidinocinnamate hydrochloride | Rf 0.63 (ethyl acetate: acetic acid: water = 3:1:1) | 437 (M+) |
| 1(i) | 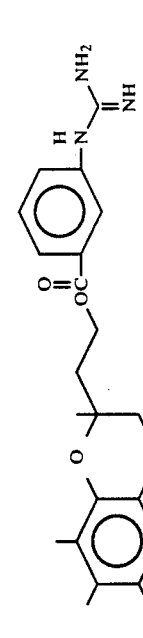 | 2-(6-hydroxy-2,5,7,8-tetramethyl-3,4-dihydro-2H-benzo[1,2-b]pyran-2-yl)ethyl 3-guanidinobenzoate hydrochloride | Rf 0.64 (ethyl acetate: acetic acid: water = 3:1:1) | 411 (M+), 394, 369, 248 |
| 1(j) | 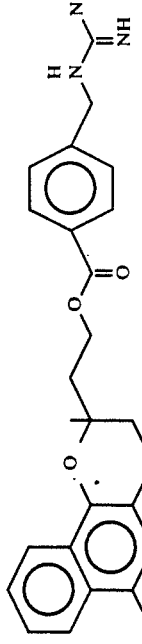 | 2-(2,5-dimethyl-6-hydroxy-3,4-dihydro-2H-naphtho[1,2-b]pyran-2-yl)ethyl 4-guanidinomethylbenzoate hydrochloride | Rf 0.46 (ethyl acetate: acetic acid: water = 4:1:1) | 447, 405, 272, 254, 187 |

TABLE 3-continued

| Example No. | Structure | Name | TLC | MS m/e |
|---|---|---|---|---|
| 1(k) | (structure with naphtho-pyran, HO, O, benzoate with NH-C(=NH)NH₂·HCl) | 2-(2,5-dimethyl-6-hydroxy-3,4-dihydro-2H-naphtho[1,2-b]pyran-2-yl)ethyl 3-guanidinobenzoate hydrochloride | Rf 0.45 (ethyl acetate: acetic acid: water = 4:1:1) | 433, 416, 391, 272, 254, 186, 120 |
| 1(l) | (structure with naphtho-pyran, HO, O, cinnamate with NH-C(=NH)NH₂·HCl) | 2-(2,5-dimethyl-6-hydroxy-3,4-dihydro-2H-naphtho[1,2-b]pyran-2-yl)ethyl 4-guanidinocinnamate hydrochloride | Rf 0.59 (ethyl acetate: acetic acid: water = 4:1:1) | 459, 417, 272, 186 |
| 1(m) | (structure with tetramethyl benzopyran, HO, O, benzoate with N(CH₃)-C(=NH)NH₂·HCl) | 2-(6-hydroxy-2,5,7,8-tetramethyl-3,4-dihydro-2H-benzo[1,2-b]pyran-2-yl)ethyl 4-(1-methylguanidino)-benzoate hydrochloride | Rf 0.47 (ethyl acetate: acetic acid: water = 4:1:1) | 425, 383, 262, 232, 134 |

EXAMPLE 2

N-[2-(6-hydroxy-2,5,7,8-tetramethyl-3,4-dihydro-2H-benzo[1,2-b]pyran-2-yl)ethyl]-4-guanidinobenzamide hydrochloride

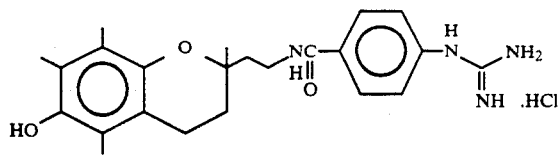

The amine (prepared in reference example 3, 1.0 g) and 4-guanidinobenzoic acid hydrochloride (0.95 g) were dissolved in the mixture of pyridine (5 ml) and dimethylformamide (5 ml). Dicyclohexylcarbodiimide (0.91 g) was added to the solution. The mixture was stirred for 2.5 days. The reaction solution was fitered. The filtrate was evaporated. The residue was dissolved in methanol (10 ml), and 1N hydrochloric acid (6 ml) was added to the solution. The solution was evaporated. The residue was purified by column chromatography on silica gel (methylene chloride:methanol=10:1) to give the title compound (275 mg) having the following physical data.

TLC (ethyl acetate:acetic acid:water=3:1:1): Rf 0.62; MS: m/e 410, 368, 120.

EXAMPLE 2(a)–2(g)

The compounds of the present invention shown in the following table 4 were obtained with using the corresponding carboxylic acid and amine by the same procedure as example 2.

TABLE 4

| Example No. | Structure | Name | TLC | MS m/e |
|---|---|---|---|---|
| 2(a) | 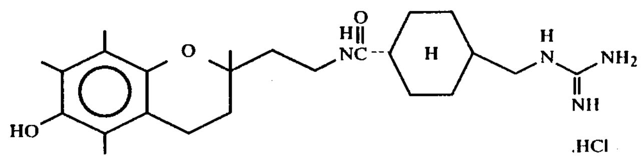 | N-[2-(6-hydroxy-2,5,7,8-tetramethyl-3,4-dihydro-2H-benzo[1,2-b]pyran-2-yl)ethyl]-4-guanidinomethyl-cyclohexanecarboxamide hydrochloride | Rf 0.53 (ethyl acetate: acetic acid: water = 3:1:1) | 431 |
| 2(b) | 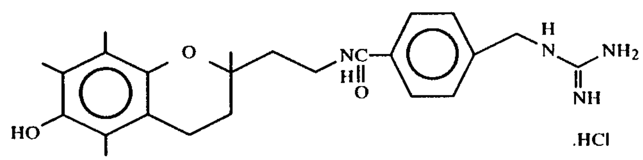 | N-[2-(6-hydroxy-2,5,7,8-tetramethyl-3,4-dihydro-2H-benzo[1,2-b]pyran-2-yl)ethyl]-4-guanidinomethyl-benzamide hydrochloride | Rf 0.47 (ethyl acetate: acetic acid: water = 3:1:1) | 424, 407, 382 |
| 2(c) | 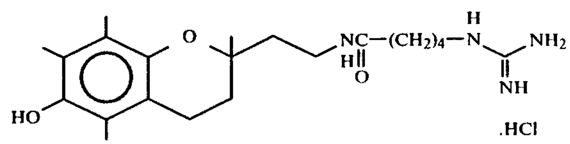 | N-[2-(6-hydroxy-2,5,7,8-tetramethyl-3,4-dihydro-2H-benzo[1,2-b]pyran-2-yl)ethyl]-5-guanidinopentanamide hydrochloride | Rf 0.50 (ethyl acetate: acetic acid: water = 3:1:1) | 390, 373, 348 |
| 2(d) | 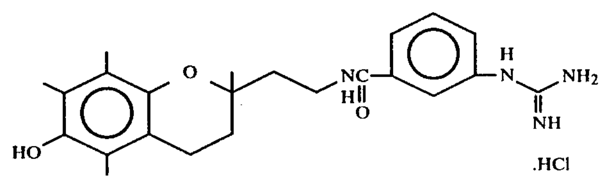 | N-[2-(6-hydroxy-2,5,7,8-tetramethyl-3,4-dihydro-2H-benzo[1,2-b]pyran-2-yl)ethyl]-3-guanidinobenzamide hydrochloride | Rf 0.54 (ethyl acetate: acetic acid: water = 4:1:1) | 410, 368, 164, 120 |
| 2(e) | 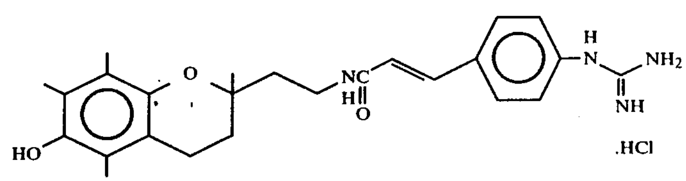 | N-[2-(6-hydroxy-2,5,7,8-tetramethyl-3,4-dihydro-2H-benzo[1,2-b]pyran-2-yl)ethyl]-4-guanidinocinnamide hydrochloride | Rf 0.48 (ethyl acetate: acetic acid: water = 4:1:1) | 436, 394, 249, 146 |

TABLE 4-continued

| Example No. | Structure | Name | TLC | MS m/e |
|---|---|---|---|---|
| 2(f) | 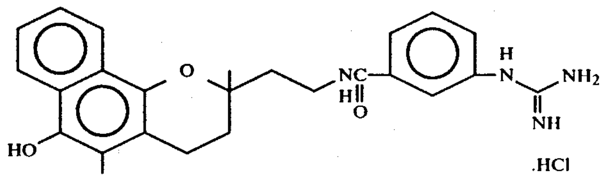 | N-[2-(6-hydroxy-2,5,7,8-tetramethyl-3,4-dihydro-2H-naphtho[1,2-b]pyran-2-yl)-ethyl]-3-guanidinobenzamide hydrochloride | Rf 0.42 (ethyl acetate: acetic acid: water = 4:1:1) | 432, 390, 271, 254 |
| 2(g) | 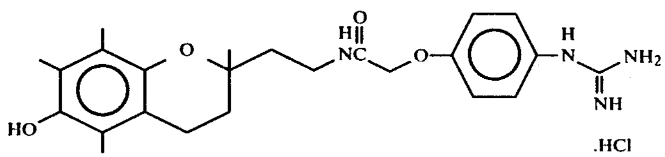 | N-[2-(6-hydroxy-2,5,7,8-tetramethyl-3,4-dihydro-2H-benzo[1,2-b]pyran-2-yl)-ethyl]-4-guanidinophenoxy-acetamide hydrochloride | Rf 0.32 (ethyl acetate: acetic acid: water = 12:2:1) | 440, 398, 277, 233, 203, 165, 122, 109 |

EXAMPLE 3

1-amino-3-[2-(6-hydroxy-2,5,7,8-tetramethyl-3,4-dihydro-2H-benzo[1,2-b]pyran-2-yl)ethyl]guanidine hydroiodide reference example 1→reference example 2→reference example 3→reference example 4→reference example 5) by the same procedure as example 3.

TABLE 5

| Example No. | Structure | Name | TLC | MS m/e |
|---|---|---|---|---|
| 3(a) | 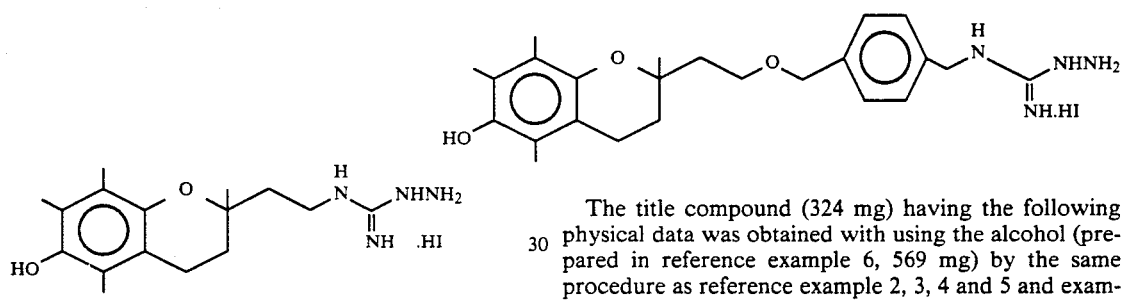 | 1-amino-3-[2-(2,5-dimethyl-6-hydroxy-7,8-dimethoxy-3,4-dihydro-2H-benzo[1,2-b]pyran-2-yl)ethyl guanidine hydroiodide | Rf 0.32 (ethyl acetate: acetic acid: water = 10:2:1) | 338 (M$^+$), 232, 308, 197, 142 |

The thiourea (prepared in reference example 5, 17.4 g) was dissolved in ethanol (170 ml). A solution of methyl iodide (24.0 g) in ethanol (10.5 ml) was added dropwise to the solution over 2 hours at room temperature. After confirmation of conclusion of the reaction by TLC, the solution was evaporated. The residue (24.3 g) was dissolved in methanol (170 ml). A solution of hydrazine hydride (5.65 g) in methanol (80 ml) was added dropwise to the solution at room temperature. The solution was stirred for 2 days. The reaction solution was evaporated. The residue was purified by column chromatography on silica gel (chloroform:methanol=95:5→90:10) to give the title compound (19.6 g) having the following physical data.

TLC (ethyl acetate:acetic acid:water=10:2:1): Rf 0.51;
MS: m/e 306, 291, 276.

EXAMPLE 3(a)

The compound of the present invention shown in the following table 5 was obtained with using the thiourea (prepared with using the corresponding methyl ester as starting material by the same procedure as, in order

EXAMPLE 4

4-(3-aminoguamidinomethyl)benzyl 2-(6-hydroxy-2,5,7,8-tetramethyl-3,4-dihydro-2H-benzo[1,2-b]pyran-2-yl)ethyl ether hydroiodide The title compound (324 mg) having the following physical data was obtained with using the alcohol (prepared in reference example 6, 569 mg) by the same procedure as reference example 2, 3, 4 and 5 and example 3.

TLC (ethyl acetate:acetic acid:water=10:2:1): Rf 0.4;
MS: m/e 427, 412, 277, 250.

EXAMPLE 4(a)

The compound of the present invention shown in the following table 6 was obtained with using the corresponding alcohol by the same procedure as example 4.

TABLE 6

| Example No. | Structure | Name | TLC | MS m/e |
|---|---|---|---|---|
| 4(a) | 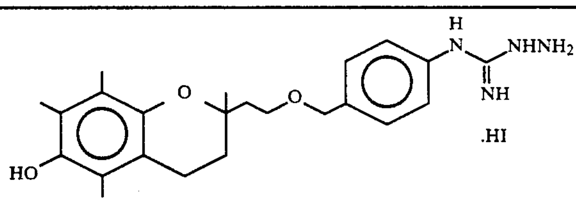 | 4-(3-aminoguanidino)benzyl 2-(6-hydroxy-2,5,7,8-tetramethyl-3,4-dihydro-2H-benzo[1,2-b]pyran-2-yl)ethyl ether hydroiodide | Rf 0.43 (ethyl acetate: acetic acid: water = 4:1:1) | 413, 382, 250, 232, 220, 165 |

EXAMPLE 5

4-guanidinophenyl 2-(6-hydroxy-2,5,7,8-tetramethyl-3,4-dihydro-2H-benzo[1,2-b]pyran-2-yl)ethyl ether hydrochloride

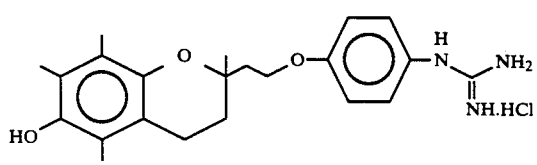

A saturated solution of hydrochloric acid in ethanol (100 ml) was added to a solution of the amine (61 g)

prepared in reference example 10 in ethanol (250 ml). The solution was evaporated. The residue obtained was washed well with ether and then dried. A 50 wt % aqueous solution of cyanamide (27.0 ml) was added to a suspension of the crystal (65.9 g) thus obtained in ethanol (250 ml). The mixture was stirred at 80° C. for one day. The reaction mixture was evaporated. The obtained crystal was washed well with ether and recrystallized from a mixded solution of ethanol and ether to give the title compound (58.6 g) having the following physical data.

TLC (ethyl acetate:acetic acid:water=12:2:1): Rf 0.47;

MS: m/e 383, 366, 341, 233, 220, 205, 165.

EXAMPLE 5(a)–5(g)

The compounds of the present invention shown in the following table 7 were obtained with using the corresponding ether compounds, which were prepared with using the alcohol prepared in reference example 7 by the same procedure as, in order, reference example 8 (with the proviso that the corresponding nitro compounds were used instead of 1-chloro-4-nitrobenzene)→reference example 9→reference example 10, by the same procedure as example 5.

TABLE 7

| Example No. | Structure | Name | TLC | MS m/e |
|---|---|---|---|---|
| 5(a) | 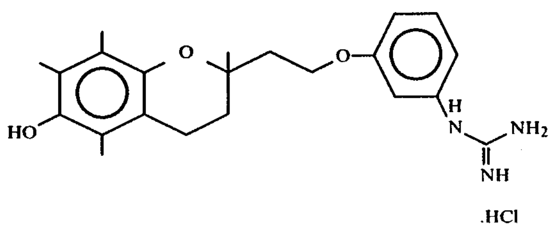 | 3-guanidinophenyl 2-(6-hydroxy-2,5,7,8-tetramethyl-3,4-dihydro-2H-benzo[1,2-b]-pyran-2-yl)ethyl ether hydrochloride | Rf 0.44 (ethyl acetate: acetic acid: water = 12:1:1) | 383 (M+), 366, 341, 220 |
| 5(b) | 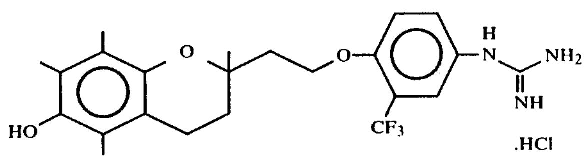 | 2-trifluoromethyl-4-guanidinophenyl 2-(6-hydroxy-2,5,7,8-tetramethyl-3,4-dihydro-2H-benzo[1,2-b]-pyran-2-yl)ethyl ether hydrochloride | Rf 0.27 (ethyl acetate: acetic acid: water = 15:2:1) | 451 (M+), 434, 409, 288, 233, 219, 165 |
| 5(c) | 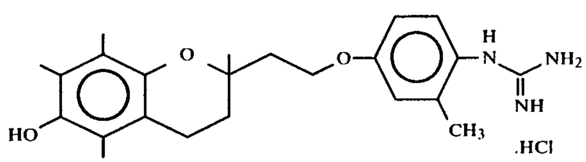 | 3-methyl-4-guanidinophenyl 2-(6-hydroxy-2,5,7,8-tetramethyl-3,4-dihydro-2H-benzo[1,2-b]pyran-2-yl)ethyl ether hydrochloride | Rf 0.29 (ethyl acetate: acetic acid: water = 15:2:1) | 397 (M+), 234, 205, 190, 165 |
| 5(d) | 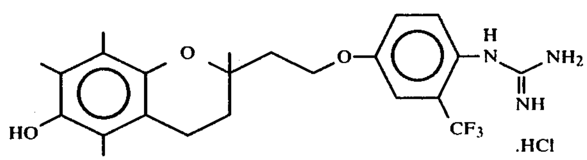 | 3-trifluoromethyl-4-guanidinophenyl 2-(6-hydroxy-2,5,7,8-tetramethyl-3,4-dihydro-2H-benzo[1,2-b]-pyran-2-yl)ethyl ether hydrochloride | Rf 0.42 (ethyl acetate: acetic acid: water = 10:2:1) | 452 (M+ + 1) |
| 5(e) | 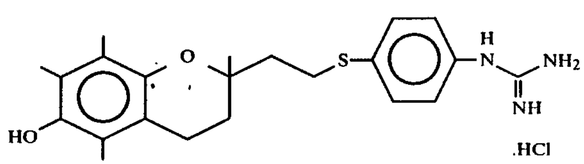 | 4-guanidinophenyl 2-(6-hydroxy-2,5,7,8-tetramethyl-3,4-dihydro-2H-benzo[1,2-b]-pyran-2-yl)ethyl thioether hydrochloride | Rf 0.41 (ethyl acetate: acetic acid: water = 10:2:1) | 400, 236, 165 |

TABLE 7-continued

| Example No. | Structure | Name | TLC | MS m/e |
|---|---|---|---|---|
| 5(f) | [structure: 4-guanidinophenyl ether of naphthopyran, ·HCl] | 4-guanidinophenyl 2-(2,5-dimethyl-6-hydroxy-3,4-dihydro-2H-naphtho[1,2-b]-pyran-2-yl)ethyl ether hydrochloride | Rf 0.38 (ethyl acetate: acetic acid: water = 12:2:1) | 406, 220, 187, 164, 152 |
| 5(g) | [structure: 4-guanidinophenyl thioether of naphthopyran, ·HCl] | 4-guanidinophenyl 2-(2,5-dimethyl-6-hydroxy-3,4-dihydro-2H-naphtho[1,2-b]-pyran-2-yl)ethyl thioether hydrochloride | Rf 0.46 (ethyl acetate: acetic acid: water = 12:2:1) | 422, 236, 185 |

EXAMPLE 6

4-(3-aminoguanidino)phenyl 2-(6-hydroxy-2,5,7,8-tetramethyl-3,4-dihydro-2H-benzo[1,2-b]pyran-2-yl)ethyl ether hydroiodide used instead of 1-chloro-4-nitrobenzene)→reference example 9 reference example 10 in order) by the same procedure as example 6.

TABLE 8

| Example No. | Structure | Name | TLC | MS m/e |
|---|---|---|---|---|
| 6(a) | (structure shown) | 3-trifluoromethyl-4-(3-aminoguanidino)phenyl 2-(6-hydroxy-2,5,7,8-tetramethyl-3,4-dihydro-2H-benzo[1,2-b]-pyran-2-yl)ethyl ether hydroiodide | Rf 0.18 (methanol:chloroform = 1:4) | 477 (M$^+$), 451, 436, 409, 303, 288, 165 |
| 6(b) | (structure shown) | 3-(3-aminoguanidino)phenyl 2-(6-hydroxy-2,5,7,8-tetramethyl-3,4-dihydro-2H-benzo[1,2-b]pyran-2-yl)ethyl ether hydroiodide | Rf 0.24 (methanol:chloroform = 1:9) | 399 (M$^+$ + 1) |

EXAMPLE 7

N-[4-[2-(6-hydroxy-2,5,7,8-tetramethyl-3,4-dihydro-2H-benzo[1,2-b]pyran-2-yl)ethoxy]phenyl]-4-guanidinobenzamide hydrochloride

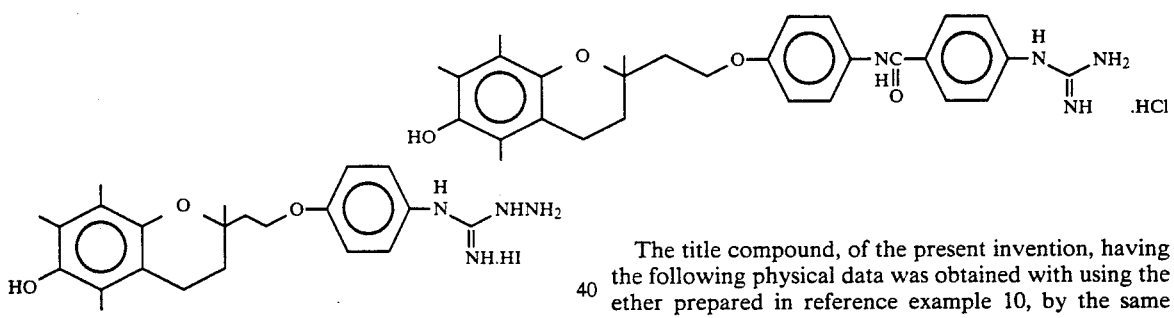

The title compound, of the present invention, having the following physical data was obtained with using the ether prepared in reference example 10 by the same procedure as, in order, reference example 4→reference example 5→example 3.

TLC (ethyl acetate:acetic acid:water = 3:1:1): Rf 0.64; MS: m/e 398, 368, 341, 233, 205, 165.

EXAMPLE 6(a) and 6(b)

The compounds, of the present invention, shown in the following table 8 were obtained with using the corresponding ether compounds (which was prepared with using the alcohol prepared in reference example 7 by the same procedure as reference example 8 (with the proviso that the correesponding nitro compound was The title compound, of the present invention, having the following physical data was obtained with using the ether prepared in reference example 10, by the same procedure as example 2.

TLC (ethyl acetate:acetic acid:water = 4:1:1): Rf 0.50; MS: m/e 460, 165, 120.

EXAMPLE 7(a)-7(cc)

The compounds, of the present invention, shown in the following table 9 were obtained the corresponding ether compound (which were prepared with using the alcohol prepared in reference example 7 by the same procedure as reference example 8 (with the proviso that the corresponding nitrobenzene compounds were used instead of 1-chloro-4-nitrobenzene to prepared the compounds in example 7(c)-7(g))→reference example 9→reference example 10 in order) and the corresponding appropriate carboxylic acid by the same procedure as example 7.

TABLE 9

| Example No. | Structure | Name | TLC | MS m/e |
|---|---|---|---|---|
| 7 (a) | 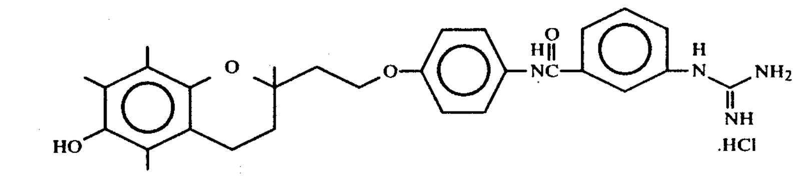 | N-[4-[2-(6-hydroxy-2,5,7,8-tetramethyl-3,4-dihydro-2H-benzo[1,2-b]pyran-2-yl)ethoxy]phenyl]-3-guanidino-benzamide hydrochloride | Rf 0.45 (ethyl acetate: acetic acid: water = 4:1:1) | 460, 165, 120 |
| 7 (b) | 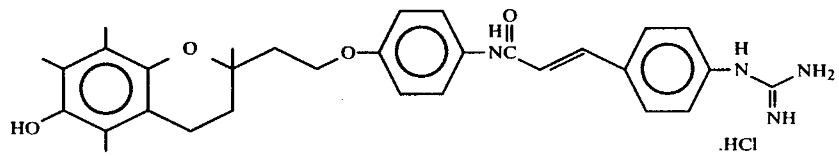 | N-[4-[2-(6-hydroxy-2,5,7,8-tetramethyl-3,4-dihydro-2H-benzo[1,2-b]pyran-2-yl)ethoxy]phenyl]-4-guanidino-cinnamamide hydrochloride | Rf 0.52 (ethyl acetate: acetic acid: water = 4:1:1) | 486, 368, 341, 165, 146 |
| 7 (c) | 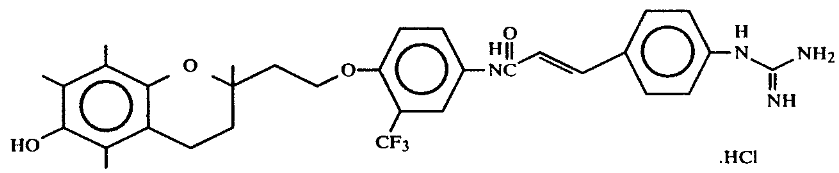 | N-[3-trifluoromethyl-4-[2-(6-hydroxy-2,5,7,8-tetramethyl-3,4-dihydro-2H-benzo[1,2-b]pyran-2-yl)ethoxy]phenyl]-4-guanidino-cinnamamide hydrochloride | Rf 0.28 (ethyl acetate: acetic acid: water = 10:2:1) | 689, 597 (M$^+$ + 1) |
| 7 (d) | 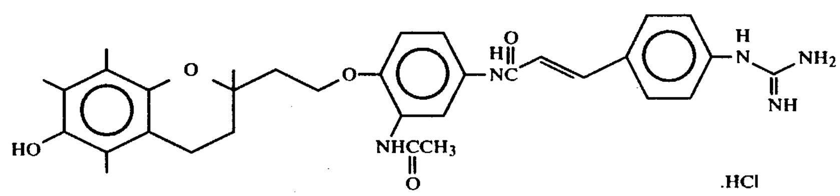 | N-[3-acetoamido-4-[2-(6-hydroxy-2,5,7,8-tetramethyl-3,4-dihydro-2H-benzo[1,2-b]pyran-2-yl)ethoxy]phenyl]-4-guanidinocinnamamide hydrochloride | Rf 0.25 (ethyl acetate: acetic acid: water = 10:2:1) | 586 (M$^+$ + 1) |
| 7 (e) | 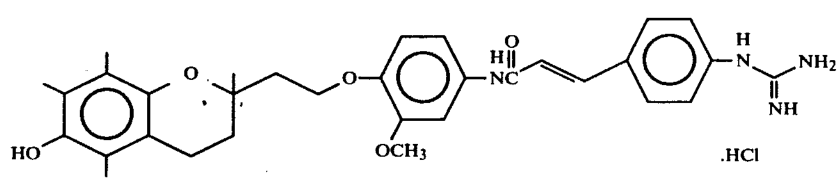 | N-[3-methoxy-4-[2-(6-hydroxy-2,5,7,8-tetramethyl-3,4-dihydro-2H-benzo[1,2-b]pyran-2-yl)ethoxy]phenyl]-4-guanidinocinnamamide hydrochloride | Rf 0.38 (methylene chloride: methanol: acetic acid = 10:2:1) | 652, 559 |

TABLE 9-continued

| Example No. | Structure | Name | TLC | MS m/e |
|---|---|---|---|---|
| 7 (f) | 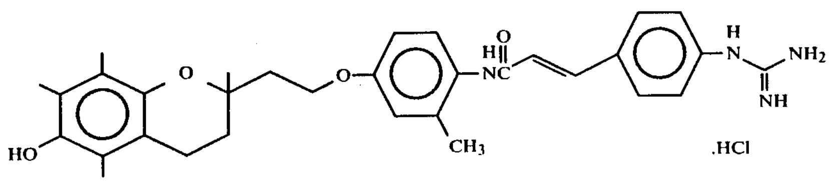 | N-[2-methyl-4-[2-(6-hydroxy-2,5,7,8-tetramethyl-3,4-dihydro-2H-benzo[1,2-b]pyran-2-yl)ethoxy]phenyl]-4-guanidinocinnamamide hydrochloride | Rf 0.24 (ethyl acetate: acetic acid: water = 10:2:1) | 695, 543 (M$^+$ + 1) |
| 7 (g) | 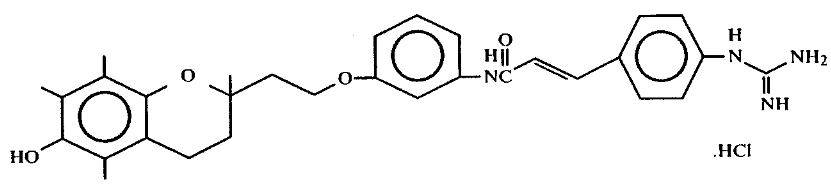 | N-[3-[2-(6-hydroxy-2,5,7,8-tetramethyl-3,4-dihydro-2H-benzo[1,2-b]pyran-2-yl)ethoxy]phenyl]-4-guanidinocinnamamide hydrochloride | Rf 0.62 (ethyl acetate: acetic acid: water = 3:1:1) | 486, 341, 146 |
| 7 (h) | 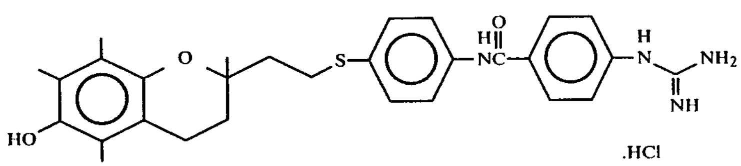 | N-[4-[2-(6-hydroxy-2,5,7,8-tetramethyl-3,4-dihydro-2H-benzo[1,2-b]pyran-2-yl)ethylthio]phenyl]-4-guanidinobenzamide hydrochloride | Rf 0.40 (ethyl acetate: acetic acid: water = 12:2:1) | 519, 355, 287, 203, 185, 162 |
| 7 (i) | 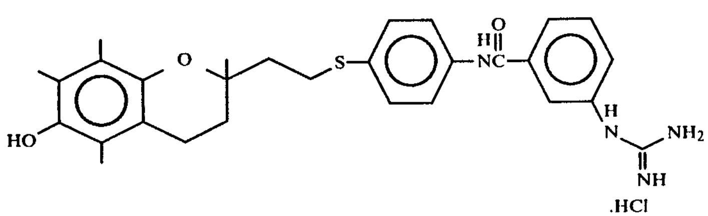 | N-[4-[2-(6-hydroxy-2,5,7,8-tetramethyl-3,4-dihydro-2H-benzo[1,2-b]pyran-2-yl)ethylthio]phenyl]-3-guanidinobenzamide hydrochloride | Rf 0.46 (ethyl acetate: acetic acid: water = 12:2:1) | 519, 355, 313, 287, 270, 162 |
| 7 (j) | 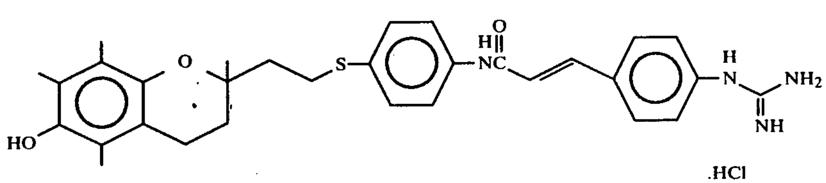 | N-[4-[2-(6-hydroxy-2,5,7,8-tetramethyl-3,4-dihydro-2H-benzo[1,2-b]pyran-2-yl)ethylthio]phenyl]-4-guanidinocinnamamide hydrochloride | Rf 0.37 (ethyl acetate: acetic acid: water = 12:2:1) | 545, 381, 205, 188, 165, 146 |

TABLE 9-continued

| Example No. | Structure | Name | TLC | MS m/e |
|---|---|---|---|---|
| 7 (k) | 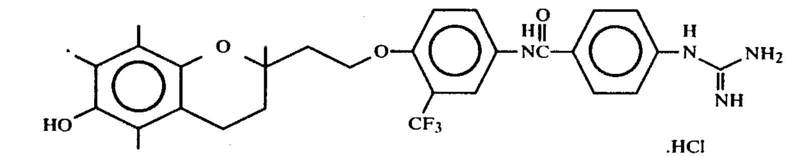 | N-[4-[2-(6-hydroxy-2,5,7,8-tetramethyl-3,4-dihydro-2H-benzo[1,2-b]pyran-2-yl)-ethoxy]-3-trifluoromethyl-phenyl]-4-guanidinobenzamide hydrochloride | Rf 0.31 (ethyl acetate: acetic acid: water = 10:2:1) | 571, 407, 162, 135, 120 |
| 7 (l) | 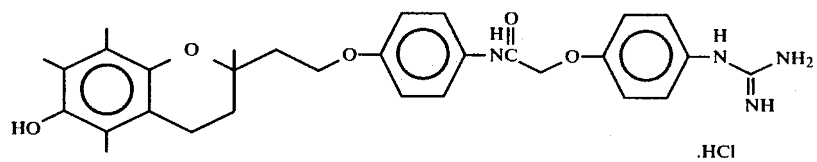 | N-[4-[2-(6-hydroxy-2,5,7,8-tetramethyl-3,4-dihydro-2H-benzo[1,2-b]pyran-2-yl)ethoxy]phenyl]-4-guanidinophenoxyacetamide hydrochloride | Rf 0.34 (ethyl acetate: acetic acid: water = 12:2:1) | 533, 277, 185, 165, 93, 75, 56 |
| 7 (m) | 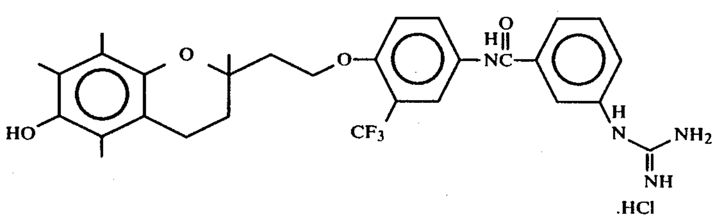 | N-[4-[2-(6-hydroxy-2,5,7,8-tetramethyl-3,4-dihydro-2H-benzo[1,2-b]pyran-2-yl)ethoxy]-3-trifluoromethyl-phenyl]-3-guanidinobenzamide hydrochloride | Rf 0.34 (ethyl acetate: acetic acid: water = 10:2:1) | 571, 407, 205, 165 |
| 7 (n) | 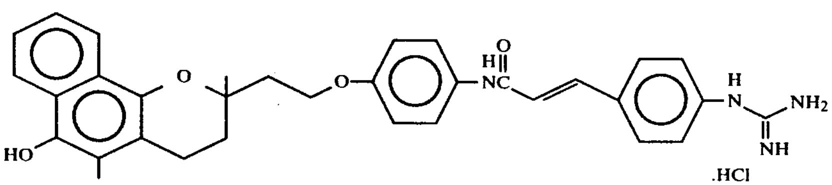 | N-[4-[2-(2,5-dimethyl-6-hydroxy-3,4-dihydro-2H-naphtho[1,2-b]pyran-2-yl)ethoxy]phenyl]-4-guanidinocinnamamide hydrochloride | Rf 0.28 (ethyl acetate: acetic acid: water = 12:2:1) | 551, 365, 185 |
| 7 (o) | 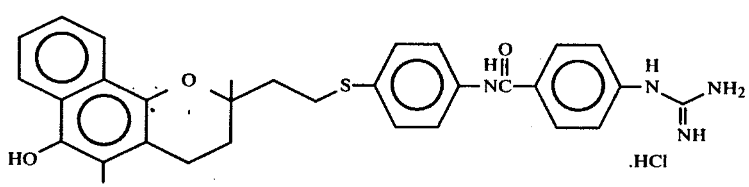 | N-[4-[2-(2,5-dimethyl-6-hydroxy-3,4-dihydro-2H-naphtho[1,2-b]pyran-2-yl)ethylthio]phenyl]-4-guanidinobenzamide hydrochloride | Rf 0.25 (ethyl acetate: acetic acid: water = 12:2:1) | 541, 355, 162, 120 |

TABLE 9-continued

| Example No. | Structure | Name | TLC | MS m/e |
|---|---|---|---|---|
| 7 (p) | 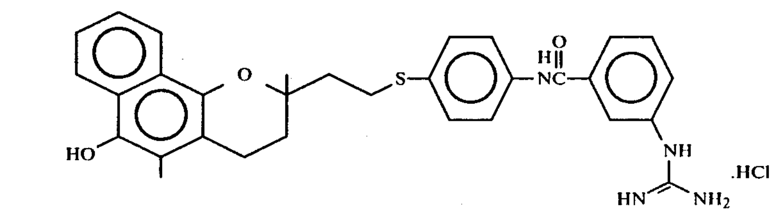 | N-[4-[2-(2,5-dimethyl-6-hydroxy-3,4-dihydro-2H-naphtho[1,2-b]pyran-2-yl)-ethylthio]phenyl]-3-guanidinobenzamide hydrochloride | Rf 0.30 (ethyl acetate: acetic acid: water = 12:2:1) | 541, 355, 162 |
| 7 (q) | 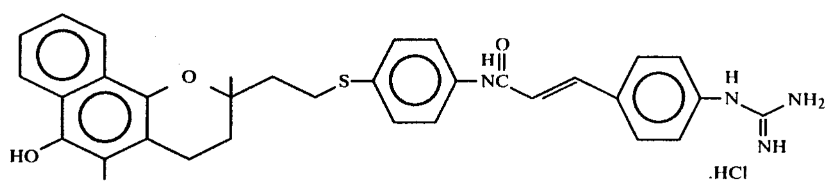 | N-[4-[2-(2,5-dimethyl-6-hydroxy-3,4-dihydro-2H-naphtho[1,2-b]pyran-2-yl)-ethylthio]phenyl]-4-guanidinocinnamamide hydrochloride | Rf 0.24 (ethyl acetate: acetic acid: water = 12:2:1) | 567, 369, 277, 185 |
| 7 (r) | 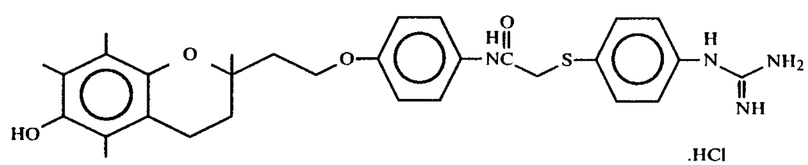 | N-[4-[2-(6-hydroxy-2,5,7,8-tetramethyl-3,4-dihydro-2H-benzo[1,2-b]pyran-2-yl)ethoxy]phenyl]-4-guanidinophenylthioacetamide hydrochloride | Rf 0.28 (ethyl acetate: acetic acid: water = 15:2:1) | 550, 385, 233, 203, 165, 135 |
| 7 (s) | 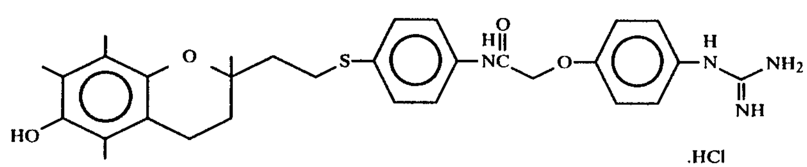 | N-[4-[2-(6-hydroxy-2,5,7,8-tetramethyl-3,4-dihydro-2H-benzo[1,2-b]pyran-2-yl)ethylthio]phenyl]-4-guanidinophenoxyacetamide hydrochloride | Rf 0.20 (ethyl acetate: acetic acid: water = 15:2:1) | 549, 385, 165 |
| 7 (t) | 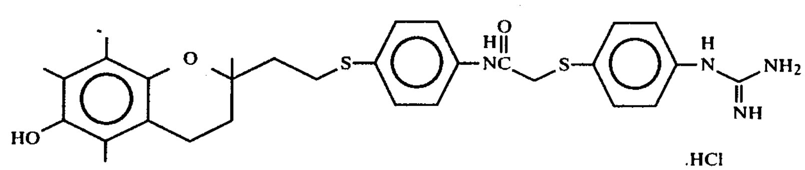 | N-[4-[2-(6-hydroxy-2,5,7,8-tetramethyl-3,4-dihydro-2H-benzo[1,2-b]pyran-2-yl)ethylthio]phenyl]-4-guanidinophenylthioacetamide hydrochloride | Rf 0.28 (ethyl acetate: acetic acid: water = 15:2:1) | 565, 399, 277, 205, 185, 165, 138, 93 |

TABLE 9-continued

| Example No. | Structure | Name | TLC | MS m/e |
|---|---|---|---|---|
| 7 (u) | 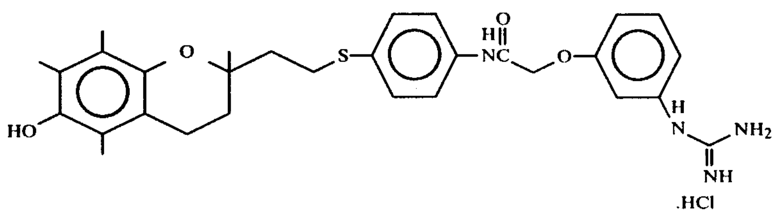 | N-[4-[2-(6-hydroxy-2,5,7,8-tetramethyl-3,4-dihydro-2H-benzo[1,2-b]pyran-2-yl)-ethylthio]phenyl]-3-guanidinophenoxyacetamide hydrochloride | Rf 0.31 (ethyl acetate: acetic acid: water = 15:2:1) | 549, 385, 165 |
| 7 (v) | 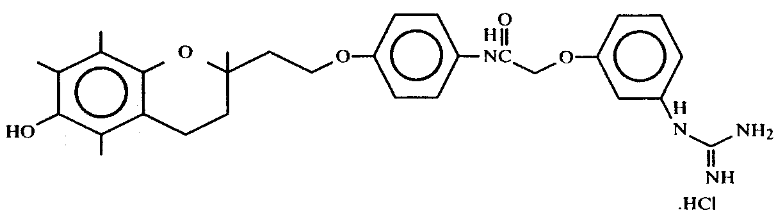 | N-[4-[2-(6-hydroxy-2,5,7,8-tetramethyl-3,4-dihydro-2H-benzo[1,2-b]pyran-2-yl)-ethoxy]phenyl]-3-guanidino-phenoxyacetamide hydrochloride | Rf 0.23 (ethyl acetate: acetic acid: water = 15:2:1) | 533, 369, 203, 165 |
| 7 (w) | 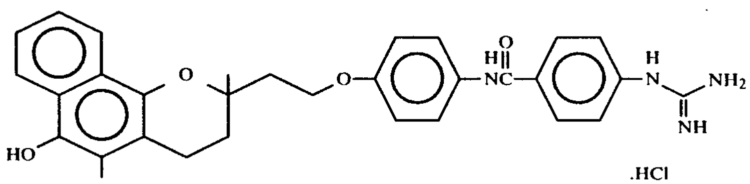 | N-[4-[2-(2,5-dimethyl-6-hydroxy-3,4-dihydro-2H-naphtho[1,2-b]pyran-2-yl)-ethoxy]phenyl]-4-guanidino-benzamide hydrochloride | Rf 0.26 (ethyl acetate: acetic acid: water = 10:2:1) | 525, 339, 187, 162, 120 |
| 7 (x) | 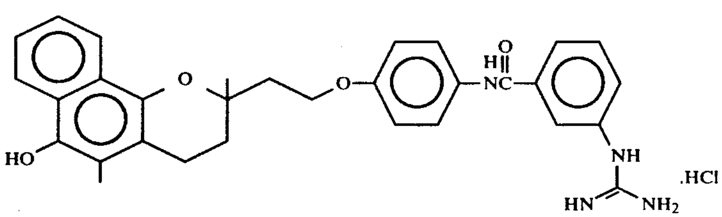 | N-[4-[2-(2,5-dimethyl-6-hydroxy-3,4-dihydro-2H-naphtho[1,2-b]pyran-2-yl)-ethoxy]phenyl]-3-guanidino-benzamide hydrochloride | Rf 0.29 (ethyl acetate: acetic acid: water = 10:2:1) | 525, 339, 225, 187, 162, 135 |

TABLE 9-continued

| Example No. | Structure | Name | TLC | MS m/e |
|---|---|---|---|---|
| 7 (y) | 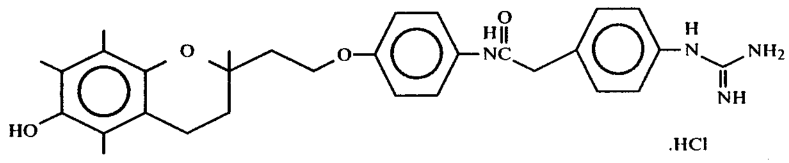 | N-[4-[2-(6-hydroxy-2,5,7,8-tetramethyl-3,4-dihydro-2H-benzo[1,2-b]pyran-2-yl)ethoxy]phenyl]-4-guanidinophenylacetamide hydrochloride | Rf 0.25 (ethyl acetate: acetic acid: water = 12:2:1) | 517, 353, 205, 185, 165, 149, 93 |
| 7 (z) | 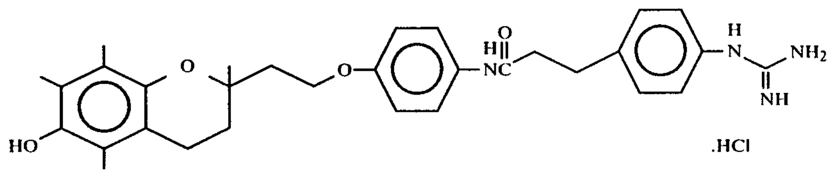 | N-[4-[2-(6-hydroxy-2,5,7,8-tetramethyl-3,4-dihydro-2H-benzo[1,2-b]pyran-2-yl)ethoxy]phenyl]-3-(4-guanidinophenyl)propionamide hydrochloride | Rf 0.27 (ethyl acetate: acetic acid: water = 12:2:1) | 531, 367, 277, 185, 165, 149, 93 |
| 7 (aa) | 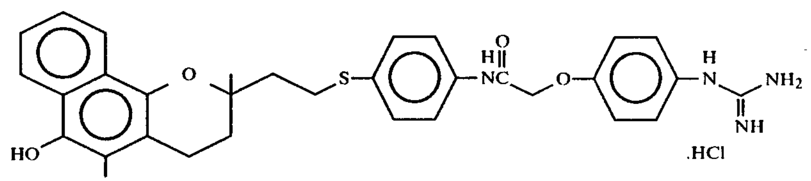 | N-[4-[2-(2,5-dimethyl-6-hydroxy-3,4-dihydro-2H-naphtho[1,2-b]pyran-2-yl)ethylthio]phenyl]-4-guanidinophenoxyacetamide hydrochloride | Rf 0.17 (ethyl acetate: acetic acid: water = 15:2:1) | 571, 385, 187, 164, 152, 135 |
| 7 (bb) | 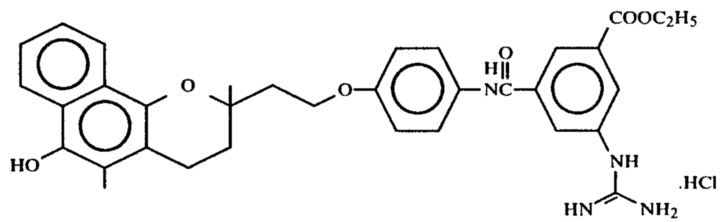 | N-[4-[2-(2,5-dimethyl-6-hydroxy-3,4-dihydro-2H-naphtho[1,2-b]pyran-2-yl)ethoxy]phenyl]-3-guanidino-5-ethoxycarbonyl-benzamide hydrochloride | Rf 0.31 (ethyl acetate: acetic acid: water = 15:2:1) | 597, 411, 369, 277, 185 |
| 7 (cc) | 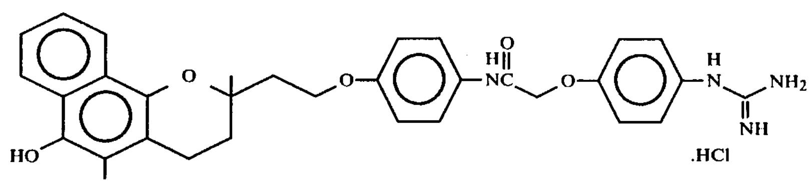 | N-[4-[2-(2,5-dimethyl-6-hydroxy-3,4-dihydro-2H-naphtho[1,2-b]pyran-2-yl)ethoxy]phenyl]-4-guanidinophenoxyacetamide hydrochloride | Rf 0.14 (ethyl acetate: acetic acid: water = 15:2:1) | 555, 539, 405, 369, 187, 164, 152, 135 |

EXAMPLE 8

1-amino-3-[4-(6-hydroxy-2,5,7,8-tetramethyl-3,4-dihydro-2H-benzo[1,2-b]pyran-2-yl)butyl]guanidine hydroiodide

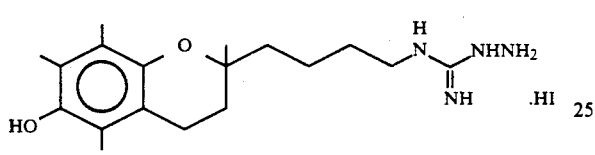

The title compound, of the present invention, having the following physical data was obtained with using the methyl ester prepared in reference example 13 by the same procedure as reference example 1→reference example 2→reference example 9→reference example 3→reference example 4→reference example 5→example 3 in order.

TLC (ethyl acetate:acetic acid:water = 12:2:1): Rf 0.29;

MS: m/e 335, 320, 304, 278.

EXAMPLE 9

N-[4-[4-(6-hydroxy-2,5,7,8-tetramethyl-3,4-dihydro-2H-benzo[1,2-b]pyran-2-yl)butoxy]phenyl]-4-guanidinocinnamamide hydrochloride

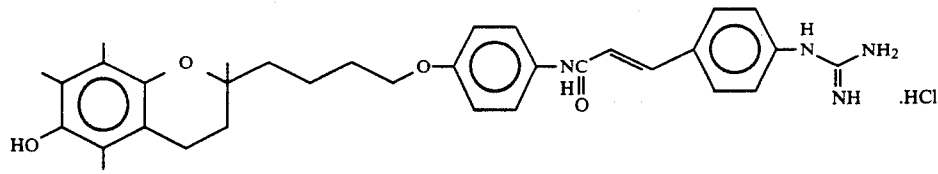

The title compound, of the present invention, having the following physical data was obtained with using the methyl ester prepared in reference example 13 by the same procedure as reference example 1→reference example 8→reference example 9→reference example 10→example 2 (with the proviso that 4-guanidinocinnamic acid hydrochloride was used instead of 4-guanidinobenzoic acid hydrochloride) in order.

TLC (ethyl acetate:acetic acid:water = 3:1:1): Rf 0.57;

MS: m/e 514, 370, 261, 205.

EXAMPLE 9(a)-9(r)

The compounds, of the present invention, shown in the following table 10 were obtained with using the methyl ester prepared in reference example 13 or the corresponding appropriate methyl ester by the same procedure as example 9 (with the proviso that the corresponding carboxylic acid hydrochloride was used instead of 4-guanidinocinnamic acid hydrochloride and the corresponding appropriate nitro compounds were used instead of 1-chloro-4-nitrobenzene to prepared the compounds in example 9(c)-9(h), 9(j)-9(l), 9(n) and 9(q).

TABLE 10

| Example No. | Structure | Name | TLC | MS m/e |
|---|---|---|---|---|
| 9 (a) | 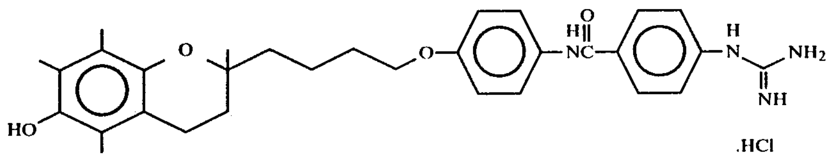 | N-[4-[4-(6-hydroxy-2,5,7,8-tetramethyl-3,4-dihydro-2H-benzo[1,2-b]pyran-2-yl)butoxy]phenyl]-4-guanidinobenzamide hydrochloride | Rf 0.23 (ethyl acetate: acetic acid: water = 12:2:1) | 530, 488, 369, 165, 120 |
| 9 (b) | 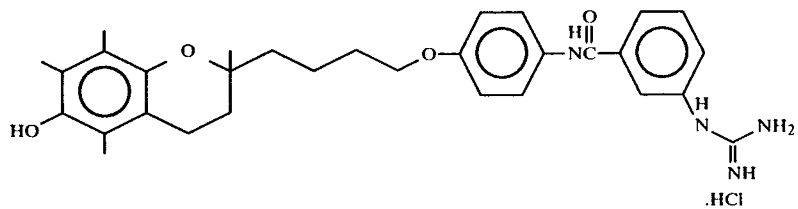 | N-[4-[4-(6-hydroxy-2,5,7,8-tetramethyl-3,4-dihydro-2H-benzo[1,2-b]pyran-2-yl)butoxy]phenyl]-3-guanidinobenzamide hydrochloride | Rf 0.27 (ethyl acetate: acetic acid: water = 12:2:1) | 530, 489, 368, 324, 297, 203, 165, 120 |
| 9 (c) | 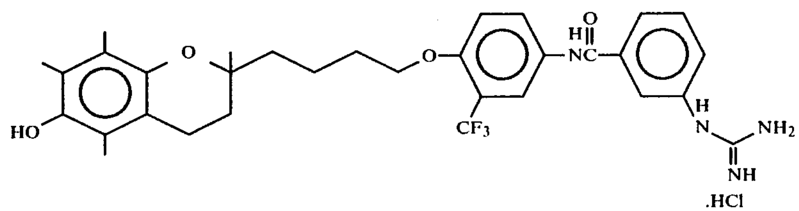 | N-[3-trifluoromethyl-4-[4-(6-hydroxy-2,5,7,8-tetramethyl-3,4-dihydro-2H-benzo[1,2-b]pyran-2-yl)butoxy]phenyl]-3-guanidinobenzamide hydrochloride | Rf 0.37 (ethyl acetate: acetic acid: water = 12:2:1) | 598, 557, 436, 393, 297, 203, 165, 120 |
| 9 (d) | 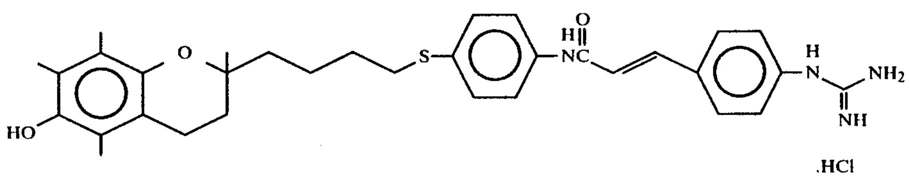 | N-[4-[4-(6-hydroxy-2,5,7,8-tetramethyl-3,4-dihydro-2H-benzo[1,2-b]pyran-2-yl)butylthio]phenyl]-4-guanidinocinnamamide hydrochloride | Rf 0.37 (ethyl acetate: acetic acid: water = 12:2:1) | 573, 409, 203, 188, 165, 93 |
| 9 (e) | 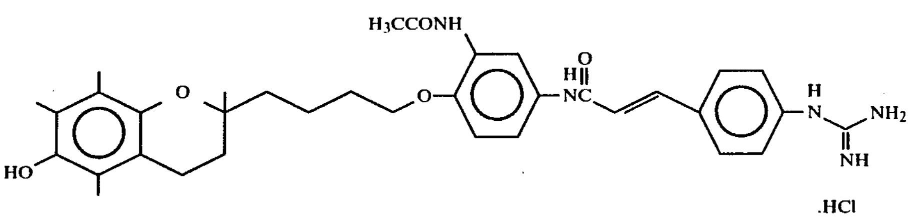 | N-[3-acetoamido-4-[4-(6-hydroxy-2,5,7,8-tetramethyl-3,4-dihydro-2H-benzo[1,2-b]pyran-2-yl)butoxy]phenyl]-4-guanidinocinnamamide hydrochloride | Rf 0.42 (ethyl acetate: acetic acid: water = 4:1:1) | 614, 553, 461, 369, 277, 211, 185, 165, 137, 93, 75, 56 |

TABLE 10-continued

| Example No. | Structure | Name | TLC | MS m/e |
|---|---|---|---|---|
| 9 (f) | (structure) | N-[4-[4-(6-hydroxy-2,5,7,8-tetramethyl-3,4-dihydro-2H-benzo[1,2-b]pyran-2-yl)-butylthio]phenyl]-4-guanidinobenzamide hydrochloride | Rf 0.32 (ethyl acetate: acetic acid: water = 12:2:1) | 547, 383, 185, 162, 135, 120, 93 |
| 9 (g) | (structure) | N-[4-[4-(6-hydroxy-2,5,7,8-tetramethyl-3,4-dihydro-2H-benzo[1,2-b]pyran-2-yl)-butylthio]phenyl]-3-guanidinobenzamide hydrochloride | Rf 0.35 (ethyl acetate: acetic acid: water = 12:2:1) | 547, 383, 369, 277, 185, 165, 93 |
| 9 (h) | (structure) | N-[4-[4-(6-hydroxy-2,5,7,8-tetramethyl-3,4-dihydro-2H-benzo[1,2-b]pyran-2-yl)-butoxyl]-3-methoxyphenyl]-4-guanidinocinnamamide hydrochloride | Rf 0.52 (ethyl acetate: acetic acid: water = 4:1:1) | 587, 277, 185, 165, 149, 93, 75, 56 |
| 9 (i) | (structure) | N-[4-[4-(2,5-dimethyl-6-hydroxy-3,4-dihydro-2H-naphtho[1,2-b]pyran-2-yl)-butoxy]phenyl]-4-guanidinocinnamamide hydrochloride | Rf 0.29 (ethyl acetate: acetic acid: water = 12:2:1) | 579, 393, 185 |

TABLE 10-continued

| Example No. | Structure | Name | TLC | MS m/e |
|---|---|---|---|---|
| 9 (j) | 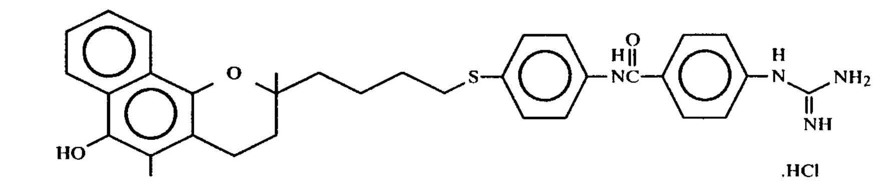 | N-[4-[4-(2,5-dimethyl-6-hydroxy-3,4-dihydro-2H-naphtho[1,2-b]pyran-2-yl)-butylthio]phenyl]-4-guanidinobenzamide hydrochloride | Rf 0.28 (ethyl acetate: acetic acid: water = 12:2:1) | 526, 407, 368 |
| 9 (k) | 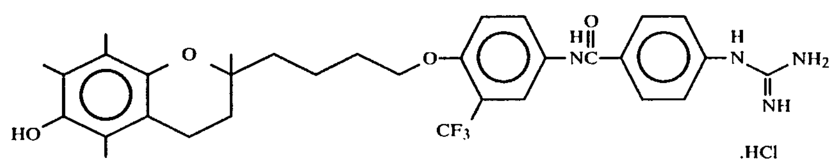 | N-[4-[4-(6-hydroxy-2,5,7,8-tetramethyl-3,4-dihydro-2H-benzo[1,2-b]pyran-2-yl)-butoxy]-3-trifluoromethylphenyl]-4-guanidinobenzamide hydrochloride | Rf 0.32 (ethyl acetate: acetic acid: water = 10:2:1) | 599, 435, 351, 165, 162, 135, 120 |
| 9 (l) | 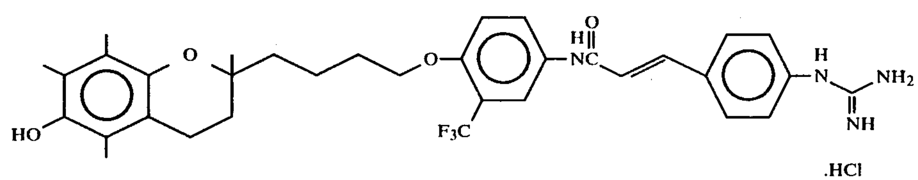 | N-[4-[4-(6-hydroxy-2,5,7,8-tetramethyl-3,4-dihydro-2H-benzo[1,2-b]pyran-2-yl)-butoxy]-3-trifluoromethylphenyl]-4-guanidinocinnamamide hydrochloride | Rf 0.24 (ethyl acetate: acetic acid: water = 10:2:1) | 625, 461, 203, 188, 165, 146, 135 |
| 9 (m) | 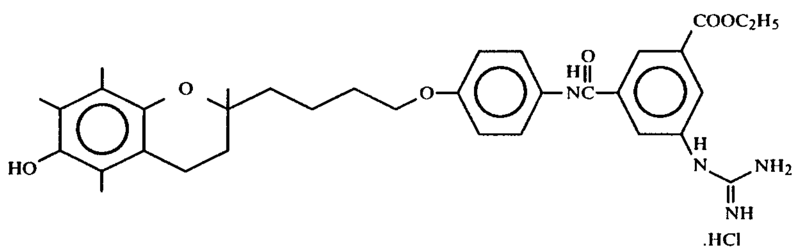 | N-[4-[4-(6-hydroxy-2,5,7,8-tetramethyl-3,4-dihydro-2H-benzo[1,2-b]pyran-2-yl)-butoxy]phenyl]-3-guanidino-4-ethoxycarbonylbenzamide hydrochloride | Rf 0.26 (ethyl acetate: acetic acid: water = 30:4:1) | 603, 461, 439, 369, 277, 185 |

TABLE 10-continued

| Example No. | Structure | Name | TLC | MS m/e |
|---|---|---|---|---|
| 9 (n) | 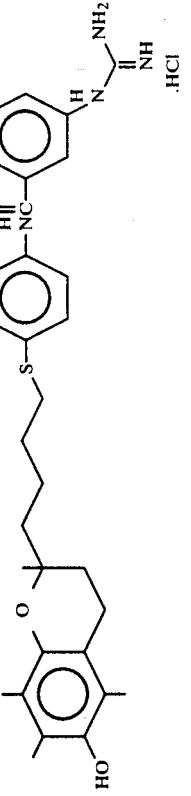 | N-[4-[4-(6-hydroxy-2,5,7,8-tetramethyl-3,4-dihydro-2H-benzo[1,2-b]pyran-2-yl)butylthio]phenyl]-3-guanidino-5-ethoxycarbonyl-benzamide hydrochloride | Rf 0.32 (ethyl acetate: acetic acid: water = 30:4:1) | 604, 461, 369, 277, 207, 185 |
| 9 (o) | 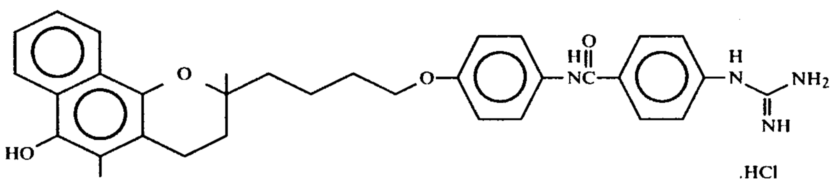 | N-[4-[4-(2,5-dimethyl-6-hydroxy-3,4-dihydro-2H-naphtho[1,2-b]pyran-2-yl)butoxy]phenyl]-4-guanidino-benzamide hydrochloride | Rf 0.31 (ethyl acetate: acetic acid: water = 10:2:1) | 553, 367, 162 |
| 9 (p) | 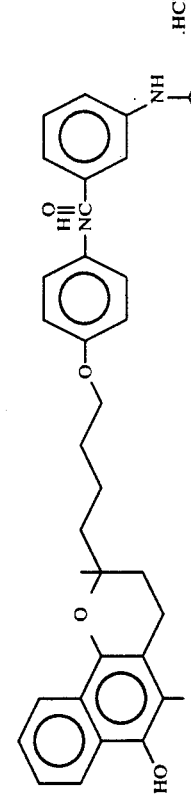 | N-[4-[4-(2,5-dimethyl-6-hydroxy-3,4-dihydro-2H-naphtho[1,2-b]pyran-2-yl)butoxy]phenyl]-3-guanidino-benzamide hydrochloride | Rf 0.34 (ethyl acetate: acetic acid: water = 10:2:1) | 553, 367, 162 |
| 9 (q) | 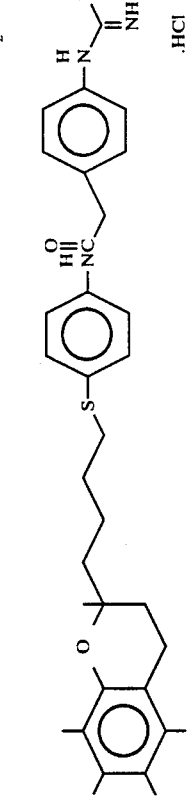 | N-[4-[4-(6-hydroxy-2,5,7,8-tetramethyl-3,4-dihydro-2H-benzo[1,2-b]pyran-2-yl)butylthio]phenyl]-4-guanidinophenylacetamide hydrochloride | Rf 0.34 (ethyl acetate: acetic acid: water = 12:2:1) | 561, 397, 300, 203, 165, 149, 106 |
| 9 (r) | 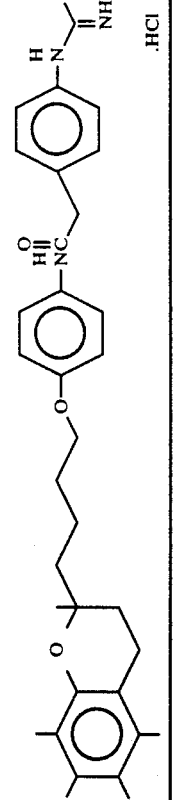 | N-[4-[4-(6-hydroxy-2,5,7,8-tetramethyl-3,4-dihydro-2H-benzo[1,2-b]pyran-2-yl)butoxy]phenyl]-4-guanidinophenylacetamide hydrochloride | Rf 0.32 (ethyl acetate: acetic acid: water = 12:2:1) | 545, 381, 165, 149, 106 |

EXAMPLE 10

4-guanidinophenyl 4-(6-hydroxy-2,5,7,8-tetramethyl-3,4-dihydro-2H-benzo[1,2-b]pyran-2-yl)butyl ether hydrochloride

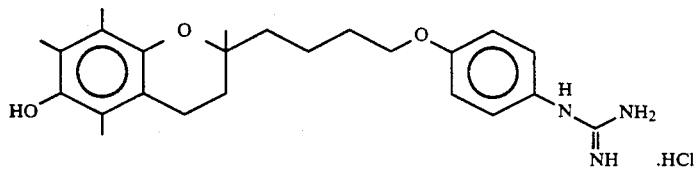

The title compound, of the present invention, having the following physical data was obtained with using the methyl ester prepared in reference example 13 by the same procedure as reference example 1→reference example 8→reference example 9→reference example 10→example 5 in order.

TLC (ethyl acetate:acetic acid:water=15:2:1): Rf 0.21;
MS: m/e 411, 369, 256, 248, 165.

EXAMPLE 10(a)–10(j)

The compounds, of the present invention, shown in the following table 11 were obtained with using the methyl ester prepared in reference example 13 by the same procedure as example 10 (with the proviso that the corresponding appropriate nitrobenzene compounds were used instead of 1-chloro-4-nitrobenzene).

TABLE 11

| Example No. | Structure | Name | TLC | MS m/e |
|---|---|---|---|---|
| 10 (a) | (structure) | 2-trifluoromethyl-4-guanidinophenyl 4-(6-hydroxy-2,5,7,8-tetramethyl-3,4-dihydro-2H-benzo[1,2-b]pyran-2-yl)butyl ether hydrochloride | Rf 0.24 (ethyl acetate: acetic acid: water = 15:2:1) | 480 (M+ + 1) |
| 10 (b) | (structure) | 3-guanidinophenyl 4-(6-hydroxy-2,5,7,8-tetramethyl-3,4-dihydro-2H-benzo[1,2-b]pyran-2-yl)butyl ether hydrochloride | Rf 0.45 (ethyl acetate: acetic acid: water = 12:2:1) | 411, 394, 369, 248, 165 |
| 10 (c) | (structure) | 4-guanidino-2-methoxyphenyl 4-(6-hydroxy-2,5,7,8-tetramethyl-3,4-dihydro-2H-benzo[1,2-b]pyran-2-yl)butyl ether hydrochloride | Rf 0.39 (ethyl acetate: acetic acid: water = 12:2:1) | 441, 424, 399, 278, 261, 205 |
| 10 (d) | (structure) | 2-acetoamido-4-guanidinophenyl 4-(6-hydroxy-2,5,7,8-tetramethyl-3,4-dihydro-2H-benzo[1,2-b]pyran-2-yl)butyl ether hydrochloride | Rf 0.29 (ethyl acetate: acetic acid: water = 12:2:1) | 469, 305, 165, 93 |
| 10 (e) | (structure) | 4-guanidinophenyl 4-(6-hydroxy-2,5,7,8-tetramethyl-3,4-dihydro-2H-benzo[1,2-b]pyran-2-yl)butyl thioether hydrochloride | Rf 0.43 (ethyl acetate: acetic acid: water = 10:2:1) | 427, 410, 385, 368, 264, 165 |

TABLE 11-continued

| Example No. | Structure | Name | TLC | MS m/e |
|---|---|---|---|---|
| 10 (f) | 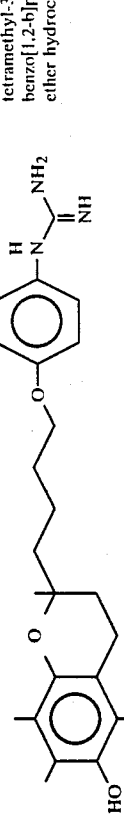 | 4-guanidino-3-trifluoromethyl-phenyl 4-(6-hydroxy-2,5,7,8-tetramethyl-3,4-dihydro-2H-benzo[1,2-b]pyran-2-yl)butyl ether hydrochloride | Rf 0.32 (ethyl acetate: acetic acid: water = 15:2:1) | 479, 462, 437, 368, 316, 219, 165 |
| 10 (g) | 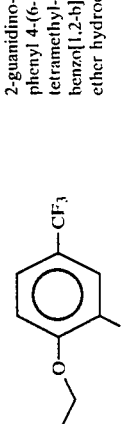 | 2-guanidino-4-trifluoromethyl-phenyl 4-(6-hydroxy-2,5,7,8-tetramethyl-3,4-dihydro-2H-benzo[1,2-b]pyran-2-yl)butyl ether hydrochloride | Rf 0.57 (ethyl acetate: acetic acid: water = 15:2:1) | 479, 462, 437, 316 |
| 10 (h) | 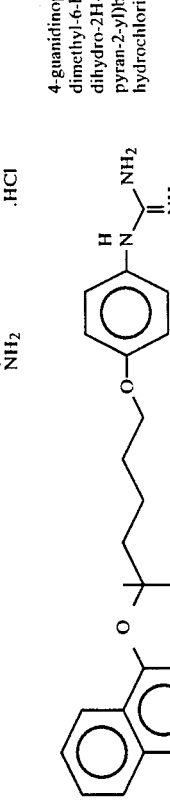 | 4-guanidinophenyl 4-(2,5-dimethyl-6-hydroxy-3,4-dihydro-2H-naphtho[1,2-b]pyran-2-yl)butyl ether hydrochloride | Rf 0.38 (ethyl acetate: acetic acid: water = 12:2:1) | 434, 248, 185 |
| 10 (i) | 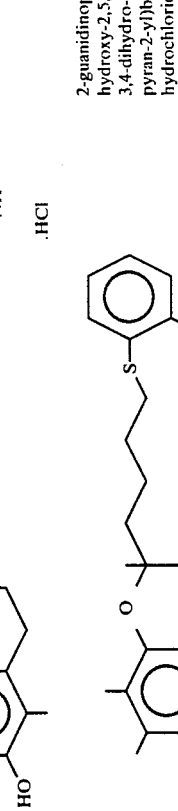 | 2-guanidinophenyl 4-(6-hydroxy-2,5,7,8-tetramethyl-3,4-dihydro-2H-benzo[1,2-b]pyran-2-yl)butyl thioether hydrochloride | Rf 0.37 (chloroform: methanol: acetic acid = 80:20:1) | 428, 264, 185, 165, 93 |
| 10 (j) | 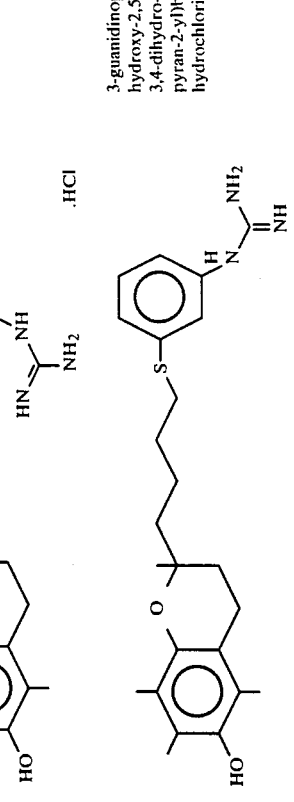 | 3-guanidinophenyl 4-(6-hydroxy-2,5,7,8-tetramethyl-3,4-dihydro-2H-benzo[1,2-b]pyran-2-yl)butyl thioether hydrochloride | Rf 0.38 (chloroform: methanol: acetic acid = 80:20:1) | 428, 264, 165, 135, 93 |

EXAMPLE 11

1-[2-(6-hydroxy-2,5,7,8-tetramethyl-3,4-dihydro-2H-benzo[1,2-b]pyran-2-yl)ethyl]-3-(3-guanidinophenyl-)urea hydrochloride

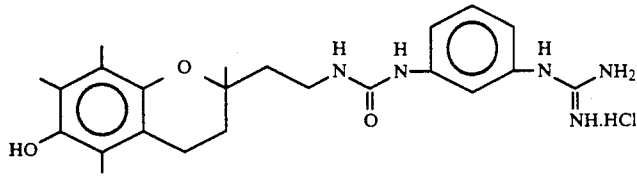

The title compound, of the present invention, having the following physical data was obtained with using the urea derivative prepared in reference example 14 by the same procedure as reference example 10 and example 5 in order.

TLC (ethyl acetate:acetic acid:water=12:2:1): Rf 0.28;
MS: m/e 426.

EXAMPLE 12

1-[4-(6-hydroxy-2,5,7,8-tetramethyl-3,4-dihydro-2H-benzo[1,2-b]pyran-2-yl)butyl]-3-(3-guanidinophenyl-)urea hydrochloride

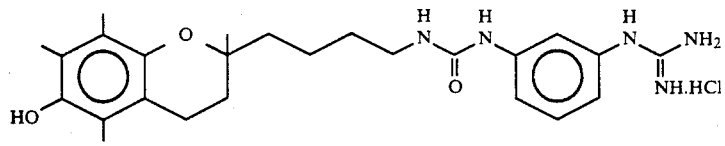

The title compound, of the present invention, having the following physical data was obtained with using the methyl ester prepared in reference example 13 by the same procedure as reference example 1→reference example 2→reference example 9→reference example 3→reference example 14→reference example 10→example 5 in order.

MS: m/e 454, 290, 203, 177, 165, 151, 134, 108, 93;
IR (cm−1):ν 3700–2700, 3333, 2938, 2361, 1669, 1593, 1554, 1494, 1452, 1379, 1246, 1168, 1086, 682.

EXAMPLE 13

N-(3-guanidinophenyl)-4-(6-hydroxy-2,5,7,8-tetramethyl-3,4-dihydro-2H-benzo[1,2-b]pyran-2-yl)butanamide hydrochloride

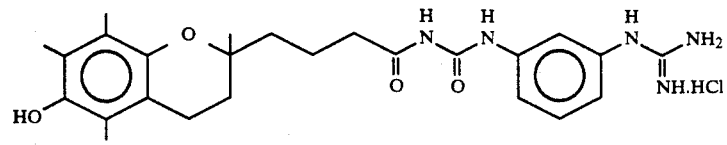

The title compound, of the present invention, having the following physical data was obtained with using the amide compound prepared in reference example 16 by the same procedure as reference example 9→reference example 10→example 5 in order.

TLC (ethyl acetate:acetic acid:water=12:2:1): Rf 0.24;
MS: m/e 424, 407, 382, 291, 274.

EXAMPLE 14

N-[2-(6-hydroxy-2,5,7,8-tetramethyl-3,4-dihydro-2H-benzo[1,2-b]pyran-2-yl)ethyl]-3-ethoxycarbonyl-5guanidinobenzamide hydrochloride

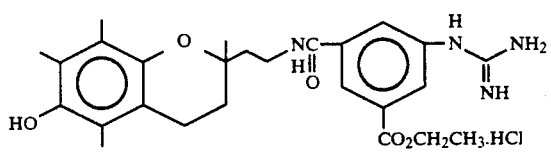

The title compound, of the present invention, having the following physical data was obtained with using the amide compound prepared in reference example 17 by the same procedure as reference example 10 and example 5 in order.

TLC (ethyl acetate:acetic acid:water=15:2:1): Rf 0.24;
MS: m/e 482, 440, 232, 220, 192, 164.

EXAMPLE 15

2-ethoxycarbonyl-4-guanidinophenyl 2-(6-hydroxy-2,5,7,8-tetramethyl-3,4-dihydro-2H-benzo[1,2-b]pyran-2-yl)ethyl ether hydrochloride

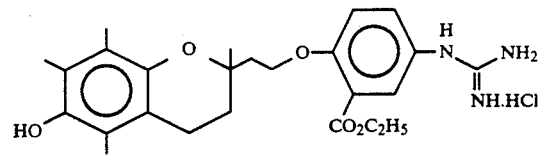

The title compound, of the present invention, having the following physical data was obtained with using the ether compound prepared in reference example 19 by the same procedure as reference example 9→reference example 10→example 5 in order.

TLC (ethyl acetate:acetic acid:water=12:2:1): Rf 0.38;

MS: m/e, 455, 438, 413, 368, 341, 392.

EXAMPLE 16

N-[4-(6-hydroxy-2,5,7,8-tetramethyl-3,4-dihydro-2H-benzo[1,2-b]pyran-2-yl)butyl]-3-ethoxycarbonyl-5-guanidinobenzamide hydrochloride

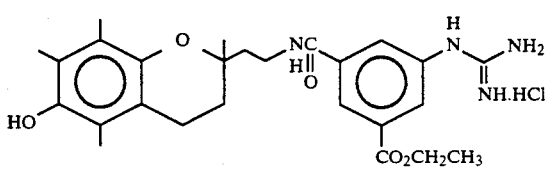

The title compound, of the present invention, having the following physical data was obtained with using the methyl ester prepared in reference example 13 by the same procedure as reference example 1→reference example 2→reference example 3→reference example 17→reference example 9→reference example 10→example 5 in order.

TLC (ethyl acetate:acetic acid:water=12:2:1): Rf 0.54;

MS: m/e 510, 493, 468, 368, 236, 192, 165.

EXAMPLE 17

N-[4-[2-(6-hydroxy-2,5,7,8-tetramethyl-3,4-dihydro-2H-benzo[1,2-b]pyran-2-yl)ethoxy]phenyl]-3-ethoxycarbonyl-5-guanidinobenzamide hydrochloride

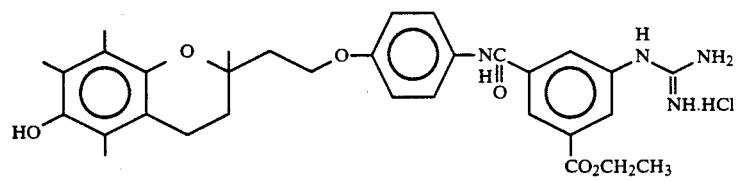

The title compound, of the present invention, having the following physical data was obtained with using the ether compound prepared in reference example 8 by the same procedure as reference example 10→reference example 17→reference example 9→reference example 10→example 5 in order.

TLC (ethyl acetate:acetic acid:water=15:2:1): Rf 0.53;

MS: m/e 575, 461, 411, 369, 277, 185, 93, 75.

EXAMPLE 18

2-ethoxycarbonyl-4-guanidinophenyl 2-(6-hydroxy-2,5,7,8-tetramethyl-3,4-dihydro-2H-benzo[1,2-b]pyran-2-yl)butyl ether hydrochloride

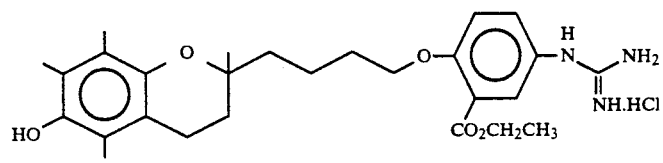

The title compound, of the present invention, having the following physical data was obtained with using the methyl ester prepared in reference example 13 by the same procedure as reference example 1→reference example 18→reference example 19→reference example 9→reference example 10→example 5 in order.

TLC (ethyl acetate:acetic acid:water=12:2:1): Rf 0.33;

MS: m/e 483, 466, 441, 395, 377, 368, 320, 313, 260, 231, 203, 181, 165.

EXAMPLE 19

4-[3-(3-aminoguanidino)propyl]phenyl 2-(6-hydroxy-2,5,7,8-tetramethyl-3,4-dihydro-2H-benzo[1,2-b]pyran-2-yl)ethyl ether hydroiodide

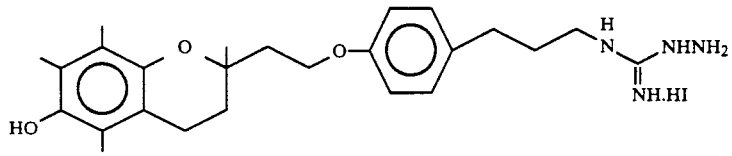

The title compound, of the present invention, having the following physical data was obtained with using the alcohol prepared in reference example 20 by the same procedure as reference example 2→reference example 3→reference example 4→reference example 5→example 3 in order.

TLC (ethyl acetate:acetic acid:water=12:2:1): Rf 0.41;

MS: m/e 441, 426, 277, 262, 185, 165, 93, 75.

EXAMPLE 20

4-(3-aminoguanidino)phenyl 4-(6-hydroxy-2,5,7,8-tetramethyl-3,4-dihydro-2H-benzo[1,2-b]pyran-2-yl)butyl ether hydroiodide

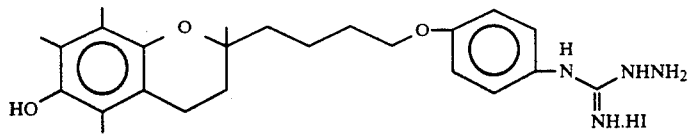

The title compound, of the present invention, having the following physical data was obtained with using the methyl ester prepared in reference example 13 by the same procedure as reference example 1→reference example 8→reference example 9→reference example 10→reference example 4→reference example 5→example 3 in order.

TLC (ethyl acetate:acetic acid:water=10:2:1): Rf 0.36;

MS: m/e 451, 436, 426, 369, 261, 165.

EXAMPLE 21

N-[2-[2-(6-hydroxy-2,5,7,8-tetramethyl-3,4-dihydro-2H-benzo[1,2-b]pyran-2-yl)ethoxy]ethyl]-4-guanidinocinnamamide hydrochloride

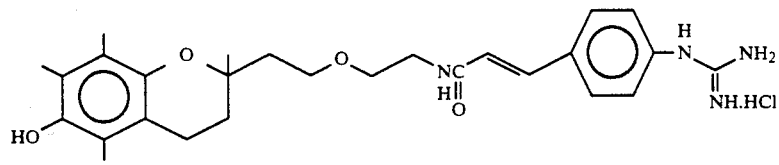

The title compound, of the present invention, having the following physical data was obtained with using tert-butyl ester prepared in reference example 21 by the same procedure as reference example 1→reference example 2→reference example 3→example 2 (with the proviso that 4-guanidinocinnamic acid hydrochloride was used instead of 4-guanidinobenzoic acid hydrochloride) in order.

TLC (ethyl acetate:acetic acid:water =12:2:1): Rf 0.30;

MS: m/e 481, 317, 249, 205, 188, 165.

EXAMPLE 22

N-[4-(6-hydroxy-2,5,7,8-tetramethyl-3,4-dihydro-2H-benzo[1,2-b]pyran-2-yl)butyl]-4-guanidinocinnamamide hydrochloride

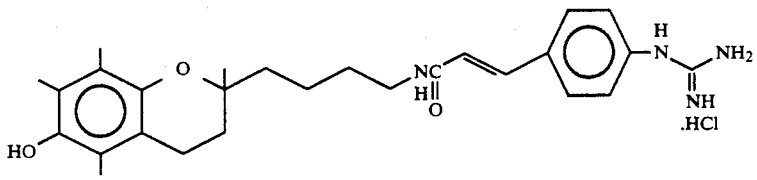

The title compound, of the present invention, having the following physical data was obtained with using the ester prepared in reference example 13 by the same procedure as reference example 1→reference example 2→reference example 9→reference example 3→example 2 (with the proviso that the corresponding appropriate carboxylic acid hydrochloride was used instead of 4-guanidinobenzoic acid hydrochloride) in order.

TLC (ethyl acetate:acetic acid:water=12:2:1): Rf 0.27;

MS: m/e 464, 422, 165, 146.

EXAMPLE 22(a)

N-[4-(6-hydroxy-2,5,7,8-tetramethyl-3,4-dihydro-2H-benzo[1,2,-b]pyran-2-yl)butyl]-2-(4-guanidinophenoxy)acetamide hydrochloride

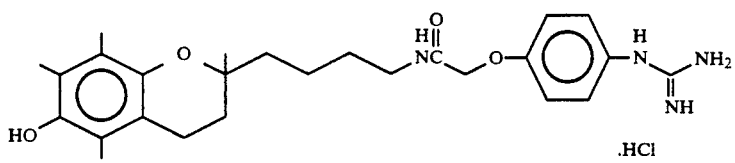

The title compound, of the present invention, having the following physical data was obtained by the same procedure as example 22.

TLC (ethyl acetate:acetic acid:water=12:2:1): Rf 0.25;

MS: m/e 469, 305, 185, 165, 152, 93, 75.

EXAMPLE 23

2-[7-(3-aminoguanidino)hept-2-enyl]-6-hydroxy-2,5,7,8-tetramethyl-3,4-dihydro-2H-benzo[1,2,-b]pyran hydroiodide

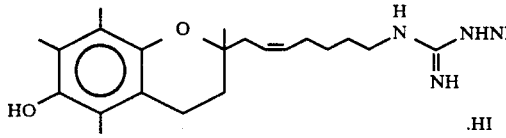

The title compound, of the present invention, having the following physical data was obtained with using the alcohol prepared in reference example 7 by the same procedure as reference example 11→reference example 12 (with the proviso that the corresponding appropriate ester was used instead of methyl (triphenylphosphoranylidene)acetate)→reference example 1→reference example 2→reference example 3→reference example 4→reference example 5→example 3 in order.

TLC (ethyl acetate:acetic acid:water=10:2:1): Rf 0.44;

IR(cm$^{-1}$): ν 3411, 2931, 1657, 1419, 1376, 1343, 1260, 1220, 1162, 1088, 476.

EXAMPLE 24

N-methyl-N-[2-(6-hydroxy-2,5,7,8-tetramethyl-3,4-dihydro-2H-benzo[1,2-b]pyran-2-yl)ethyl]-4-guanidinocinnamamide hydrochloride

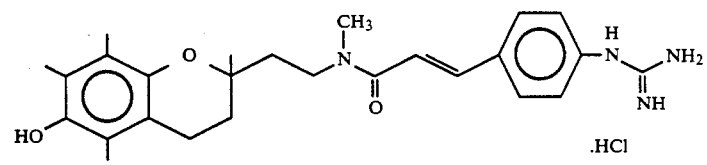

The title compound, of the present invention, having the following physical data was obtained with using the benzopyran derivatives prepared in reference example 23 by the same procedure as reference example 9→example 2 (with the proviso that the corresponding appropriate carboxylic acid hydrochloride was used instead of 4-guanidinobenzoic acid hydrochloride) in order.

TLC (ethyl acetate:acetic acid:water=12:2:1): Rf 0.44;

MS: m/e 451, 287.

EXAMPLE 24(a)

N-benzyl-N-[2-(6-hydroxy-2,5,7,8-tetramethyl-3,4-dihydro-2H-benzo[1,2-b]pyran-2-yl)ethyl]-4-guanidinocinnamamide hydrochloride

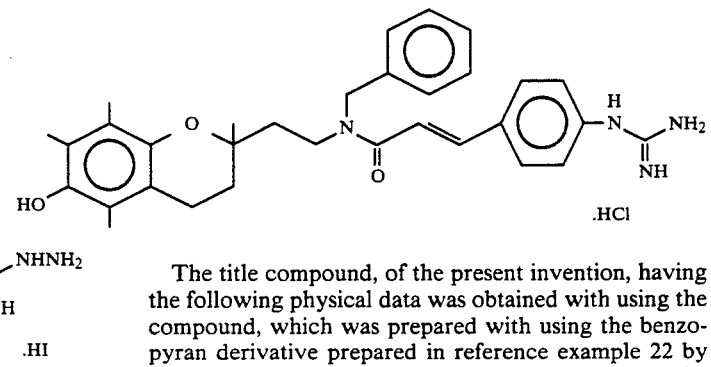

The title compound, of the present invention, having the following physical data was obtained with using the compound, which was prepared with using the benzopyran derivative prepared in reference example 22 by the same procedure as reference example 23 (with the proviso that benzyl bromide was used instead of methyl iodide), by the same procedure as example 24.

TLC (ethyl acetate:acetic acid:water=12:2:1): Rf0.38;

MS: m/e 527, 363, 188.

EXAMPLE 25

N-methyl-N-[4-(6-hydroxy-2,5,7,8-tetramethyl-3,4-dihydro-2H-benzo[1,2-b]pyran-2-yl)butyl]-4-guanidinocinnamamide hydrochloride

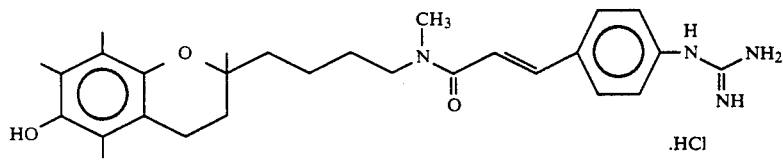

The title compound, of the present invention, having the following physical data was obtained with using 2-(4-aminobutyl)-2,5,7,8-tetramethyl-3,4-dihydro-6-methoxymethoxybenzo[1,2-b]pyran, which was prepared with using the ester prepared in reference example 13 by the same procedure as reference example 1→reference example 2→reference example 3 in order, by the same procedure as example 24.

TLC (ethyl acetate:acetic acid:water=12:2:1): Rf 0.38;

IR(cm$^{-1}$): ν 3333, 2939, 1677, 1646, 1598, 1515, 1546, 1255, 1168, 1088.

EXAMPLE 26

2-(3-aminoguanidino)ethyl 2-(6-hydroxy-2,5,7,8-tetramethyl-3,4-dihydro-2H-benzo[1,2-b]pyran-2-yl)ethyl ether hydrochloride

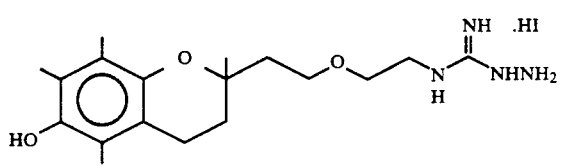

The title compound, of the present invention, having the following physical data was obtained with using the benzopyran derivative prepared in reference example 18 by the same procedure as reference example 8 (with the proviso that 2-nitroethanol was used instead of p-chloronitrobenzene)→reference example 9→ reference example 10→reference example 4→reference example 5→example 3 in order.

TLC (ethyl acetate:acetic acid:water=12:2:1): Rf 0.32;

IR (cm$^{-1}$): $\nu$ 3333, 2927, 1657, 1456, 1379, 1257, 1156, 1111, 1088;

MS: m/e 351, 336, 321, 165.

EXAMPLE 27

4-guanidinophenyl 2-[4-8 2-(6-hydroxy-2,5,7,8-tetramethyl-3,4-dihydro-2H-benzo[1,2-b]pyran-2-yl)ethoxy]phenyl]ethyl ether hydrochloride

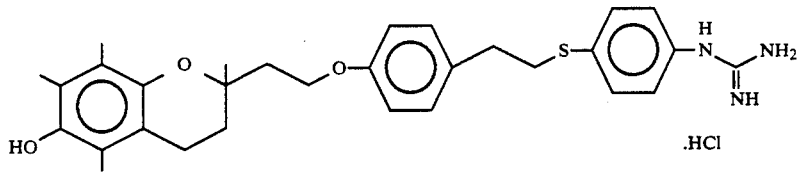

The title compound, of the present invention, having the following physical data was obtained with using the benzopyran derivative prepared in reference example 18 by the same procedure as reference example 8 (with the proviso that p-(2-hydroxyethyl)phenol was used instead of p-chloronitrobenzene)→reference example 18→reference example 8 (with the proviso that p-mercaptonitrophenol was used instead of p-chloronitrobenzene) → reference example 9→reference example 10→example 5 in order.

TLC (ethyl acetate:acetic acid:water=15:2:1): Rf 0.39;

IR(cm$^{-1}$): $\nu$ 3387, 2929, 1669, 1633, 1513, 1250, 1089, 1019, 817.

EXAMPLE 27(a)–27(k)

The compounds, of the present invention, shown in the following table 12 were obtained with using the benzopyran derivative prepared in reference example 18 by the same procedure as example 27 (with the proviso that the corresponding appropriate compounds were used instead of p-(2-hydroxyethyl)phenol and p-mercaptonitrophenol).

TABLE 12

| Example No. | Structure | Name | TLC | Ms m/e |
|---|---|---|---|---|
| 27 (a) | (structure) | 4-guanidinophenyl 2-[2-(6-hydroxy-2,5,7,8-tetramethyl-3,4-dihydro-2H-benzo[1,2-b]-pyran-2-yl)ethoxy]ethyl ether hydrochloride | Rf 0.29 (ethyl acetate: acetic acid: water = 15:2:1) | 427, 410, 385, 264 |
| 27 (b) | (structure) | 4-guanidinophenyl 2-[2-(6-hydroxy-2,5,7,8-tetramethyl-3,4-dihydro-2H-benzo[1,2-b]-pyran-2-yl)ethylthio]ethyl ether hydrochloride | Rf 0.40 (ethyl acetate: acetic acid: water = 15:2:1) | 443, 369, 295, 221 |
| 27 (c) | (structure) | 4-guanidinophenyl 2-[2-(6-hydroxy-2,5,7,8-tetramethyl-3,4-dihydro-2H-benzo[1,2-b]-pyran-2-yl)ethoxy]ethyl thioether hydrochloride | Rf 0.39 (ethyl acetate: acetic acid: water = 15:2:1) | 443, 426, 401, 280 |
| 27 (d) | (structure) | 3-guanidinophenyl 2-[4-[2-(6-hydroxy-2,5,7,8-tetramethyl-3,4-dihydro-2H-benzo[1,2-b]-pyran-2-yl)ethoxy]phenyl]-ethyl thioether hydrochloride | Rf 0.42 (ethyl acetate: acetic acid: water = 15:2:1) | 519, 477, 352, 232, 165 |
| 27 (e) | (structure) | 4-guanidinophenyl 2-[4-[2-(6-hydroxy-2,5,7,8-tetramethyl-3,4-dihydro-2H-benzo[1,2-b]-pyran-2-yl)ethoxy]phenyl]-ethyl ether hydrochloride | Rf 0.35 (ethyl acetate: acetic acid: water = 15:2:1) | 503, 461, 233, 165 |

TABLE 12-continued

| Example No. | Structure | Name | TLC | Ms, m/e |
|---|---|---|---|---|
| 27 (f) | 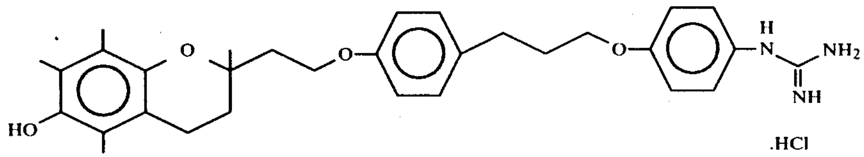 | 4-guanidinophenyl 3-[4-[2-(6-hydroxy-2,5,7,8-tetramethyl-3,4-dihydro-2H-benzo[1,2-b]pyran-2-yl)ethoxy]phenyl]propyl ether hydrochloride | Rf 0.33 (ethyl acetate: acetic acid: water = 15:2:1) | 518, 384, 354, 285, 205, 185, 93 |
| 27 (g) | 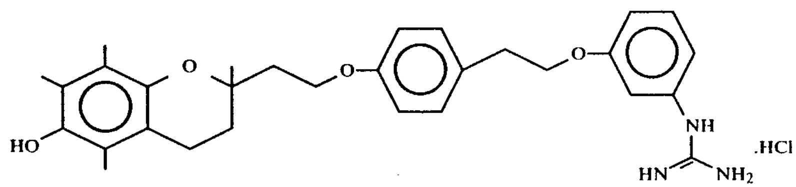 | 3-guanidinophenyl 2-[4-[2-(6-hydroxy-2,5,7,8-tetramethyl-3,4-dihydro-2H-benzo[1,2-b]pyran-2-yl)ethoxy]phenyl]ethyl ether hydrochloride | Rf 0.38 (ethyl acetate: acetic acid: water = 15:2:1) | 503, 461, 352, 340, 232, 205, 165 |
| 27 (h) | 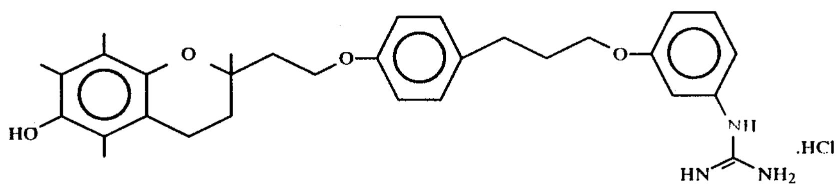 | 3-guanidinophenyl 3-[4-[2-(6-hydroxy-2,5,7,8-tetramethyl-3,4-dihydro-2H-benzo[1,2-b]pyran-2-yl)ethoxy]phenyl]propyl ether hydrochloride | Rf 0.37 (ethyl acetate: acetic acid: water = 15:2:1) | 517, 475, 165, 164 |
| 27 (i) | 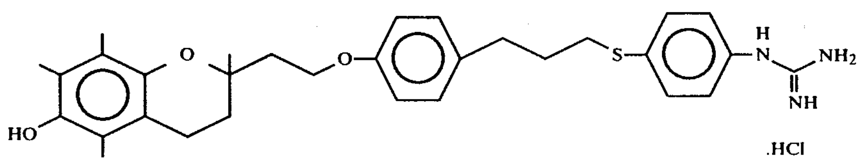 | 4-guanidinophenyl 3-[4-[2-(6-hydroxy-2,5,7,8-tetramethyl-3,4-dihydro-2H-benzo[1,2-b]pyran-2-yl)ethoxy]phenyl]propyl thioether hydrochloride | Rf 0.37 (ethyl acetate: acetic acid: water = 15:2:1) | 533, 491, 259, 165, 125 |
| 27 (j) | 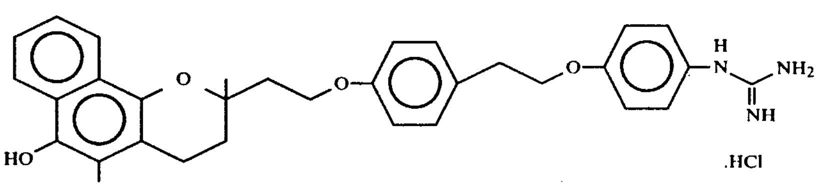 | 4-guanidinophenyl 2-[4-[2-(2,5-dimethyl-6-hydroxy-3,4-dihydro-2H-naphtho[1,2-b]pyran-2-yl)ethoxy]phenyl]ethyl ether hydrochloride | Rf 0.5 (ethyl acetate: acetic acid: water = 15:2:1) | 526, 340, 187, 151, 135, 121, 93 |

TABLE 12-continued
| Example No. | Structure | Name | TLC | Ms m/e |
|---|---|---|---|---|
| 27 (k) | 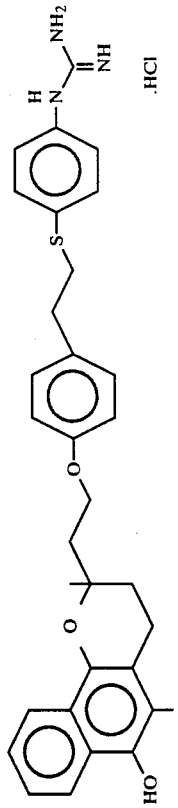.HCl | 4-guanidinophenyl 2-[4-[2-(2,5-dimethyl-6-hydroxy-3,4-dihydro-2H-naphtho-[1,2-b]pyran-2-yl]ethoxy]-phenyl]ethyl thioether hydrochloride | Rf 0.5 (ethyl acetate: acetic acid: water = 15:2:1) | 542, 356, 187, 167, 121 |

EXAMPLE 28

3-quanidinophenyl 2-[4-[4-(6-hydroxy-2,5,7,8-tetramethyl-3,4-dihydro-2H-benzo[1,2-b]pyran-2-yl)butoxy]phenyl]ethyl ether hydrochloride

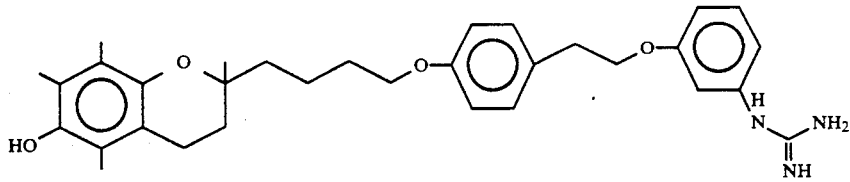

The title compound, of the present invention, having the following physical data was obtained with using the benzopyran derivative, which was prepared with using the ester prepared in reference example 13 by the same procedures as reference example 1→reference example 18 in order, by the same procedure as example 27 (with the proviso that 3-nitrophenol was used instead of p-mercaptonitrophenol).

TLC (chloroform:methanol=4:1): Rf 0.39;
IR(cm−1): ν 3377, 2932, 1741, 1678, 1585, 1512, 1494, 1459, 1343, 1246, 1113, 1085.

EXAMPLE 28(a)–28(c)

The compounds, of the present invention, shown in the following table 13 were obtained with using the benzopyran derivatives, which were prepared with using the ester prepared in reference example 13 by the same procedure as reference example 1→reference example 18 in order, by the same procedure as example 28 (with the proviso that the corresponding appropriate compounds were used instead of 3-nitrophenol).

TABLE 13

| Example No. | Structure | Name | TLC | MS m/e |
|---|---|---|---|---|
| 28(a) | 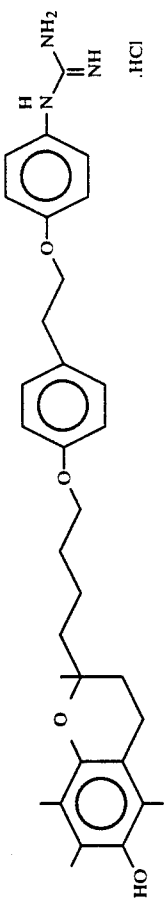 | 4-guanidinophenyl 2-[4-[4-(6-hydroxy-2,5,7,8-tetramethyl-3,4-dihydro-2H-benzo[1,2-b]-pyran-2-yl)butoxy]phenyl]-ethyl ether hydrochloride | Rf 0.33 (chloroform: methanol: acetic acid = 80:20:1) | 532, 368, 284, 185, 165, 93 |
| 28(b) | 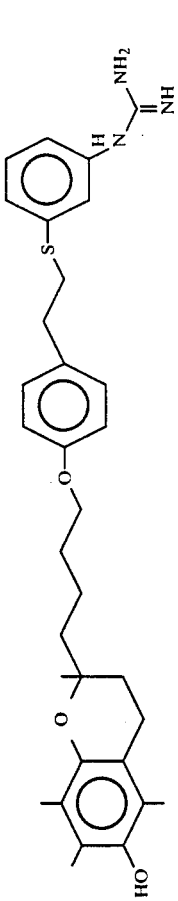 | 3-guanidinophenyl 2-[4-[4-(6-hydroxy-2,5,7,8-tetramethyl-3,4-dihydro-2H-benzo[1,2-b]-pyran-2-yl)butoxy]phenyl]-ethyl thioether hydrochloride | Rf 0.4 (chloroform: methanol: acetic acid = 80:20:1) | 548, 384, 300, 203, 165 |
| 28(c) | 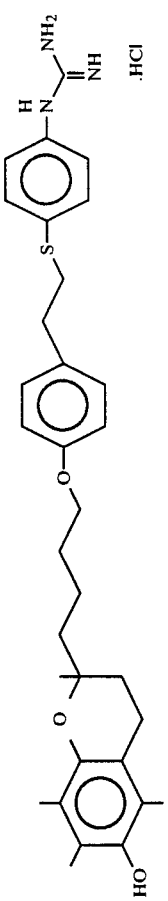 | 4-guanidinophenyl 2-[4-[4-(6-hydroxy-2,5,7,8-tetramethyl-3,4-dihydro-2H-benzo[1,2-b]-pyran-2-yl)butoxy]phenyl]-ethyl thioether hydrochloride | Rf 0.3 (chloroform: methanol: acetic acid = 80:20:1) | 548, 384, 165 |

EXAMPLE 29

4-guanidinophenyl 6-(6-hydroxy-2,5,7,8-tetramethyl-3,4-dihydro-2H-benzo[1,2-b]pyran-2-yl)-n-hexyl thioether hydrochloride

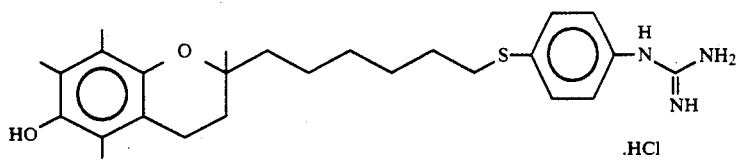

The title compound, of the present invention, having the following physical data was obtained with using the ester prepared in reference example 13 by the same procedure as reference example 1→reference example 11→reference example 12→reference example 13→reference example 1→reference example 18→reference example 8 (with the proviso that 4-mercaptonitrophenol was used instead of p-chloronitrobenzene)→reference example 9→reference example 10→example 5 in order.

TLC (ethyl acetate:acetic acid:water=10:2:1): Rf 0.39;
MS: m/e 455, 438, 413, 165.

EXAMPLE 29(a)

4-guanidinophenyl 6-(6-hydroxy-2,5,7,8-tetramethyl-3,4-dihydro-2H-benzo[1,2-b]pyran-2-yl)-n-hexyl ether hydrochloride

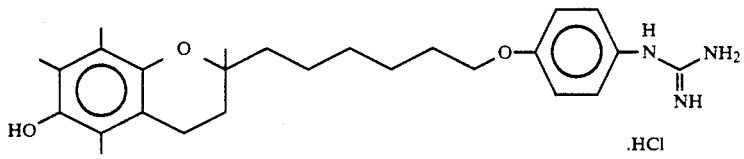

The title compound, of the present invention, having the following physical data was obtained with using the ester prepared in reference example 13 by the same procedure as example 29 (with the proviso that p-chloronitrobenzene was used instead of 4-mercaptonitrophenol).

TLC (ethyl acetate:acetic acid:water=10:2:1): Rf 0.37;
MS: m/e 439, 422, 397, 276, 165, 109.

PREPARATIVE EXAMPLE

The following components were admixed in conventional method and punched out to obtain 100 tablets each containing 50 mg of active ingredient.

| | |
|---|---|
| 2-(6-hydroxy-2,5,7,8-tetramethyl-3,4-dihydro-2H-benzo[1,2-b]pyran-2-yl)ethyl 4-guanidinomethylbenzoate hydrochloride | 5 g |
| Cellulose calcium glycolate (distintegrating agent) | 0.2 g |
| Magnesium stearate (lubricating agent) | 0.1 g |
| Microcrystaline cellulose | 4.7 g |

What is claimed is:
1. A benzopyran derivative of the formula:

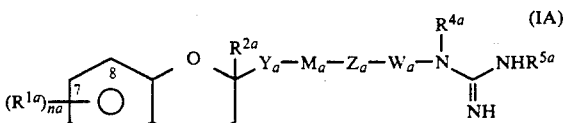

wherein $R^{1a}$ is hydrogen, C1-4 alkyl or C1-4 alkoxy; or two $R^{1a}$ taken together with 7th- and 8th-carbon to which they are attached form C6 carbocyclic ring;
$R^{2a}$ is hydrogen or C1-4 alkyl;
$R^{3a}$ is hydrogen, C2-4 acyl or benzoyl;
na is 1-3;
Ya is C1-7 alkylene, C2-7 alkenylene or C2-7 alkynylene;
Ma is
  i) bond or
  ii) a group of the formula: —Da—Ba;
Da is
  i) —O— or
  ii) —S—;
Ba is
  i) C1-4 alkylene;
Za is
  i) —CONR$^{9a}$—, or
  ii) NR$^{9a}$CO—;
Wa is a group of the formula: —W1a—Aa—W2a;
Aa is
  i) a group of the formula:

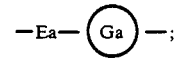

Ea is
  i) bond,
  ii) —O— or
  iii) —S—;
Ga is C4-10 carbocyclic or C4-10 carbocyclic ring substituted by one to three C1-4 alkyl, C1-4 alkoxy, halogen, a group of the formula: —COOR$^{7a}$, trihalomethyl or acetamido;
W1a and W2a each, independently, is
  i) bond
  ii) C1-4 alkylene,
  iii) C2-4 alkenylene or
  iv) C2-4 alkynylene;
$R^{4a}$ is hydrogen or C1-4 alkyl;
$R^{5a}$ is hydrogen, C1-4 alkyl or amino;
$R^{7a}$ is hydrogen or C1-4 alkyl;
$R^{9a}$ is hydrogen, C1-4 alkyl or benzyl;

with the proviso that:
i) Da is bonded to Ya and Ba is bonded to Za;
ii) Ea is bonded to W1a and Ga is bonded to W2a;
iii) a double or triple bond in alkenylene or alkynylene is not directly bonded to oxygen; and
iv) when Aa represents

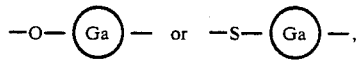

W1a does not represent a bond;
or pharmaceutically acceptable acid addition salt thereof.

2. A compound according to claim 1, wherein is benzene or naphthalene ring, or benzene or naphthalene ring substituted by one to three C1–4 alkyl, C1–4 alkoxy, halogen, a group of the formula: —COOR$^{7a}$, trihalomethyl or acetamido.

3. A compound according to claim 2, wherein Ma is bond.

4. A compound according to claim 3, which is

N-[2-(6-hydroxy-2,5,7,8-tetramethyl-3,4-dihydro-2H-benzo[1,2-b]pyran-2-yl)ethyl]-4-guanidinocinnamamide, N-[2-(6-hydroxy-2,5,7,8-tetramethyl-3,4-dihydro-2H-benzo[1,2-b]pyran-2-yl)ethyl]-3-ethoxycarbonyl-5-guanidinobenzamide, N-[2-(6-hydroxy-2,5,7,8-tetramethyl-3,4-dihydro-2H-naphtho[1,2-b]pyran-2-yl)ethyl]-3-guanidinobenzamide, N-[4-(6-hydroxy-2,5,7,8-tetramethyl-3,4-dihydro-2H-benzo[1,2-b]pyran-2-yl)butyl]-4-guanidinocinnamamide, or N-methyl-N-[2-(6-hydroxy-2,5,7,8-tetramethyl-3,4-dihydro-2H-benzo[1,2-b]pyran-2-yl)ethyl]-4-guanidinocinnamamide.

5. A compound according to claim 2, wherein Ma is a group of the formula: —Da—Ba—.

6. A compound according to claim 1, wherein is C4–7 cycloalkane or C4–7 cycloalkane substituted by one to three C1–4 alkyl, C1–4 alkoxy, halogen, a group of the formula: —COOR$^{7a}$, trihalomethyl or acetamido.

* * * * *